(12) United States Patent
Huang et al.

(10) Patent No.: US 9,937,128 B2
(45) Date of Patent: Apr. 10, 2018

(54) LIPOSOMES COMPRISING A CALCIUM PHOSPHATE-CONTAINING PRECIPITATE

(75) Inventors: Leaf Huang, Durham, NC (US); Jun Li, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 63 days.

(21) Appl. No.: 13/388,538

(22) PCT Filed: Aug. 3, 2010

(86) PCT No.: PCT/US2010/044209
§ 371 (c)(1),
(2), (4) Date: Apr. 23, 2012

(87) PCT Pub. No.: WO2011/017297
PCT Pub. Date: Feb. 10, 2011

(65) Prior Publication Data
US 2012/0201872 A1    Aug. 9, 2012

Related U.S. Application Data

(60) Provisional application No. 61/230,783, filed on Aug. 3, 2009, provisional application No. 61/258,028, filed on Nov. 4, 2009.

(51) Int. Cl.
*A61K 9/127* (2006.01)
*A61K 48/00* (2006.01)
*C12N 15/11* (2006.01)

(52) U.S. Cl.
CPC .......... *A61K 9/1271* (2013.01); *A61K 9/1277* (2013.01); *A61K 48/0025* (2013.01); *C12N 15/111* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,615,885 A | 10/1986 | Nakagame et al. | |
| 4,789,633 A * | 12/1988 | Huang | A61K 9/127 264/4.1 |
| 5,013,556 A * | 5/1991 | Woodle et al. | 424/450 |
| 5,219,577 A | 6/1993 | Kossovsky et al. | |
| 5,512,295 A | 4/1996 | Kornberg et al. | |
| 5,891,468 A * | 4/1999 | Martin | A61K 9/1271 424/450 |
| 6,159,504 A | 12/2000 | Kumabe | |
| 6,200,599 B1 * | 3/2001 | Nantz et al. | 424/450 |
| 6,214,386 B1 | 4/2001 | Santus et al. | |
| 6,270,700 B1 | 8/2001 | Ignatious | |
| 6,355,271 B1 | 3/2002 | Bell et al. | |
| 6,482,517 B1 | 11/2002 | Anderson | |
| 6,555,376 B2 | 4/2003 | Maitra et al. | |
| 6,897,196 B1 * | 5/2005 | Szoka et al. | 514/1 |
| 7,004,974 B1 | 2/2006 | Larsson et al. | |
| 7,005,140 B2 * | 2/2006 | Zhang | A61K 47/48815 424/450 |
| 7,063,849 B1 | 6/2006 | Thibodeau et al. | |
| 7,244,451 B2 | 7/2007 | Bosch et al. | |
| 7,332,586 B2 | 2/2008 | Franzen et al. | |
| 7,364,755 B2 | 4/2008 | Cucala Escoi et al. | |
| 7,368,295 B2 | 5/2008 | Tovar et al. | |
| 7,381,421 B2 | 6/2008 | Gregoriadis | |
| 7,384,923 B2 | 6/2008 | Gregoriadis | |
| 7,404,969 B2 | 7/2008 | Chen et al. | |
| 7,459,283 B2 | 12/2008 | Wertz et al. | |
| 2002/0054914 A1 * | 5/2002 | Morcol | A61K 9/1611 424/491 |
| 2003/0072794 A1 * | 4/2003 | Boulikas | 424/450 |
| 2003/0185869 A1 | 10/2003 | Wertz et al. | |
| 2004/0247680 A1 | 12/2004 | Farokhzad et al. | |

(Continued)

FOREIGN PATENT DOCUMENTS

WO    WO-1995-027478    * 10/1995
WO    WO 00/00177 A1    1/2000

(Continued)

OTHER PUBLICATIONS

Heywood BR, and Eanes E, An ultrastructural study of the effects of acidic phospholipid substitutions on calcium phosphate precipitation in anionic liposomes, 1992, Springer, Calcified Tissue International, 50, 149-156.*
Heywood BR, An ultrastructural study of the effects of acidic phospholipid substitutions on calcium phosphate precipitation in anionic liposomes, 1992, Calcif Tissue Int, 50, 149-156.*
Banerjee R, Anisamide targeted stealth liposomes: a potent carrier for targeting doxorubicin to human prostate cancer cells, 2004, Intl J Cancer, 112, 693-700.*
Kotchetkov R, Antineoplastic activity of a novel multimeric gemcitabine monophosphate prodrug against thyroid cancer cells in vitro, 2000, Anticancer Res, 20, 2915-2922.*
Liposome, The American Heritage Dictionary, 2007, Houghton Mifflin Company.*

(Continued)

*Primary Examiner* — Celeste A Roney
(74) *Attorney, Agent, or Firm* — Alston & Bird LLP

(57) ABSTRACT

Provided herein are methods and compositions for the delivery of bioactive compounds to a cell, tissue, or physiological site. The compositions comprise delivery system complexes comprising liposomes encapsulating a biodegradable ionic precipitate having incorporated therein a bioactive compound and delivery system complexes comprising a biodegradable ionic precipitate ionically bound to a surrounding lipid bilayer, wherein the biodegradable ionic precipitate comprises a bioactive compound. Also provided herein are methods for the treatment of a disease or an unwanted condition in a subject, wherein the methods comprise administering the delivery system complexes comprising bioactive compounds that have therapeutic activity against the disease or unwanted condition to the subject.

27 Claims, 16 Drawing Sheets

(56) References Cited

U.S. PATENT DOCUMENTS

| | | | |
|---|---|---|---|
| 2005/0032880 A1 | 2/2005 | Lorenz et al. | |
| 2005/0037075 A1 | 2/2005 | Farokhzad et al. | |
| 2005/0191344 A1* | 9/2005 | Zalipsky et al. | 424/450 |
| 2005/0234114 A1* | 10/2005 | Lee | A61K 9/0048 514/365 |
| 2006/0045891 A1 | 3/2006 | Lovalenti | |
| 2007/0042031 A1* | 2/2007 | MacLachlan | A61K 9/127 424/450 |
| 2007/0104775 A1* | 5/2007 | Panzner | A61K 9/0019 424/450 |
| 2007/0154559 A1 | 7/2007 | Pai et al. | |
| 2008/0096797 A1 | 4/2008 | Li et al. | |
| 2008/0241256 A1* | 10/2008 | Kuhn | A61K 9/0019 424/489 |
| 2008/0293805 A1 | 11/2008 | Lin | |
| 2009/0048197 A1 | 2/2009 | Chen et al. | |
| 2009/0061010 A1 | 3/2009 | Zale et al. | |
| 2009/0074852 A1* | 3/2009 | Kaufmann et al. | 424/450 |
| 2009/0274763 A1 | 11/2009 | Ohno et al. | |

FOREIGN PATENT DOCUMENTS

| | | | |
|---|---|---|---|
| WO | WO 03/064459 A1 | | 8/2003 |
| WO | WO-2006-116107 | * | 11/2006 |
| WO | WO 2006/116107 A2 | | 11/2006 |
| WO | WO 2007/074604 A1 | | 7/2007 |
| WO | WO 2008/000042 A1 | | 1/2008 |
| WO | WO 2009/142893 A2 | | 11/2009 |

OTHER PUBLICATIONS

Roy I, Calcium phosphate nanoparticles as novel non-viral vectors for targeted gene delivery, International Journal of Pharmaceutics, 2003, 250, 25-33.*

Eanes, E., et al., "Calcium Phosphate Formation in Aqueous Suspensions of Multilamellar Liposomes," *Calcif Tissue Int* (1984), vol. 36(1), pp. 421-430.

Heywood, B., et al., "An Ultrastructural Study of Calcium Phosphate Formation in Multilamellar Liposome Suspensions," *Calcif Tissue Int*, 1987, vol. 41(4), pp. 192-201.

Heywood, B., et al.,"An Ultrastructural Study of the Effects of Acidic Phospholipid Substitutions on Calcium Phosphate Precipitation in Anionic Liposomes," *Calcif Tissue Int*, 1992, vol. 50(2), pp. 149-156.

Li, S., et al., "Targeted Delivery of Antisense Oligodeoxynucleotide and Small Interference RNA into Lung Cancer Cells," *Molecular Pharmaceutics*, 2006, pp. 579-588, vol. 3(5), American Chemical Society.

Li, S., et al., "Efficient gene silencing in metastatic tumor by siRNA formulated in surface-modified nanoparticles," *Journal of Controlled release*, 2008, pp. 77-84, vol. 126, Elsevier.

Li, S., et al., "Tumor-targeted Delivery of siRNA by Self-assembled Nanoparticles," *Molecular Therapy*, Jan. 2008, pp. 163-169, vol. 16(1), The American Society of gene Therapy.

Li, S., et al., "Efficient Oncogene Silencing and Metastasis Inhibition via Systemic Delivery of siRNA," *Molecular Therapy*, May 2008, pp. 942-946, vol. 16(5), The American Society of Gene Therapy.

\* cited by examiner

LIPOSOMES COMPRISING A CALCIUM PHOSPHATE-CONTAINING PRECIPITATE

CROSS-REFERENCE TO RELATED APPLICATIONS

This application is the U.S. National Stage of International Application PCT/US2010/044209 filed Aug. 3, 2010, which claims the benefit of U.S. Provisional Application No. 61/230,783, filed Aug. 3, 2009, and U.S. Provisional Application No. 61/258,028, filed Nov. 4, 2009, all of which are hereby incorporated herein in their entirety by reference.

FEDERALLY SPONSORED RESEARCH OR DEVELOPMENT

This invention was made with United States Government support under grant number CA 129825 awarded by the National Cancer Institute, a division of the National Institutes of Health. The United States Government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 381521SEQLIST.TXT, created on Nov. 4, 2009, and having a size of 839 bytes and is filed concurrently with the specification. The sequence listing contained in this ASCII formatted document is part of the specification and is herein incorporated by reference in its entirety.

FIELD OF THE INVENTION

The present invention involves the delivery of bioactive compounds using lipid-comprising delivery system complexes.

BACKGROUND OF THE INVENTION

The development of new forms of therapeutics which use macromolecules such as proteins or nucleic acids as therapeutic agents has created a need to develop new and effective means of delivering such macromolecules to their appropriate cellular targets. Lipid-comprising vehicles have been developed to aid in the delivery of polynucleotides and other macromolecules. However, many of these vehicles are unable to efficiently release the incorporated bioactive compounds into the cytoplasm of cells or are associated with toxic side effects due to the stimulation of an inflammatory response when administered in vivo. Considering the great potential of novel macromolecular therapeutics in the treatment of various disorders, the need exists for the development of stable vehicles that are able to effectively deliver these therapeutics with minimal immunogenic effect.

BRIEF SUMMARY OF THE INVENTION

Provided herein are methods and compositions for the delivery of bioactive compounds to cells, tissues, or particular physiological sites. Compositions include delivery system complexes comprising a biodegradable ionic precipitate comprising a bioactive compound, wherein the precipitate is encapsulated by a liposome. The delivery system complexes can comprise any type of bioactive compound, including but not limited to, polynucleotides, polypeptides, and drugs. The delivery system complexes provided herein can be formulated into nano-sized complexes, including liposome/calcium phosphate (LCP) nanoparticles that comprise a liposome encapsulating a calcium phosphate nanoprecipitate having a bioactive compound incorporated therein. Delivery system complexes are also provided that comprise a biodegradable ionic precipitate comprising a bioactive compound surrounded by a lipid bilayer, wherein the biodegradable ionic precipitate is ionically bound to the inner leaflet of the lipid bilayer.

The delivery system complexes can be used to deliver bioactive compounds to cells. Therefore, provided herein are methods for delivering a bioactive compound to a cell, wherein the method comprises contacting a cell with a delivery system complex comprising a liposome-encapsulated biodegradable ionic precipitate comprising a bioactive compound or with a delivery system complex comprising a biodegradable ionic precipitate comprising a bioactive compound surrounded by a lipid bilayer, wherein the biodegradable ionic precipitate is ionically bound to the inner leaflet of the lipid bilayer.

Further, methods are provided for the treatment of diseases or unwanted conditions in a subject, wherein the method comprises administering a delivery system complex comprising a liposome-encapsulated biodegradable ionic precipitate having a bioactive compound incorporated therein or a delivery system complex comprising a biodegradable ionic precipitate comprising a bioactive compound surrounded by a lipid bilayer, wherein the biodegradable ionic precipitate is ionically bound to the inner leaflet of the lipid bilayer to the subject, wherein the bioactive compound has therapeutic activity against the disease or unwanted condition.

Delivery system complexes can comprise a targeting ligand and are referred to as targeted delivery system complexes. These targeted delivery system complexes can specifically target the bioactive compound to diseased cells, enhancing the effectiveness and minimizing the toxicity of the delivery system complexes.

Further provided herein are methods for making the delivery system complexes, which includes mixing a charged biodegradable ionic precipitate with a liposome of the opposite charge. The biodegradable ionic precipitate can be produced through the formation of a water-in-oil microemulsion. Additional methods for making delivery system complexes include mixing a first and a second reverse microemulsion comprising a cation, and an anion and an anionic lipid, respectively, to form a biodegradable ionic precipitate, wherein the bioactive compound is within the first reverse microemulsion or the second reverse microemulsion, washing the biodegradable ionic precipitate and then solubilizing it in a volatile, organic solvent, followed by the addition of a lipid and evaporation of the volatile, organic solvent The following embodiments are encompassed by the present invention:

1. A delivery system complex comprising a biodegradable ionic precipitate comprising a bioactive compound, wherein said biodegradable ionic precipitate is encapsulated by a liposome.

2. The delivery system complex of embodiment 1, wherein said delivery system complex has a diameter of about 150 nm.

3. The delivery system complex of embodiment 1 or 2, wherein said delivery system complex has a zeta potential of about +40 mV.

4. The delivery system complex of any one of embodiments 1-3, wherein said bioactive compound comprises a polynucleotide of interest or a polypeptide of interest.

5. The delivery system complex of embodiment 4, wherein said polynucleotide of interest comprises a silencing element, wherein expression or introduction of said silencing element into a cell reduces the expression of a target polynucleotide or the polypeptide encoded thereby.

6. The delivery system complex of embodiment 5, wherein said silencing element comprises an interfering RNA.

7. The delivery system complex of embodiment 6, wherein said interfering RNA comprises an siRNA.

8. The delivery system complex of embodiment 5, wherein said target polynucleotide comprises an oncogene.

9. The delivery system complex of any one of embodiments 1-8, wherein said liposome comprises a lipid bilayer surrounding an inner core, and wherein said inner core is essentially free of water.

10. The delivery system complex of any one of embodiments 1-9, wherein said liposome comprises a cationic liposome.

11. The delivery system complex of embodiment 10, wherein said cationic liposome comprises DOTAP and cholesterol.

12. The delivery system complex of embodiment 11, wherein said cationic liposome comprises DOTAP and cholesterol at a molar ratio of about 1:1.

13. The delivery system complex of any one of embodiments 10-12, wherein said biodegradable ionic precipitate has a negatively charged surface.

14. The delivery system complex of any one of embodiments 1-13, wherein said biodegradable ionic precipitate comprises at least one of a divalent cation, a divalent anion, a trivalent cation, and a trivalent anion.

15. The delivery system complex of embodiment 14, wherein said divalent cation is selected from the group consisting of calcium, magnesium, and manganese.

16. The delivery system complex of any one of embodiments 1-15, wherein said biodegradable ionic precipitate dissolves at a pH of about 5.0.

17. The delivery system complex of any one of embodiments 1-13, wherein said biodegradable ionic precipitate is selected from the group consisting of: calcium phosphate, calcium citrate, calcium carbonate, magnesium carbonate, magnesium phosphate, and manganous phosphate.

18. The delivery system complex of embodiment 17, wherein said biodegradable ionic precipitate comprises calcium phosphate.

19. The delivery system complex of any one of embodiments 1-18, wherein said liposome comprises a lipid bilayer having an inner leaflet and an outer leaflet, and wherein said outer leaflet comprises a lipid-polyethylene glycol (lipid-PEG) conjugate.

20. The delivery system complex of embodiment 19, wherein said lipid-PEG conjugate comprises a PEG molecule having a molecular weight of about 2000 g/mol.

21. The delivery system complex of embodiment 20, wherein said lipid-PEG conjugate comprises a 1,2-distearoyl-sn-glycero-3-phosphoethanolamine-N-carboxy-polyethylene glycol$_{2000}$ (DSPE-PEG$_{2000}$).

22. The delivery system complex of any one of embodiments 1-21, wherein said liposome comprises a lipid bilayer having an inner leaflet and an outer leaflet, and wherein said outer leaflet comprises a targeting ligand, thereby forming a targeted delivery system complex, wherein said targeting ligand targets said targeted delivery system complex to a targeted cell.

23. The delivery system complex of embodiment 22, wherein said targeting ligand comprises a benzamide derivative.

24. The delivery system complex of embodiment 23, wherein said benzamide derivative comprises anisamide.

25. The delivery system complex of embodiment 24, wherein said anisamide is conjugated to 1,2-distearoyl-sn-glycero-3-phosphoethanolamine-N-carboxy-polyethylene glycol (DSPE-PEG), thereby producing DSPE-PEG-AA.

26. The delivery system complex of any one of embodiments 22-25, wherein said targeted cell comprises a cancer cell.

27. The delivery system complex of embodiment 26, wherein said cancer is selected from the group consisting of a bladder cancer, a brain tumor, a breast cancer, a cervical cancer, a colorectal cancer, an esophageal cancer, an endometrial cancer, a hepatocellular carcinoma, a laryngeal cancer, a lung cancer, an osteosarcoma, an ovarian cancer, a pancreatic cancer, a prostate cancer, a renal cancer, and a thyroid cancer.

28. The delivery system complex of embodiment 27, wherein said cancer comprises a lung cancer.

29. A pharmaceutical composition comprising the delivery system complex of any one of embodiments 1-28, 57-89, and 120 and a pharmaceutically acceptable carrier.

30. A method of delivering a bioactive compound to a cell, said method comprising contacting a cell with the delivery system complex of any one of embodiments 1-28, 57-89, and 120.

31. A method of treating a disease or unwanted condition in a subject, said method comprising administering the pharmaceutical composition according to embodiment 29 to said subject, wherein said bioactive compound has therapeutic activity against said disease or unwanted condition.

32. The method of embodiment 31, wherein said disease comprises a cancer.

33. A method of making a delivery system complex comprising a biodegradable ionic precipitate comprising a bioactive compound, wherein said biodegradable ionic precipitate is encapsulated by a liposome, said method comprising mixing a liposome and an aqueous dispersion of a biodegradable ionic precipitate comprising a bioactive compound, wherein said liposome comprises a cationic liposome and said biodegradable ionic precipitate has a negatively charged surface, or wherein said liposome comprises an anionic liposome and said biodegradable ionic precipitate has a positively charged surface.

34. The method of embodiment 33, wherein said liposome comprises a cationic liposome.

35. The method of embodiment 34, wherein said method further comprises imparting a negative charge to the surface of said biodegradable ionic precipitate.

36. The method of embodiment 34, wherein said biodegradable ionic precipitate has a zeta potential of about −14 mV to about −20 mV.

37. The method of embodiment 36, wherein said zeta potential of said biodegradable ionic precipitate is about −16 mV.

38. The method of any one of embodiments 33-37, wherein said method further comprises making said aqueous dispersion of said biodegradable ionic precipitate comprising a bioactive compound, wherein said making said aqueous dispersion of said biodegradable ionic precipitate comprises the steps of:

a) mixing an aqueous solution comprising an anion, an aqueous solution comprising a cation, an aqueous solution comprising a bioactive compound, a non-ionic surfactant, and an organic solvent, thereby producing a water-in-oil microemulsion comprising a biodegradable ionic precipitate;

b) purifying said biodegradable ionic precipitate from said non-ionic surfactant and said organic solvent; and c) dispersing said biodegradable ionic precipitate in an aqueous solution.

39. The method of embodiment 38, wherein said cation comprises a calcium ion and wherein said anion comprises a phosphate ion, and wherein said biodegradable ionic precipitate comprises a calcium phosphate precipitate.

40. The method of embodiment 38, wherein said anion comprises a divalent anion or a trivalent anion or wherein said cation comprises a divalent cation or a trivalent cation.

41. The method of any one of embodiments 38-40, wherein said organic solvent comprises hexanol and cyclohexane.

42. The method of embodiment 41, wherein the volume/volume ratio of said cyclohexane to hexanol is about 7.5 to 1.7

43. The method of any one of embodiments 38-42, wherein said non-ionic surfactant comprises Triton X-100.

44. The method of any one of embodiments 38-43, wherein the volume/volume ratio of said organic solvent to said non-ionic surfactant is about 9.2 to 1.8.

45. The method of embodiment 44, wherein said organic solvent comprises cyclohexane and hexanol and wherein the volume/volume ratio of cyclohexane to hexanol to Triton X-100 is about 7.5 to 1.7 to 1.8.

46. The method of any one of embodiments 38-45, wherein said purifying said biodegradable ionic precipitate from said non-ionic surfactant and said organic solvent comprises the steps of:

i) adsorbing said biodegradable ionic precipitate to a silica gel;

ii) washing said silica gel with a polar organic solvent; and iii) eluting said biodegradable ionic precipitate from said silica gel with an aqueous solution comprising a polar organic solvent.

47. The method of embodiment 46, wherein said silica gel is washed with ethanol.

48. The method of embodiment 46 or 47, wherein said biodegradable precipitate is eluted from said silica gel with a solution comprising water and ethanol.

49. The method of embodiment 48, wherein the volume/volume ratio of water to ethanol is about 1:3.

50. The method of any one of embodiments 38-49, wherein said method further comprises imparting a negative charge to the surface of said biodegradable ionic precipitate, wherein said imparting a negative charge to the surface of said biodegradable ionic precipitate comprises adding citrate to said water-in-oil microemulsion.

51. The method of any one of embodiments 33-50, wherein said method further comprises a post-insertion step, wherein at least one of a lipid-targeting ligand conjugate and a lipid-polyethylene glycol (lipid-PEG) conjugate is post-inserted into said liposome of said delivery system complex.

52. The method of embodiment 51, wherein said lipid-PEG conjugate comprises a PEG molecule having a molecular weight of about 2000 g/mol.

53. The method of embodiment 52, wherein said lipid-PEG conjugate comprises a 1,2-distearoyl-sn-glycero-3-phosphoethanolamine-N-carboxy-polyethylene glycol$_{2000}$ (DSPE-PEG$_{2000}$).

54. The method of embodiment 51, wherein said lipid-targeting ligand conjugate comprises a targeting ligand comprising a benzamide derivative.

55. The method of embodiment 54, wherein said benzamide derivative comprises anisamide.

56. The method of embodiment 55, wherein said lipid-targeting ligand conjugate comprises 1,2-distearoyl-sn-glycero-3-phosphoethanolamine-N-carboxy-polyethylene glycol (DSPE-PEG), thereby producing DSPE-PEG-AA.

57. A delivery system complex produced according to any one of the methods of embodiments 33-56.

58. A delivery system complex comprising a biodegradable ionic precipitate comprising a bioactive compound surrounded by a lipid bilayer comprising an inner and an outer leaflet, wherein said biodegradable ionic precipitate is ionically bound to the inner leaflet of said lipid bilayer.

59. The delivery system complex of embodiment 58, wherein said biodegradable ionic precipitate forms a shell surrounding a core.

60. The delivery system complex of embodiment 59, wherein said shell has a thickness of about 4 nm to about 6 nm.

61. The delivery system complex of embodiment 59 or 60, wherein said core has a diameter of about 15 nm to about 20 nm.

62. The delivery system complex of any one of embodiments 59-61, wherein said core is an aqueous core.

63. The delivery system complex of any one of embodiments 58-62, wherein said biodegradable ionic precipitate is a calcium phosphate precipitate.

64. The delivery system complex of embodiment 63, wherein said inner leaflet comprises an amphiphilic lipid having a free phosphate group.

65. The delivery system complex of embodiment 64, wherein said amphiphilic lipid having a free phosphate group is dioleoyl phosphatidic acid (DOPA).

66. The delivery system complex of any one of embodiments 63-65, wherein said bioactive compound has a phosphate group.

67. The delivery system complex of any one of embodiments 58-66, wherein said bioactive compound comprises a water-soluble bioactive compound.

68. The delivery system complex of embodiment 67, wherein said water-soluble bioactive compound is a water-soluble chemotherapeutic drug.

69. The delivery system complex of embodiment 68, wherein said water-soluble chemotherapeutic drug is AraC monophosphate or gemcitabine monophosphate.

70. The delivery system complex of any one of embodiments 58-66, wherein said bioactive compound comprises a polynucleotide of interest or a polypeptide of interest.

71. The delivery system complex of embodiment 70, wherein said polynucleotide of interest comprises a silencing element, wherein expression or introduction of said silencing element into a cell reduces the expression of a target polynucleotide or the polypeptide encoded thereby.

72. The delivery system complex of embodiment 71, wherein said silencing element comprises an interfering RNA.

73. The delivery system complex of embodiment 72, wherein said interfering RNA comprises an siRNA.

74. The delivery system complex of embodiment 71, wherein said target polynucleotide comprises an oncogene.

75. The delivery system complex of any one of embodiments 58-74, wherein said outer leaflet comprises a neutral lipid.

76. The delivery system complex of embodiment 75, wherein said neutral lipid is dioleoyl phosphatidylcholine (DOPC).

77. The delivery system complex of any one of embodiments 58-76, wherein said outer leaflet comprises a lipid-polyethylene glycol (lipid-PEG) conjugate.

78. The delivery system complex of embodiment 77, wherein said lipid-PEG conjugate comprises a PEG molecule having a molecular weight of about 2000 g/mol.

79. The delivery system complex of embodiment 78, wherein said lipid-PEG conjugate comprises a 1,2-distearoyl-sn-glycero-3-phosphoethanolamine-N-carboxy-polyethylene glycol$_{2000}$ (DSPE-PEG$_{2000}$).

80. The delivery system complex of any one of embodiments 58-79, wherein said outer leaflet comprises a targeting ligand, thereby forming a targeted delivery system complex, wherein said targeting ligand targets said targeted delivery system complex to a targeted cell.

81. The delivery system complex of embodiment 80, wherein said targeting ligand comprises a benzamide derivative.

82. The delivery system complex of embodiment 81, wherein said benzamide derivative comprises anisamide.

83. The delivery system complex of embodiment 82, wherein said anisamide is conjugated to 1,2-distearoyl-sn-glycero-3-phosphoethanolamine-N-carboxy-polyethylene glycol (DSPE-PEG), thereby producing DSPE-PEG-AA.

84. The delivery system complex of any one of embodiments 80-83, wherein said targeted cell comprises a cancer cell.

85. The delivery system complex of embodiment 84, wherein said cancer is selected from the group consisting of a bladder cancer, a brain tumor, a breast cancer, a cervical cancer, a colorectal cancer, an esophageal cancer, an endometrial cancer, a hepatocellular carcinoma, a laryngeal cancer, a lung cancer, an osteosarcoma, an ovarian cancer, a pancreatic cancer, a prostate cancer, a renal cancer, and a thyroid cancer.

86. The delivery system complex of embodiment 85, wherein said cancer comprises a lung cancer.

87. The delivery system complex of any one of embodiments 58-86, wherein said delivery system complex has a diameter of less than about 100 nm.

88. The delivery system complex of embodiment 87, wherein said delivery system complex has a diameter of about 25 to about 30 nm.

89. The delivery system complex of any one of embodiments 58-88, wherein said delivery system complex has a zeta potential of about −17 mV.

90. A method of making a delivery system complex comprising a biodegradable ionic precipitate comprising a bioactive compound surrounded by a lipid bilayer comprising an inner and an outer leaflet, wherein said biodegradable ionic precipitate is ionically bound to the inner leaflet of said lipid bilayer, said method comprising:
  a) mixing a first reverse microemulsion comprising a cation and a second reverse microemulsion comprising an anion and an anionic lipid to form a biodegradable ionic precipitate, wherein said bioactive compound is within said first reverse microemulsion or said second reverse microemulsion;
  b) washing said biodegradable ionic precipitate;
  c) solubilizing said biodegradable ionic precipitate in a volatile, organic solvent to form a biodegradable ionic precipitate/solvent mixture;
  d) adding a lipid to the biodegradable ionic precipitate/solvent mixture; and
  e) evaporating said volatile, organic solvent to produce said delivery system complex.

91. The method of embodiment 90, wherein said cation is a calcium ion.

92. The method of embodiment 91, wherein said method further comprises producing said first reverse microemulsion.

93. The method of embodiment 92, wherein said producing said first reverse microemulsion comprises:
  a) providing an aqueous solution comprising calcium chloride; and
  b) mixing said aqueous solution comprising calcium chloride with a non-ionic surfactant and an organic solvent.

94. The method of embodiment 93, wherein said organic solvent comprises hexanol and cyclohexane.

95. The method of embodiment 94, wherein said organic solvent comprises cyclohexane and hexanol at a volume-to-volume ratio of about 78:11.

96. The method of any one of embodiments 93-95, wherein said non-ionic surfactant comprises Triton-X 100.

97. The method of embodiment 93, wherein said aqueous solution comprising calcium chloride is mixed with a solution of cyclohexane, hexanol, and Triton-X 100 at a volume/volume/volume ratio of about 78:11:11.

98. The method of any one of embodiments 90-97, wherein said anion is a phosphate ion.

99. The method of embodiment 98, wherein said method further comprises producing said second reverse microemulsion.

100. The method of embodiment 99, wherein said producing said second reverse microemulsion comprises:
  a) providing an aqueous solution comprising sodium phosphate; and
  b) mixing said aqueous solution comprising sodium phosphate with said anionic lipid, a non-ionic surfactant, and an organic solvent.

101. The method of embodiment 100, wherein said organic solvent comprises hexanol and cyclohexane.

102. The method of embodiment 101, wherein said organic solvent comprises cyclohexane and hexanol at a volume-to-volume ratio of about 78:11.

103. The method of any one of embodiments 100-102, wherein said non-ionic surfactant comprises Triton-X 100.

104. The method of embodiment 100, wherein said aqueous solution comprising sodium phosphate is mixed with said anionic lipid, and a solution of cyclohexane, hexanol, and Triton-X 100 at a volume/volume/volume ratio of about 78:11:11.

105. The method of any one of embodiments 93-104, wherein said anionic lipid is an amphiphilic lipid having a free phosphate group.

106. The method of embodiment 105, wherein said anionic lipid is dioleoyl phosphatidic acid.

107. The method of any one of embodiments 90-106, wherein said lipid added to the biodegradable ionic precipitate/solvent mixture is a neutral lipid.

108. The method of embodiment 107, wherein said neutral lipid comprises dioleoyl phosphatidylcholine.

109. The method of any one of embodiments 90-108, wherein said lipid comprises a lipid-polyethylene glycol (lipid-PEG) conjugate, a lipid-targeting ligand conjugate, or a combination thereof.

110. The method of embodiment 109, wherein said lipid-PEG conjugate comprises a PEG molecule having a molecular weight of about 2000 g/mol.

111. The method of embodiment 109, wherein said lipid-PEG conjugate comprises a 1,2-distearoyl-sn-glycero-3-phosphoethanolamine-N-carboxy-polyethylene glycol$_{2000}$ (DSPE-PEG$_{2000}$).

112. The method of embodiment 109, wherein said targeting ligand comprises a benzamide derivative.

113. The method of embodiment 112, wherein said benzamide derivative comprises anisamide.

114. The method of embodiment 113, wherein said anisamide is conjugated to 1,2-distearoyl-sn-glycero-3-phosphoethanolamine-N-carboxy-polyethylene glycol (DSPE-PEG), thereby producing DSPE-PEG-AA.

115. The method of any one of embodiments 109-114, wherein said lipid further comprises a neutral lipid, wherein said neutral lipid and said lipid-PEG conjugate, said lipid targeting ligand conjugate or a combination thereof is added to the biodegradable ionic precipitate/solvent mixture at a molar ratio of 10 neutral lipid to 1 lipid-PEG conjugate, lipid targeting ligand conjugate, or combination thereof.

116. The method of any one of embodiments 90-115, wherein said volatile, organic solvent is chloroform.

117. The method of any one of embodiments 90-116, wherein said biodegradable ionic precipitate is washed with ethanol.

118. The method of any one of embodiments 90-117, wherein said first reverse microemulsion has a pH of about 7.

119. The method of any one of embodiments 90-118, wherein said second reverse microemulsion has a pH of about 9.

120. A delivery system complex produced according to the method of any one of embodiments 90-119.

121. The method of embodiment 38, wherein said cation comprises calcium and wherein said anion comprises phosphate, and wherein said biodegradable ionic precipitate comprises a calcium phosphate precipitate.

122. The delivery system complex of embodiment 1, wherein said bioactive compound is gemcitabine monophosphate.

123. The method of any one of embodiments 31, 38 and 90, wherein said bioactive compound is gemcitabine monophosphate.

124. The method of any one of embodiments 38-40, wherein said organic solvent is nonpolar or essentially nonpolar.

These and other aspects of the invention are disclosed in more detail in the description of the invention given below.

BRIEF DESCRIPTION OF THE FIGURES

FIG. 7B measures the IC$_{50}$, the half maximal inhibitory concentration, of liposome/calcium phosphate-polyethylene glycol-anisamide (LCP-PEG-AA) nanoparticle and lipid/protamine/DNA-polyethylene glycol-anisamide (LPD-PEG-AA) nanoparticle formulations.

FIG. 14A formulation was DOTAP targeted with AA; FIG. 14B formulation was untargeted LCP-II and FIG. 14C formulation was AA-targeted LPD. Short arrows in FIG. 14A indicate spread and even distribution of fluorescently labeled dsDNA is evident. Long arrows in FIG. 14C indicate punctate distribution of dsDNA. Thus, the data indicate that LCP-II is capable of releasing more cargo to the cytoplasm than LPD.

DETAILED DESCRIPTION OF THE INVENTION

Figure 1:
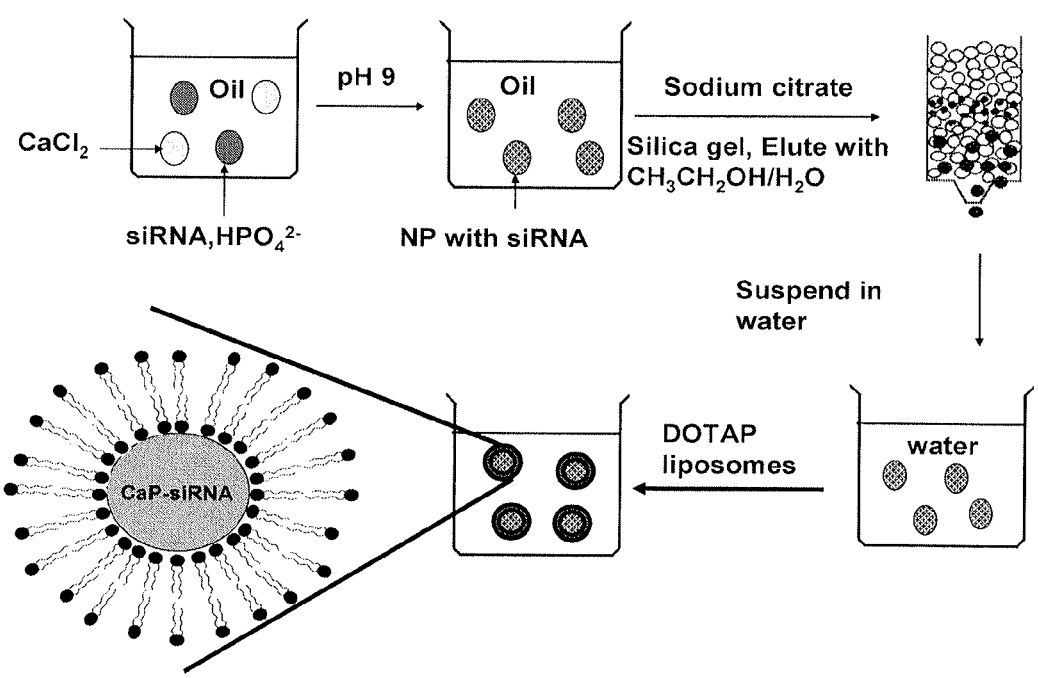
FIG. 1 illustrates the formation process of a non-limiting embodiment of the presently disclosed delivery system complexes. An aqueous solution comprising calcium chloride (CaCl$_2$), an aqueous solution comprising sodium phosphate (NaHPO4), and an aqueous solution comprising siRNA, surfactant, and an organic solvent (oil) are mixed to form a reaction solution. A calcium phosphate nanoprecipitate (NP) comprising the siRNA is formed in the resultant water-in-oil microemulsion. Sodium citrate is added to the microemulsion and the nanoprecipitate is purified on a silica gel column. The nanoprecipitate is eluted with a mixture of ethanol (CH$_3$CH$_2$OH) and water (H$_2$O) and suspended in water. The precipitate is mixed with DOTAP liposomes to form a delivery system complex comprising a liposome-encapsulated calcium phosphate (CaP)-siRNA precipitate.

Provided herein are delivery system complexes comprising a biodegradable precipitate comprising a bioactive compound, wherein the precipitate is encapsulated by a liposome. Further provided are delivery system complexes comprising a biodegradable ionic precipitate having a bioactive compound incorporated therein surrounded by a lipid bilayer, wherein the biodegradable ionic precipitate is ionically bound to the inner leaflet of the lipid bilayer. Methods for making the delivery system complexes as well as methods for the use of the complexes are further provided herein. The delivery system complexes can be used to deliver bioactive compounds to cells and to treat diseases or unwanted conditions in those embodiments wherein the bioactive compound comprised within the delivery system complex has therapeutic activity against the disease or unwanted condition.

As used herein, a "delivery system complex" or "delivery system" refer to a complex comprising a bioactive compound and a means for delivering the bioactive compound to a cell, physiological site, or tissue.

I. Liposome-encapsulated Biodegradable Ionic Precipitates and Methods of Making the Same The presently disclosed delivery system complexes can comprise a liposome that encapsulates a biodegradable ionic precipitate comprising the bioactive compound.

Liposomes are self-assembling, substantially spherical vesicles comprising a lipid bilayer that encircles a core, which can be aqueous, wherein the lipid bilayer comprises amphipathic lipids having hydrophilic headgroups and hydrophobic tails, in which the hydrophilic headgroups of the amphipathic lipid molecules are oriented toward the core or surrounding solution, while the hydrophobic tails orient toward the interior of the bilayer. The lipid bilayer structure thereby comprises two opposing monolayers that are referred to as the "inner leaflet" and the "outer leaflet," wherein the hydrophobic tails are shielded from contact with the surrounding medium. The "inner leaflet" is the monolayer wherein the hydrophilic head groups are oriented toward the core of the liposome. The "outer leaflet" is the monolayer comprising amphipathic lipids, wherein the hydrophilic head groups are oriented towards the outer surface of the liposome. Liposomes typically have a diameter ranging from about 25 nm to about 1 μm. (see, e.g., Shah (ed.) (1998) *Micelles, Microemulsions, and Monolayers: Science and Technology*, Marcel Dekker; Janoff (ed.) (1998) *Liposomes: Rational Design*, Marcel Dekker). The term "liposome" encompasses both multilamellar liposomes comprised of anywhere from two to hundreds of concentric lipid bilayers alternating with layers of an aqueous phase and unilamellar vesicles that are comprised of a single lipid bilayer. Methods for making liposomes are well known in the art and are described elsewhere herein.

As used herein, the term "lipid" refers to a member of a group of organic compounds that has lipophilic or amphipathic properties, including, but not limited to, fats, fatty oils, essential oils, waxes, steroids, sterols, phospholipids, glycolipids, sulpholipids, aminolipids, chromolipids (lipochromes), and fatty acids. The term "lipid" encompasses both naturally occurring and synthetically produced lipids. "Lipophilic" refers to those organic compounds that dissolve in fats, oils, lipids, and non-polar solvents, such as organic solvents. Lipophilic compounds are sparingly soluble or insoluble in water. Thus, lipophilic compounds are hydrophobic. Amphipathic lipids, also referred to herein as "amphiphilic lipids" refer to a lipid molecule having both hydrophilic and hydrophobic characteristics. The hydrophobic group of an amphipathic lipid, as described in more detail immediately herein below, can be a long chain hydrocarbon group. The hydrophilic group of an amphipathic lipid can include a charged group, e.g., an anionic or a cationic group, or a polar, uncharged group. Amphipathic lipids can have multiple hydrophobic groups, multiple hydrophilic groups, and combinations thereof. Because of the presence of both a hydrophobic group and a hydrophilic group, amphipathic lipids can be soluble in water, and to some extent, in organic solvents.

As used herein, "hydrophilic" is a physical property of a molecule that is capable of hydrogen bonding with a water ($H_2O$) molecule and is soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Conversely, the term "hydrophobic" is a physical property of a molecule that is repelled from a mass of water and can be referred to as "nonpolar," or "apolar," all of which are terms that can be used interchangeably with "hydrophobic." Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, dioleoyl phosphatidic acid, and dilinoleoylphosphatidylcholine. Other compounds lacking in phosphorus, such as sphingolipid, glycosphingolipid families, diacylglycerols and β-acyloxyacids, also are within the group designated as amphipathic lipids.

In some embodiments, the liposome or lipid bilayer comprises cationic lipids. As used herein, the term "cationic lipid" encompasses any of a number of lipid species that carry a net positive charge at physiological pH, which can be determined using any method known to one of skill in the art. Such lipids include, but are not limited to, the cationic lipids of formula (I) disclosed in International Application No. PCT/US2009/042476, entitled "Methods and Compositions Comprising Novel Cationic Lipids," which was filed on May 1, 2009, and is herein incorporated by reference in its entirety. These include, but are not limited to, N-methyl-N-(2-(arginoylamino)ethyl)-N,N-Di octadecyl aminium chloride or di stearoyl arginyl ammonium chloride]

(DSAA), N,N-di-myristoyl-N-methyl-N-2[N'—(N$^6$-guanidino-L-lysinyl)]aminoethyl ammonium chloride (DMGLA), N,N-dimyristoyl-N-methyl-N-2[N$^2$-guanidino-L-lysinyl] aminoethyl ammonium chloride, N,N-dimyristoyl-N-methyl-N-2[N'—(N2,N6-di-guanidino-L-lysinyl)]aminoethyl ammonium chloride, and N,N-di-stearoyl-N-methyl-N-2[N'—(N6-guanidino-L-lysinyl)]aminoethyl ammonium chloride (DSGLA). Other non-limiting examples of cationic lipids that can be present in the liposome or lipid bilayer of the presently disclosed delivery system complexes include N,N-dioleyl-N,N-dimethylammonium chloride ("DODAC"); N-(2,3-dioleoyloxy)propyl)-N,N,N-trimethylammonium chloride ("DOTAP"); N-(2,3-dioleyloxy)propyl)-N,N,N-trimethylammonium chloride ("DOTMA") or other N—(N,N-1-dialkoxy)-alkyl-N,N,N-trisubstituted ammonium surfactants; N,N-distearyl-N,N-dimethylammonium bromide ("DDAB"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"); 1,3-dioleoyl-3-trimethylammonium-propane, N-(1-(2,3-dioleyloxy)propyl)-N-(2-(sperminecarboxamido)ethyl)-N,N-dimethyl-1 ammonium trifluoro-acetate (DOSPA); GAP-DLRIE; DMDHP; 3-β[$^4$N—($^1$N,$^8$N-diguanidino spermidine)-carbamoyl]cholesterol (BGSC); 3-β[N,N-diguanidinoethyl-aminoethane)-carbamoyl]cholesterol (BGTC); N,N$^1$,N$^2$,N$^3$ Tetra-methyltetrapalmityl-spermine (cellfectin); N-t-butyl-N'-tetradecyl-3-tetradecyl-aminopropion-amidine (CLONfectin); dimethyldioctadecyl ammonium bromide (DDAB); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3 dioleoyloxy-1,4-butanediammonium iodide) (Tfx-50); 1,2 dioleoyl-3-(4'-trimethylammonio) butanol-sn-glycerol (DOBT) or cholesteryl (4' trimethylammonia) butanoate (ChOTB) where the trimethylammonium group is connected via a butanol spacer arm to either the double chain (for DOTB) or cholesteryl group (for ChOTB); DL-1,2-dioleoyl-3-dimethylaminopropyl-β-hydroxyethylammonium (DORI) or DL-1,2-O-dioleoyl-3-dimethylaminopropyl-β-hydroxyethylammonium (DORIE) or analogs thereof as disclosed in International Application Publication No. WO 93/03709, which is herein incorporated by reference in its entirety; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185, which is herein incorporated by reference in its entirety; cholesteryl-3β-carboxyl-amido-ethylenetrimethylammonium iodide; 1-dimethylamino-3-trimethylammonio-DL-2-propyl-cholesteryl carboxylate iodide; cholesteryl-3-β-carboxyamidoethyleneamine; cholesteryl-3-β-oxysuccinamido-ethylenetrimethylammonium iodide; 1-dimethylamino-3-trimethylammonio-DL-2-propyl-cholesteryl-3-β-oxysuccinate iodide; 2-(2-trimethylammonio)-ethylmethylamino ethyl-cholesteryl-3-β-oxysuccinate iodide; and 3-β-N-(polyethyleneimine)-carbamoylcholesterol.

In some embodiments, the liposomes or lipid bilayers can contain co-lipids that are negatively charged or neutral. As used herein, a "co-lipid" refers to a non-cationic lipid, which includes neutral (uncharged) or anionic lipids. The term "neutral lipid" refers to any of a number of lipid species that exist either in an uncharged or neutral zwitterionic form at physiological pH. The term "anionic lipid" encompasses any of a number of lipid species that carry a net negative charge at physiological pH. Co-lipids can include, but are not limited to, diacylphosphatidylcholine, diacylphosphatidylethanolamine, ceramide, sphingomyelin, cephalin, cholesterol, cerebrosides and diacylglycerols, phospholipid-related materials, such as lecithin, phosphatidylethanolamine, lysolecithin, lysophosphatidylethanolamine, phosphatidylserine, phosphatidylinositol, cardiolipin, phosphatidic acid, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), palmitoyloleyolphosphatidylglycerol (POPG), dipalmitoylphosphatidylglycerol (DPPG), dioleoyl-phosphatidylethanolamine (DOPE), palmitoyloleoylphosphatidylchol-ine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dioleoyl phosphatidic acid (DOPA), stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, lysophosphatidylcholine, and dioctadecyldimethyl ammonium bromide and the like. Co-lipids also include polyethylene glycol-based polymers such as PEG 2000, PEG 5000 and polyethylene glycol conjugated to phospholipids or to ceramides, as described in U.S. Pat. No. 5,820,873, herein incorporated by reference in its entirety.

In some embodiments, the liposome of the delivery system complex is a cationic liposome and in other embodiments, the liposome is anionic. The term "cationic liposome" as used herein is intended to encompass any liposome as defined above which has a net positive charge or has a zeta potential of greater than 0 mV at physiological pH. Alternatively, the term "anionic liposome" refers to a liposome as defined above which has a net negative charge or a zeta potential of less than 0 mV at physiological pH. The zeta potential or charge of the liposome can be measured using any method known to one of skill in the art. It should be noted that the liposome itself is the entity that is being determined as cationic or anionic, meaning that the liposome that has a measurable positive charge or negative charge at physiological pH, respectively, can, within an in vivo environment, become attached to other substances or may be associated with other charged components within the aqueous core of the liposome, which can thereby result in the formation of a structure that does not have a net charge. After a delivery system complex comprising a cationic or anionic liposome is produced, molecules such as lipid-PEG conjugates can be post-inserted into the bilayer of the liposome as described elsewhere herein, thus shielding the surface charge of the delivery system complex.

In those embodiments in which the liposome of the delivery system complex is a cationic liposome, the cationic liposome need not be comprised completely of cationic lipids, however, but must be comprised of a sufficient amount of cationic lipids such that the liposome has a positive charge at physiological pH. The cationic liposomes also can contain co-lipids that are negatively charged or neutral, so long as the net charge of the liposome is positive and/or the surface of the liposome is positively charged at physiological pH. In these embodiments, the ratio of cationic lipids to co-lipids is such that the overall charge of the resulting liposome is positive at physiological pH. For example, cationic lipids are present in the cationic liposome at from about 10 mole % to about 100 mole % of total liposomal lipid, in some embodiments, from about 20 mole % to about 80 mole % and, in other embodiments, from about 20 mole % to about 60 mole %. Neutral lipids, when included in the cationic liposome, can be present at a concentration of from about 0 mole % to about 90 mole % of the total liposomal lipid, in some embodiments from about 20 mole % to about 80 mole %, and in other embodiments, from about 40 mole % to about 80 mole %. Anionic lipids, when included in the cationic liposome, can be present at a concentration ranging from about 0 mole % to about 49 mole % of the total liposomal lipid, and in certain embodiments, from about 0 mole % to about 40 mole %.

In some embodiments, the cationic liposome of the delivery system complex comprises a cationic lipid and the neutral co-lipid cholesterol at a 1:1 molar ratio. In some of these embodiments, the cationic lipid comprises DOTAP.

Likewise, in those embodiments in which the liposome of the delivery system complex is an anionic liposome, the anionic liposome need not be comprised completely of anionic lipids, however, but must be comprised of a sufficient amount of anionic lipids such that the liposome has a negative charge at physiological pH. The anionic liposomes also can contain neutral co-lipids or cationic lipids, so long as the net charge of the liposome is negative and/or the surface of the liposome is negatively charged at physiological pH. In these embodiments, the ratio of anionic lipids to neutral co-lipids or cationic lipids is such that the overall charge of the resulting liposome is negative at physiological pH. For example, the anionic lipid is present in the anionic liposome at from about 10 mole % to about 100 mole % of total liposomal lipid, in some embodiments, from about 20 mole % to about 80 mole % and, in other embodiments, from about 20 mole % to about 60 mole %. The neutral lipid, when included in the anionic liposome, can be present at a concentration of from about 0 mole % to about 90 mole % of the total liposomal lipid, in some embodiments from about 20 mole % to about 80 mole %, and in other embodiments, from about 40 mole % to about 80 mole %. The positively charged lipid, when included in the anionic liposome, can be present at a concentration ranging from about 0 mole % to about 49 mole % of the total liposomal lipid, and in certain embodiments, from about 0 mole % to about 40 mole %.

In some embodiments in which the lipid vehicle is a cationic liposome or an anionic liposome, the delivery system complex as a whole has a net positive charge. By "net positive charge" is meant that the positive charges of the components of the delivery system complex (e.g., cationic lipid of liposome, cation of precipitate, cationic bioactive compound) exceed the negative charges of the components of the delivery system complex (e.g., anionic lipid of liposome, anion of precipitate, anionic bioactive compound). It is to be understood, however, that the present invention also encompasses delivery system complexes having a positively charged surface irrespective of whether the net charge of the complex is positive, neutral or even negative. The charge of the surface of a delivery system complex can be measured by the migration of the complex in an electric field by methods known to those in the art, such as by measuring zeta potential (Martin, Swarick, and Cammarata (1983) Physical Pharmacy & Physical Chemical Principles in the Pharmaceutical Sciences, 3rd ed. Lea and Febiger) or by the binding affinity of the delivery system complex to cell surfaces. Complexes exhibiting a positively charged surface have a greater binding affinity to cell surfaces than complexes having a neutral or negatively charged surface. Further, it is to be understood that the positively charged surface can be sterically shielded by the addition of non-ionic polar compounds, for example, polyethylene glycol, as described elsewhere herein.

In particular non-limiting embodiments, the delivery system complex has a charge ratio of positive to negative charge (+: −) of between about 0.5:1 and about 100:1, including but not limited to about 0.5:1, about 1:1, about 2:1, about 3:1, about 4:1, about 5:1, about 6:1, about 7:1, about 8:1, about 9:1, about 10:1, about 15:1, about 20:1, about 40:1, or about 100:1. In a specific non-limiting embodiment, the +: − charge ratio is about 1:1.

The presently disclosed delivery system complexes can comprise liposomes that encapsulate a biodegradable ionic precipitate comprising a bioactive compound, that is, the biodegradable ionic precipitate is present in the core of the liposome. As used herein an "ionic precipitate" refers to a solid molecular complex, wherein the molecules of the complex are held together via ionic interactions. A "biodegradable ionic precipitate" is an ionic precipitate wherein the ionic interactions between the molecules of the precipitate are sensitive to intracellular pH conditions within a cell or a cellular organelle such that the ionic interactions between the molecules of the precipitate are interrupted and the precipitate readily dissolves into individual ions. While not being bound by any particular theory or mechanism of action, it is believed the presently disclosed delivery system complexes enter cells through endocytosis and are found in endosomes, which exhibit a relatively low pH (e.g., pH 5.0). Thus, in some embodiments, the biodegradable ionic precipitate readily dissolves at endosomal pH. In certain embodiments, the biodegradable ionic precipitate readily dissolves at a pH level of less than about 6.5, less than about 6.0, less than about 5.5, less than about 5.0, less than about 4.5, or less than about 4.0, including but not limited to, about 6.5, about 6.4, about 6.3, about 6.2, about 6.1, about 6.0, about 5.9, about 5.8, about 5.7, about 5.6, about 5.5, about 5.4, about 5.3, about 5.2, about 5.1, about 5.0, about 4.9, about 4.8, about 4.7, about 4.6, about 4.5, about 4.4, about 4.3, about 4.2, about 4.1, about 4.0, or less. In particular embodiments, the biodegradable ionic precipitate readily dissolves at a pH of 5.0 or less. In a preferred embodiment, a LCP-II nanoparticle comprises an acid-sensitive core. An acid-sensitive core dissolves more readily at pH levels below 7. In these embodiments, the LCP-II nanoparticle can unload more cargo at the target, e.g. the cytoplasm, than a nanoparticle formulated without an acid-sensitive core.

The biodegradable ionic precipitate can be comprised of any ions (pairs of cations and ions), but in particular embodiments, the precipitate comprises at least one of a divalent cation, a trivalent cation, a divalent anion, or a trivalent anion. In some of these embodiments, the ionic precipitate comprises a divalent cation and a divalent anion and in other embodiments, a trivalent cation and a trivalent anion. In particular embodiments, the divalent cation comprises calcium, magnesium, or manganese. Non-limiting examples of biodegradable ionic precipitates that can be comprised within the presently disclosed delivery system complexes include calcium phosphate, calcium citrate, calcium carbonate, magnesium carbonate, magnesium phosphate, and manganous phosphate. In certain embodiments, the biodegradable ionic precipitate comprises calcium phosphate.

The delivery system complexes can be of any size, so long as the complex is capable of delivering the incorporated bioactive compound to a cell (e.g., in vitro, in vivo), physiological site, or tissue. In some embodiments, the delivery system complex comprises a nanoparticle, wherein the nanoparticle comprises a liposome encapsulating a biodegradable nanoprecipitate comprising a bioactive compound. As used herein, the term "nanoparticle" refers to particles of any shape having at least one dimension that is less than about 1000 nm. In some embodiments, nanoparticles have at least one dimension in the range of about 1 nm to about 1000 nm, including any integer value between 1 nm and 1000 nm (including about 1, 2, 5, 10, 20, 30, 40, 50, 60, 70, 80, 90, 100, 200, 500, and 1000). In certain embodiments, the nanoparticles have at least one dimension that is about 150 nm. Particle size can be determined using any method known in the art, including, but not limited to, sedimentation field flow fractionation, photon correlation spectroscopy, disk centrifugation, and dynamic light scattering (using, for example, a submicron particle sizer such as the NICOMP particle sizing system from AutodilutePAT Model 370; Santa Barbara, Calif.).

As described elsewhere herein, the size of the delivery system complex can be regulated based on the ratio of non-ionic surfactant to organic solvent used during the generation of the water-in-oil microemulsion that comprises the biodegradable ionic precipitate. Further, the size of the delivery system complexes is dependent upon the ratio of the lipids in the liposome to the biodegradable ionic precipitate and bioactive compound.

Nanoparticles comprising liposomes encapsulating calcium phosphate nanoprecipitates comprising bioactive compounds are referred to herein as "liposome/calcium phosphate nanoparticles" or "LCP nanoparticles."

The presently disclosed delivery system complexes can be made by mixing a prepared liposome with an aqueous solution of a biodegradable ionic precipitate comprising a bioactive compound. In order for the liposome and biodegradable ionic precipitate to associate with one another, ionic interactions may be utilized, wherein the liposome comprises a cationic liposome and the biodegradable ionic precipitate has a negatively charged surface. Alternatively, the liposome can comprise an anionic liposome and the biodegradable ionic precipitate can have a positively charged surface.

Methods for preparing liposomes are known in the art. For example, a review of methodologies of liposome preparation may be found in *Liposome Technology* (CFC Press NY 1984); *Liposomes* by Ostro (Marcel Dekker, 1987); Lichtenberg and Barenholz (1988) *Methods Biochem Anal.* 33:337-462 and U.S. Pat. No. 5,283,185, each of which are herein incorporated by reference in its entirety. For example, cationic lipids and optionally co-lipids can be emulsified by the use of a homogenizer, lyophilized, and melted to obtain multilamellar liposomes. Alternatively, unilamellar liposomes can be produced by the reverse phase evaporation method (Szoka and Papahadjopoulos (1978) *Proc. Natl. Acad. Sci. USA* 75:4194-4198, which is herein incorporated by reference in its entirety). In some embodiments, the liposomes are produced using thin film hydration (Bangham et al. (1965) *J. Mol. Biol.* 13:238-252, which is herein incorporated by reference in its entirety). In certain embodiments, the liposome formulation can be briefly sonicated and incubated at 50° C. for a short period of time (e.g., about 10 minutes) prior to sizing (see Templeton et al. (1997) *Nature Biotechnology* 15:647-652, which is herein incorporated by reference in its entirety).

In some embodiments, the prepared liposome can be sized prior to its addition to the biodegradable ionic precipitate, wherein the liposomes are selected from a population of liposomes based on the size (e.g., diameter) of the liposomes. The liposomes can be sized using techniques such as ultrasonication, high-speed homogenization, and pressure filtration (Hope et al. (1985) *Biochimica et Biophysica Acta* 812:55; U.S. Pat. Nos. 4,529,561 and 4,737,323, each of which are herein incorporated by reference in its entirety). Sonicating a liposome either by bath or probe sonication produces a progressive size reduction down to small vesicles less than about 0.05 microns in size. Vesicles can be recirculated through a standard emulsion homogenizer to the desired size, typically between about 0.1 microns and about 0.5 microns. The size of the liposomes can be determined by quasi-elastic light scattering (QELS) (Bloomfield (1981) *Ann. Rev. Biophys. Bioeng.* 10:421-450). The average diameter can be reduced by sonication of the liposomes. Intermittent sonication cycles can be alternated with QELS assessment to guide efficient liposome synthesis. Alternatively, liposomes can be extruded through a small-pore polycarbonate membrane or an asymmetric ceramic membrane to yield a well-defined size distribution. Typically, a suspension is cycled through the membrane one or more times until the desired size distribution is achieved. The complexes can be extruded through successively smaller-pore membranes, to achieve a gradual reduction in size. In particular embodiments, the liposomes are extruded through a membrane having a pore size of about 100 nm.

The method of making a presently disclosed delivery system complex can further comprise making the aqueous solution comprising the biodegradable ionic precipitate comprising a bioactive compound. These methods can comprise mixing an aqueous solution (i.e., a solution comprising water) comprising an anion, an aqueous solution comprising a cation, an aqueous solution comprising a bioactive compound, a non-ionic surfactant, and an organic solvent, thereby producing a water-in-oil microemulsion comprising the biodegradable ionic precipitate. In order to form the water-in-oil microemulsion, the cation, anion, and bioactive compound solutions must be added separately to the resulting reaction solution. It should be noted, however, that the surfactant and organic solvent can be premixed prior to the addition of the mixture to the reaction solution.

An emulsion is a dispersion of one liquid in a second immiscible liquid. The term "immiscible" when referring to two liquids refers to the inability of these liquids to be mixed or blended into a homogeneous solution. Two immiscible liquids when added together will always form two separate phases. The organic solvent used in the presently disclosed methods is essentially immiscible with water. Emulsions are essentially swollen micelles, although not all micellar solutions can be swollen to form an emulsion. Micelles are colloidal aggregates of amphipathic molecules that are formed at a well-defined concentration known as the critical micelle concentration. Micelles are oriented with the hydrophobic portions of the lipid molecules at the interior of the micelle and the hydrophilic portions at the exterior surface, exposed to water. The typical number of aggregated molecules in a micelle (aggregation number) has a range from about 50 to about 100. The term "micelles" also refers to inverse or reverse micelles, which are formed in an organic solvent, wherein the hydrophobic portions are at the exterior surface, exposed to the organic solvent and the hydrophilic portion is oriented towards the interior of the micelle.

An oil-in-water (O/W) emulsion consists of droplets of an organic compound (e.g., oil) dispersed in water and a water-in-oil (W/O) emulsion is one in which the phases are reversed and is comprised of droplets of water dispersed in an organic compound (e.g., oil). A water-in-oil emulsion is also referred to herein as a reverse emulsion. Thermodynamically stable emulsions are those that comprise a surfactant (e.g, an amphipathic molecule) and are formed spontaneously. The term "emulsion" can refer to microemulsions or macroemulsions, depending on the size of the particles. Droplet diameters in microemulsions typically range from about 10 to about 100 nm. In contrast, the term macroemulsions refers to droplets having diameters greater than about 100 nm.

It will be evident to one of skill in the art that sufficient amounts of the aqueous solutions, organic solvent, and surfactants are added to the reaction solution to form the water-in-oil emulsion.

The aqueous solution comprising a cation and the aqueous solution comprising an anion may comprise ionic complexes (e.g., calcium chloride, sodium phosphate), wherein the pH of the solution has been adjusted in order to enhance the dissociation of the ionic complexes into free ions and to therefore, facilitate the interaction of the free cations and anions within the reaction solution in order to produce the biodegradable ionic precipitate. In some embodiments, the cation complex comprises calcium chloride and the anion complex comprises sodium phosphate and the pH of the two solutions is adjusted to a pH of 9.

Surfactants are added to the reaction solution in order to facilitate the development of and stabilize the water-in-oil microemulsion. Surfactants are molecules that can reduce the surface tension of a liquid. Surfactants have both hydrophilic and hydrophobic properties, and thus, can be solubilized to some extent in either water or organic solvents. Surfactants are classified into four primary groups: cationic, anionic, non-ionic, and zwitterionic. The presently disclosed methods use non-ionic surfactants. Non-ionic surfactants are those surfactants that have no charge when dissolved or dispersed in aqueous solutions. Thus, the hydrophilic moieties of non-ionic surfactants are uncharged, polar groups. Representative non-limiting examples of non-ionic surfactants suitable for use for the presently disclosed methods and compositions include polyethylene glycol, polysorbates, including but not limited to, polyethoxylated sorbitan fatty acid esters (e.g., Tween® compounds) and sorbitan derivatives (e,g., Span® compounds); ethylene oxide/propylene oxide copolymers (e.g., Pluronic® compounds, which are also known as poloxamers); polyoxyethylene ether compounds, such as those of the Brij® family, including but not limited to polyoxyethylene stearyl ether (also known as polyoxyethylene (100) stearyl ether and by the trade name Brij® 700); ethers of fatty alcohols. In particular embodiments, the non-ionic surfactant comprises octyl phenol ethoxylate (i.e., Triton X-100), which is commercially available from multiple suppliers (e.g., Sigma-Aldrich, St. Louis, Mo.).

Polyethoxylated sorbitan fatty acid esters (polysorbates) are commercially available from multiple suppliers (e.g., Sigma-Aldrich, St Louis, Mo.) under the trade name Tween®, and include, but are not limited to, polyoxyethylene (POE) sorbitan monooleate (Tween® 80), POE sorbitan monostearate (Tween® 60), POE sorbitan monolaurate (Tween® 20), and POE sorbitan monopalmitate (Tween® 40).

Ethylene oxide/propylene oxide copolymers include the block copolymers known as poloxamers, which are also known by the trade name Pluronic® and can be purchased from BASF Corporation (Florham Park, N.J.). Poloxamers are composed of a central hydrophobic chain of polyoxypropylene (poly(propylene oxide)) flanked by two hydrophilic chains of polyoxyethylene (poly(ethylene oxide)) and are represented by the following chemical structure: $HO(C_2H_4O)_a(C_3H_6O)_b(C_2H_4O)_aH$; wherein the C2H4O subunits are ethylene oxide monomers and the C3H6O subunits are propylene oxide monomers, and wherein a and b can be any integer ranging from 20 to 150.

Organic solvents that can be used in the presently disclosed methods include those that are immiscible or essentially immiscible with water. Non-limiting examples of organic solvents that can be used in the presently disclosed methods include chloroform, methanol, ether, ethyl acetate, hexanol, cyclohexane, and dichloromethane. In particular embodiments, the organic solvent is nonpolar or essentially nonpolar.

In some embodiments, mixtures of more than one organic solvent can be used in the presently disclosed methods. In some of these embodiments, the organic solvent comprises a mixture of cyclohexane and hexanol. In particular embodiments, the organic solvent comprises cyclohexane and hexanol at a volume/volume ratio of about 7.5:1.7. As noted elsewhere herein, the non-ionic surfactant can be added to the reaction solution (comprising aqueous solutions of cation, anion, bioactive compound, and organic solvent) separately, or it can first be mixed with the organic solvent and the organic solvent/surfactant mixture can be added to the aqueous solutions of the anion, cation, and bioactive compound. In some of these embodiments, a mixture of cyclohexane, hexanol, and Triton X-100 is added to the reaction solution. In particular embodiments, the volume/volume/volume ratio of the cyclohexane:hexanol:Triton X-100 of the mixture that is added to the reaction solution is about 7.5:1.7:1.8.

In those embodiments wherein the biodegradable ionic precipitate comprises calcium phosphate, methods for making the biodegradable calcium phosphate precipitate can comprise mixing an aqueous solution of calcium chloride, an aqueous solution of sodium phosphate, an aqueous solution of the bioactive compound, a non-ionic surfactant, and an organic solvent. In some of these embodiments, the calcium chloride is at a concentration of about 250 mM in the aqueous solution and the sodium phosphate is at a concentration of about 250 mM in the aqueous solution. The pH levels of the two aqueous solutions can be adjusted to pH 9.0, for example, with 1 M ammonium. In some of these embodiments, 150 µl of the 250 mM calcium chloride solution and 100 µl of the sodium phosphate solution are mixed in a total volume of reaction solution of about 7 ml. In particular embodiments, the 7 ml reaction solution comprises about 7 ml of cyclohexane/hexanol/Triton X-100 at a 7.5:1.7:1.8 volume/volume/volume ratio.

It should be noted that the volume/volume ratio of the nonionic surfactant to the organic solvent regulates the size of the water-in-oil microemulsion and therefore, the biodegradable ionic precipitate contained therein and the resultant delivery system complex, with a greater surfactant:organic solvent ratio resulting in delivery system complexes with larger diameters and smaller surfactant:organic solvent ratios resulting in delivery system complexes with smaller diameters.

The reaction solution may be mixed to form the water-in-oil microemulsion and the solution may also be incubated for a period of time. This incubation step can be performed at room temperature. In some embodiments, the reaction solution is mixed at room temperature for a period of time of between about 5 minutes and about 60 minutes, including but not limited to about 5 minutes, about 10 minutes, about 15 minutes, about 20 minutes, about 25 minutes, about 30 minutes, about 35 minutes, about 40 minutes, about 45 minutes, about 50 minutes, about 55 minutes, and about 60 minutes. In particular embodiments, the reaction solution is mixed at room temperature for about 15 minutes.

In order to complex the biodegradable ionic precipitate with a liposome, the surface of the biodegradable ionic precipitate can be charged, either positively or negatively. In some embodiments, the biodegradable ionic precipitate will have a charged surface following its formation. Those precipitates with positively charged surfaces can be mixed with anionic liposomes, whereas those precipitates with negatively charged surfaces can be mixed with cationic liposomes.

In certain embodiments, the surface charge of the biodegradable ionic precipitate can be enhanced or reversed using any method known in the art. For example, a biodegradable ionic precipitate having a positively charged surface can be modified to create a negatively charged surface. Alternatively, a biodegradable ionic precipitate having a negatively charged surface can be modified to create a positively charged surface.

In those embodiments wherein a biodegradable ionic precipitate is created having a positive surface charge, the surface charge can be made negative through the addition of sodium citrate to the water-in-oil microemulsion. In some embodiments, sodium citrate is added at a concentration of about 15 mM to the microemulsion. In some of these embodiments, the total volume of the 15 mM sodium citrate added to the microemulsion is about 125 µl. Sodium citrate is especially useful for imparting a negative surface charge to the precipitates because it is non-toxic.

In some embodiments, the biodegradable ionic precipitate has or is modified to have a zeta potential of less than −10 mV and in certain embodiments, the zeta potential is between about −14 mV and about −20 mV, including but not limited to about −14 mV, about −15 mV, about −16 mV, about −17 mV, about −18 mV, about −19 mV, and about −20 mV. In particular embodiments, the zeta potential of the precipitate is about −16 mV.

In those embodiments wherein the biodegradable ionic precipitate has a negatively charged surface, a cationic liposome is complexed with the precipitate. The ratio of the cationic liposome to the biodegradable ionic precipitate, and/or the bioactive compound can regulate the size and charge of the resultant delivery system complex (see FIG. 4). In those embodiments wherein the bioactive compound comprises a polynucleotide and the zeta potential of the biodegradable precipitate is about −16 mV, and wherein the liposome comprises a 1:1 molar ratio of DOTAP:cholesterol, a molar ratio of total lipids/polynucleotide of about 973 is used to produce delivery system complexes having a zeta potential of about +40 mV and an average diameter of about 150 nm. In preferred embodiments, the zeta potential of a nanoparticle comprising a liposome is different than the zeta potential of a pure liposome containing the pure lipid, whether the zeta potential is a positive or negative value. In this aspect, it is preferred that the nanoparticle is a lipid-coated LCP-II composition. In other words, preferably, the LCP-II formulation comprises an outer leaflet comprised of different lipids rather than a single, relatively pure lipid. This also referred to herein as an asymmetric lipid membrane. The asymmetric lipid membrane can shield the charges that would be present on a pure liposome. Preferably, a positive zeta potential is of a lower value than the pure liposome. Preferred zeta potentials of nanoparticles, particularly LCP-II nanoparticles, are from about +1 mV to about +40 mV. More preferably, the zeta potential is from about +5 mV to about +25 mV.

Following the production of the water-in-oil emulsion, the biodegradable ionic precipitate is purified from the non-ionic surfactant and organic solvent. The biodegradable ionic precipitate can be purified using any method known in the art, including but not limited to gel filtration chromatography. A biodegradable ionic precipitate that has been purified from the non-ionic surfactants and organic solvent is a precipitate that is essentially free of non-ionic surfactants or organic solvents (e.g, the precipitate comprises less than 10%, less than 1%, less than 0.1% by weight of the non-ionic surfactant or organic solvent). In some of those embodiments wherein gel filtration is used to purify the biodegradable ionic precipitate, the precipitate is adsorbed to a silica gel or to a similar type of a stationary phase, the silica gel or similar stationary phase is washed with a polar organic solvent (e.g., ethanol, methanol, acetone, DMSO, DMF) to remove the non-ionic surfactant and organic solvent, and the biodegradable ionic precipitate is eluted from the silica gel or other solid surface with an aqueous solution comprising a polar organic solvent.

In some of these embodiments, the silica gel is washed with ethanol and the biodegradable ionic precipitate is eluted with a mixture of water and ethanol. In particular embodiments, the precipitate is eluted with a mixture of water and ethanol, wherein the mixture comprises a volume/volume ratio of between about 1:9 and about 1:1, including but not limited to, about 1:9, about 1:8, about 1:7, about 1:6, about 1:5, about 1:4, about 1:3, about 1:2, and about 1:1. In particular embodiments, the volume/volume ratio of water to ethanol is about 1:3. In some of these embodiments, a mixture comprising 25 ml water and 75 ml ethanol is used for the elution step. Following removal of the ethanol using, for example, rotary evaporation, the biodegradable ionic precipitate can be dispersed in an aqueous solution (e.g., water) prior to mixing with the prepared liposomes.

In certain embodiments, the methods of making the delivery system complexes can further comprise an additional purification step following the production of the delivery system complexes, wherein the delivery system complexes are purified from excess free liposomes and unencapsulated precipitates. Purification can be accomplished through any method known in the art, including, but not limited to, centrifugation through a sucrose density gradient or other media which is suitable to form a density gradient. It is understood, however, that other methods of purification such as chromatography, filtration, phase partition, precipitation or absorption can also be utilized. In one method, purification via centrifugation through a sucrose density gradient is utilized. The sucrose gradient can range from about 0% sucrose to about 60% sucrose or from about 5% sucrose to about 30% sucrose. The buffer in which the sucrose gradient is made can be any aqueous buffer suitable for storage of the fraction containing the complexes and in some embodiments, a buffer suitable for administration of the complex to cells and tissues.

In some embodiments, a targeted delivery system or a PEGylated delivery system is made as described elsewhere herein, wherein the methods further comprise a post-insertion step following the preparation of the liposome or following the production of the delivery system complex, wherein a lipid-targeting ligand conjugate or a PEGylated lipid is post-inserted into the liposome. Liposomes or delivery system complexes comprising a lipid-targeting ligand conjugate or a lipid-PEG conjugate can be prepared following techniques known in the art, including but not limited to those presented herein (see Experimental section; Ishida et al. (1999) *FEBS Lett.* 460:129-133; Perouzel et al. (2003) *Bioconjug. Chem.* 14:884-898, which is herein incorporated by reference in its entirety). The post-insertion step can comprise mixing the liposomes or the delivery system complexes with the lipid-targeting ligand conjugate or a lipid-PEG conjugate and incubating the particles at about 50° C. to about 60° C. for a brief period of time (e.g., about 5 minutes, about 10 minutes). In some embodiments, the delivery system complexes or liposomes are incubated with a lipid-PEG conjugate or a lipid-PEG-targeting ligand conjugate at a concentration of about 5 to about 20 mol %, including but not limited to about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, and about 20 mol %, to form a stealth delivery system. In some of these embodiments, the concentration of the lipid-PEG conjugate is about 10 mol %. The polyethylene glycol moiety of the lipid-PEG conjugate can have a molecular weight ranging from about 100 to about 20,000 g/mol, including but not limited to about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 5000 g/mol, about 10,000 g/mol, about 15,000 g/mol, and about 20,000 g/mol. In certain embodiments, the lipid-PEG conjugate comprises a PEG molecule having a molecular weight of about 2000 g/mol. In some embodiments, the lipid-PEG conjugate comprises DSPE-PEG$_{2000}$. Lipid-PEG-targeting ligand conjugates can also be post-inserted into liposomes or delivery system complexes using the above described post-insertion methods.

II. Delivery System Complexes Having a Biodegradable Ionic Precipitate Ionically Bound to a Surrounding Lipid Bilayer and Methods of Making the Same Delivery system complexes comprising a biodegradable ionic precipitate comprising a bioactive compound surrounded by a lipid bilayer comprising an inner and an outer leaflet, wherein the biodegradable ionic precipitate is ionically bound to the inner leaflet of the lipid bilayer are provided. In some embodiments, the biodegradable ionic precipitate forms a shell surrounding a core. In some embodiments, the thickness of the biodegradable ionic precipitate shell is between about 1 nm and about 100 nm, including but not limited to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 nm. In particular embodiments, the thickness of the biodegradable ionic precipitate shell is about 4 nm to about 6 nm. In some embodiments, the core surrounded by the biodegradable ionic precipitate shell can have a diameter of about 1 nm to about 100 nm, including but not limited to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 nm. In particular embodiments, the core has a diameter of about 15 nm to about 20 nm. In certain embodiments, the core is an aqueous core.

The delivery system complex comprising a biodegradable ionic precipitate comprising a bioactive compound surrounded by a lipid bilayer comprising an inner and an outer leaflet, wherein the biodegradable ionic precipitate is ionically bound to the inner leaflet of the lipid bilayer can have a diameter of less than about 100 nm, including but not limited to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, and 100 nm. In particular embodiments, the delivery system complex has a diameter of about 25 to about 30 nm. In particular embodiments, the delivery system complex has a zeta potential of about −17 mV.

The biodegradable ionic precipitate can be any precipitate that is biodegradable, such as those non-limiting examples provided elsewhere herein, but in some embodiments, the ionic precipitate is a calcium phosphate precipitate. Nanoparticles comprising a calcium phosphate precipitate, wherein the precipitate is ionically bound to the inner leaflet of the surrounding bilayer, and wherein the precipitate forms a shell surrounding an inner core are referred to herein as lipid/calcium phosphate-II (LCP-II) nanoparticles.

The lipid bilayer surrounding the biodegradable ionic precipitate has an inner and an outer leaflet. In some embodiments, particularly those in which the ionic precipitate is a calcium phosphate precipitate, the inner leaflet comprises an amphiphilic lipid having a free phosphate group. In some of these embodiments, the amphiphilic lipid having a free phosphate group is dioleoyl phosphatidic acid (DOPA).

The outer leaflet of the lipid bilayer can comprise any type of lipid, but in some embodiments, it comprises a neutral lipid. In particular embodiments, the neutral lipid is dioleoyl phosphatidylcholine (DOPC).

The bioactive compound can be any water-soluble bioactive compound, but in some embodiments, particularly those in which the ionic precipitate is a calcium phosphate precipitate, the bioactive compound has a phosphate group.

The water-soluble bioactive compound can be a water-soluble chemotherapeutic drug, including but not limited to AraC monophosphate or gemcitabine monophosphate. In other embodiments, the bioactive compound comprises a polynucleotide of interest or a polypeptide of interest, such as a silencing element (e.g., siRNA) as described elsewhere herein.

Methods of making delivery system complexes comprising a biodegradable ionic precipitate comprising a bioactive compound surrounded by a lipid bilayer comprising an inner and an outer leaflet, wherein the biodegradable ionic precipitate is ionically bound to the inner leaflet of the lipid bilayer are provided. Such methods comprise mixing a first reverse microemulsion comprising a cation and a second reverse microemulsion comprising an anion and an anionic lipid to form a biodegradable ionic precipitate, wherein the bioactive compound is within the first reverse microemulsion or the second reverse microemulsion; washing the biodegradable ionic precipitate; solubilizing the biodegradable ionic precipitate in a volatile, organic solvent to form a biodegradable ionic precipitate/solvent mixture; adding a lipid to the biodegradable ionic precipitate/solvent mixture; and evaporating the volatile, organic solvent to produce said delivery system complex.

In some embodiments, the first reverse microemulsion has a pH of about 7 and the second reverse microemulsion has a pH of about 9.

In some embodiments, the cation is a divalent or a trivalent cation. In particular embodiments, the cation is a calcium ion. The method can further comprise producing the first reverse microemulsion, which can include providing an aqueous solution comprising calcium chloride, and mixing the aqueous solution comprising calcium chloride with a non-ionic surfactant and an organic solvent.

In some embodiments, the organic solvent is hexanol and/or cyclohexane. In particular embodiments, the organic solvent comprises cyclohexane and hexanol at a volume-to-volume ratio of about 78:11.

The non-ionic surfactant can be any non-ionic surfactant, including those non-limiting examples provided elsewhere herein, but in certain embodiments, the non-ionic surfactant is Triton-X 100. In particular embodiments, the aqueous solution comprising calcium chloride is mixed with a solution of cyclohexane, hexanol, and Triton-X 100 at a volume/volume/volume ratio of about 78:11:11.

In some embodiments the anion is a divalent or a trivalent anion. In particular embodiments, the anion is a phosphate ion. The method can further comprise producing the second reverse microemulsion, which can include providing an aqueous solution comprising sodium phosphate, and mixing the aqueous solution comprising sodium phosphate with an anionic lipid, a non-ionic surfactant, and an organic solvent.

Again, the organic solvent can comprise hexanol and/or cyclohexane. In particular embodiments, the organic solvent comprises cyclohexane and hexanol at a volume-to-volume ratio of about 78:11.

Likewise, the non-ionic surfactant used to produce the second reverse microemulsion can be any non-ionic surfactant, including those non-limiting examples provided elsewhere herein, but in certain embodiments, the non-ionic surfactant is Triton-X 100. In particular embodiments, the aqueous solution comprising sodium phosphate and the anionic lipid is mixed with a solution of cyclohexane, hexanol, and Triton-X 100 at a volume/volume/volume ratio of about 78:11:11.

The volatile, organic solvent within which the biodegradable ionic precipitate is solubilized can be chloroform. In some embodiments, the biodegradable ionic precipitate is washed with ethanol, and the washing step can be performed about 1-5 times, including 1, 2, 3, 4, and 5.

In some embodiments, particularly those wherein the biodegradable ionic precipitate is calcium phosphate, the anionic lipid is an amphiphilic lipid having a free phosphate group, such as dioleoyl phosphatidic acid.

The lipid added to the biodegradable ionic precipitate/solvent mixture can be a neutral lipid, such as dioleoyl phosphatidylcholine. In some embodiments, the lipid added to the biodegradable ionic precipitate/solvent mixture can comprise a mixture of neutral lipids and a lipid-polyethylene glycol (lipid-PEG) conjugate, a lipid-targeting ligand conjugate, or a combination thereof. In certain embodiments, a mixture of neutral lipids (e.g., DOPC) and a lipid-PEG conjugate, a lipid-targeting ligand conjugate, or a combination thereof is added to the biodegradable ionic precipitate/solvent mixture at a molar ratio of 10 neutral lipid (e.g., DOPC) to 1 lipid-PEG conjugate, lipid targeting ligand conjugate, or combination thereof (e.g., DSPE-PEG-AA). Alternatively, the lipid-PEG conjugate, lipid targeting ligand conjugate, or a combination thereof can be added to the outer leaflet of the lipid bilayer through post-insertion described elsewhere herein.

III. Bioactive Compounds

When the precipitate dissolves, it releases the cations and anions that form the ionic precipitate, and the bioactive compound comprised therein. By "bioactive compound" is intended any agent that has a desired effect (e.g., therapeutic effect) on a living cell, tissue, or organism, or an agent that can desirably interact with a component (e.g., enzyme) of a living cell, tissue, or organism. Bioactive compounds can include, but are not limited to, polynucleotides, polypeptides, polysaccharides, organic and inorganic small molecules. The term "bioactive compound" encompasses both naturally occurring and synthetic bioactive compounds. The term "bioactive compound" can refer to a detection or diagnostic agent that interacts with a biological molecule to provide a detectable readout that reflects a particular physiological or pathological event. Although the release of the cations and anions from the ionic precipitate once the precipitate dissolves can have an effect on the cell by increasing the osmotic potential of the endosome within which it is contained, leading to eventual bursting of the endosome, the anions and cations that make up the biodegradable ionic precipitate are not considered bioactive compounds.

The bioactive compound of the delivery system can be a drug, including, but not limited to, antimicrobials, antibiotics, antimycobacterials, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics, and diagnostic agents.

In a preferred embodiment, the bioactive compound is an anticancer drug. In this embodiment, it is preferred that the bioactive compound is gemcitabine monophosphate and salts, esters, conformers and produgs thereof. Gemcitabine monophosphate has the following structure:

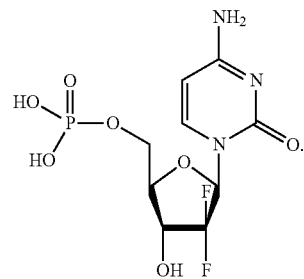

Gemcitabine monophosphate can be obtained by methods such as those disclosed in EP0376518.

In those embodiments wherein the bioactive compound comprises a polynucleotide, the delivery system complex can be referred to as a "polynucleotide delivery system" or "polynulceotide delivery system complex."

As used herein, the term "deliver" refers to the transfer of a substance or molecule (e.g., a polynucleotide) to a physiological site, tissue, or cell. This encompasses delivery to the intracellular portion of a cell or to the extracellular space. Delivery of a polynucleotide into the intracellular portion of a cell is also often referred to as "transfection."

As used herein, the term "intracellular" or "intracellularly" has its ordinary meaning as understood in the art. In general, the space inside of a cell, which is encircled by a membrane, is defined as "intracellular" space. Similarly, as used herein, the term "extracellular" or "extracellularly" has its ordinary meaning as understood in the art. In general, the space outside of the cell membrane is defined as "extracellular" space.

The term "polynucleotide" is intended to encompass a singular nucleic acid, as well as plural nucleic acids, and refers to a nucleic acid molecule or construct, e.g., messenger RNA (mRNA), plasmid DNA (pDNA), or short interfering RNA (siRNA). A polynucleotide can be single-stranded or double-stranded, linear or circular. A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments or synthetic analogues thereof, present in a polynucleotide. The term "polynucleotide" can refer to an isolated polynucleotide, including recombinant polynucleotides maintained in heterologous host cells or purified (partially or substantially) polynucleotides in solution. Polynucleotides or nucleic acids according to the present invention further include such molecules produced synthetically. Polynucleotides can also include isolated expression vectors, expression constructs, or populations thereof "Polynucleotide" can also refer to amplified products of itself, as in a polymerase chain reaction. The "polynucleotide" can contain modified nucleic acids, such as phosphorothioate, phosphate, ring atom modified derivatives, and the like. The "polynucleotide" can be a naturally occurring polynucleotide (i.e., one existing in nature without human intervention), or a recombinant polynucleotide (i.e., one existing only with human intervention). While the terms "polynucleotide" and "oligonucleotide" both refer to a polymer of nucleotides, as used herein, an oligonucleotide is typically less than 100 nucleotides in length.

As used herein, the term "polynucleotide of interest" refers to a polynucleotide that is to be delivered to a cell to elicit a desired effect in the cell (e.g., a therapeutic effect, a change in gene expression). A polynucleotide of interest can be of any length and can include, but is not limited to, a polynucleotide comprising a coding sequence for a polypeptide of interest or a polynucleotide comprising a silencing element. In certain embodiments, when the polynucleotide is expressed or introduced into a cell, the polynucleotide of interest or polypeptide encoded thereby has therapeutic activity.

In some embodiments, delivery system complexes comprise a polynucleotide of interest comprising a coding sequence for a polypeptide of interest.

For the purposes of the present invention, a "coding sequence for a polypeptide of interest" or "coding region for a polypeptide of interest" refers to the polynucleotide sequence that encodes that polypeptide. As used herein, the terms "encoding" or "encoded" when used in the context of a specified nucleic acid mean that the nucleic acid comprises the requisite information to direct translation of the nucleotide sequence into a specified polypeptide. The information by which a polypeptide is encoded is specified by the use of codons. The "coding region" or "coding sequence" is the portion of the nucleic acid that consists of codons that can be translated into amino acids. Although a "stop codon" or "translational termination codon" (TAG, TGA, or TAA) is not translated into an amino acid, it can be considered to be part of a coding region. Likewise, a transcription initiation codon (ATG) may or may not be considered to be part of a coding region. Any sequences flanking the coding region, however, for example, promoters, ribosome binding sites, transcriptional terminators, introns, and the like, are not considered to be part of the coding region. In some embodiments, however, while not considered part of the coding region per se, these regulatory sequences and any other regulatory sequence, particularly signal sequences or sequences encoding a peptide tag, may be part of the polynucleotide sequence encoding the polypeptide of interest. Thus, a polynucleotide sequence encoding a polypeptide of interest comprises the coding sequence and optionally any sequences flanking the coding region that contribute to expression, secretion, and/or isolation of the polypeptide of interest.

The term "expression" has its meaning as understood in the art and refers to the process of converting genetic information encoded in a gene or a coding sequence into RNA (e.g., mRNA, rRNA, tRNA, or snRNA) through "transcription" of a polynucleotide (e.g., via the enzymatic action of an RNA polymerase), and for polypeptide-encoding polynucleotides, into a polypeptide through "translation" of mRNA. Thus, an "expression product" is, in general, an RNA transcribed from the gene (e.g., either pre- or post-processing) or polynucleotide or a polypeptide encoded by an RNA transcribed from the gene (e.g., either pre- or post-modification).

As used herein, the term "polypeptide" or "protein" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

The term "polypeptide of interest" refers to a polypeptide that is to be delivered to a cell or is encoded by a polynucleotide that is to be delivered to a cell to elicit a desired effect in the cell (e.g., a therapeutic effect). The polypeptide of interest can be of any species and of any size. In certain embodiments, however, the protein or polypeptide of interest is a therapeutically useful protein or polypeptide. In some embodiments, the protein can be a mammalian protein, for example a human protein. In certain embodiments, the polynucleotide comprises a coding sequence for a tumor suppressor or a cytotoxin (e.g., diphtheria toxin (DT), Pseudomonas exotoxin A (PE), pertussis toxin (PT), and the pertussis adenylate cyclase (CYA)).

The term "tumor suppressor" refers to a polypeptide or a gene that encodes a polypeptide that is capable of inhibiting the development, growth, or progression of cancer. Tumor suppressor polypeptides include those proteins that regulate cellular proliferation or responses to cellular and genomic damage, or induce apoptosis. Non-limiting examples of tumor suppressor genes include p53, p110Rb, and p72. Thus, in some embodiments, the delivery system complexes of the present invention comprise a polynucleotide of interest comprising a coding sequence for a tumor suppressor.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the website www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (bioinformatics.weizmann.ac.il/cards), nucleotide sequence information can be also obtained from the EMBL Nucleotide Sequence Database (www.ebi.ac.uk/embl) or the DNA Databank or Japan (DDBJ, www.ddbi.nig.ac.jp). Additional sites for information on amino acid sequences include Georgetown's protein information resource website (www.pir.georgetown.edu) and Swiss-Prot (au.expasy.org/sprot/sprot-top.html).

In some embodiments, the polynucleotide of interest of the delivery system complexes of the invention comprises a silencing element, wherein expression or introduction of the silencing element into a cell reduces the expression of a target polynucleotide or polypeptide encoded thereby.

The terms "introduction" or "introduce" when referring to a polynucleotide or silencing element refers to the presentation of the polynucleotide or silencing element to a cell in such a manner that the polynucleotide or silencing element gains access to the intracellular region of the cell.

As used herein, the term "silencing element" refers to a polynucleotide, which when expressed or introduced into a cell is capable of reducing or eliminating the level of expression of a target polynucleotide sequence or the polypeptide encoded thereby. The silencing element can comprise or encode an antisense oligonucleotide or an interfering RNA (RNAi). The term "interfering RNA" or "RNAi" refers to any RNA molecule which can enter an RNAi pathway and thereby reduce the expression of a target polynucleotide of interest. The RNAi pathway features the Dicer nuclease enzyme and RNA-induced silencing complexes (RISC) that function to degrade or block the translation of a target mRNA. RNAi is distinct from antisense oligonucleotides that function through "antisense" mechanisms that typically involve inhibition of a target transcript by a single-stranded oligonucleotide through an RNase H-mediated pathway. See, Crooke (ed.) (2001) "*Antisense Drug Technology: Principles, Strategies, and Applications*" (1st ed), Marcel Dekker; ISBN: 0824705661; 1st edition.

As used herein, a "target polynucleotide" comprises any polynucleotide sequence that one desires to decrease the level of expression. By "reduces" or "reducing" the expression level of a polynucleotide or a polypeptide encoded thereby is intended to mean, the level of the polynucleotide or the encoded polypeptide is statistically lower than the target polynucleotide level or encoded polypeptide level in an appropriate control which is not exposed to the silencing element. In particular embodiments, reducing the target polynucleotide level and/or the encoded polypeptide level according to the presently disclosed subject matter results in less than 95%, less than 90%, less than 80%, less than 70%, less than 60%, less than 50%, less than 40%, less than 30%, less than 20%, less than 10%, or less than 5% of the target polynucleotide level, or the level of the polypeptide encoded thereby in an appropriate control. Methods to assay for the level of the RNA transcript, the level of the encoded polypeptide, or the activity of the polynucleotide or polypeptide are discussed elsewhere herein.

A particular silencing element may specifically reduce the expression of a particular target polynucleotide or a polypeptide encoded thereby or the silencing element may reduce the expression of multiple target polynucleotides or polypeptides encoded thereby.

In some embodiments, the target polynucleotide is an oncogene or a proto-oncogene. The term "oncogene" is used herein in accordance with its art-accepted meaning to refer to those polynucleotide sequences that encode a gene product that contributes to cancer initiation or progression. The term "oncogene" encompasses proto-oncogenes, which are genes that do not contribute to carcinogenesis under normal circumstances, but that have been mutated, overexpressed, or activated in such a manner as to function as an oncogene. Non-limiting examples of oncogenes include growth factors or mitogens (e.g., c-Sis), receptor tyrosine kinases (e.g., epidermal growth factor receptor (EGFR), platelet-derived growth factor receptor (PDGFR), vascular endothelial growth factor receptor (VEGFR), HER2/neu), cytoplasmic tyrosine kinases (e.g., src, Abl), cytoplasmic serine/threonine kinases (e.g., raf kinase, cyclin-dependent kinases), regulatory GTPases (e.g., ras), and transcription factors (e.g., myc). In some embodiments, the target polynucleotide is EGFR.

The term "complementary" is used herein in accordance with its art-accepted meaning to refer to the capacity for precise pairing via hydrogen bonds (e.g., Watson-Crick base pairing or Hoogsteen base pairing) between two nucleosides, nucleotides or nucleic acids, and the like. For example, if a nucleotide at a certain position of a first nucleic acid is capable of stably hydrogen bonding with a nucleotide located opposite to that nucleotide in a second nucleic acid, when the nucleic acids are aligned in opposite 5' to 3' orientation (i.e., in anti-parallel orientation), then the nucleic acids are considered to be complementary at that position (where position may be defined relative to either end of either nucleic acid, generally with respect to a 5' end). The nucleotides located opposite one another can be referred to as a "base pair." A complementary base pair contains two complementary nucleotides, e.g., A and U, A and T, G and C, and the like, whereas a noncomplementary base pair contains two noncomplementary nucleotides (also referred to as a mismatch). Two polynucleotides are said to be complementary to each other when a sufficient number of corresponding positions in each molecule are occupied by nucleotides that hydrogen bond with each other, i.e., a sufficient number of base pairs are complementary.

As used herein, the term "gene" has its meaning as understood in the art. In general, a gene is taken to include gene regulatory sequences (e.g., promoters, enhancers, and the like) and/or intron sequences, in addition to coding sequences (open reading frames). It will further be appreciated that definitions of "gene" include references to nucleic acids that do not encode proteins but rather encode functional RNA molecules, or precursors thereof, such as microRNA or siRNA precursors, tRNAs, and the like.

The term "hybridize" as used herein refers to the interaction between two complementary nucleic acid sequences in which the two sequences remain associated with one another under appropriate conditions.

A silencing element can comprise the interfering RNA or antisense oligonucleotide, a precursor to the interfering RNA or antisense oligonucleotide, a template for the transcription of an interfering RNA or antisense oligonucleotide, or a template for the transcription of a precursor interfering RNA or antisense oligonucleotide, wherein the precursor is processed within the cell to produce an interfering RNA or antisense oligonucleotide. Thus, for example, a dsRNA silencing element includes a dsRNA molecule, a transcript or polyribonucleotide capable of forming a dsRNA, more than one transcript or polyribonucleotide capable of forming a dsRNA, a DNA encoding a dsRNA molecule, or a DNA encoding one strand of a dsRNA molecule. When the silencing element comprises a DNA molecule encoding an interfering RNA, it is recognized that the DNA can be transiently expressed in a cell or stably incorporated into the genome of the cell. Such methods are discussed in further detail elsewhere herein.

The silencing element can reduce or eliminate the expression level of a target polynucleotide or encoded polypeptide by influencing the level of the target RNA transcript, by influencing translation, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297: 2215-2218; and Hall et al. (2002) *Science* 297:2232-2237. Methods to assay for functional interfering RNA that are capable of reducing or eliminating the level of a sequence of interest are disclosed elsewhere herein.

Any region of the target polynucleotide can be used to design a domain of the silencing element that shares sufficient sequence identity to allow for the silencing element to decrease the level of the target polynucleotide or encoded polypeptide. For instance, the silencing element can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof.

The ability of a silencing element to reduce the level of the target polynucleotide can be assessed directly by measuring the amount of the target transcript using, for example, Northern blots, nuclease protection assays, reverse transcription (RT)-PCR, real-time RT-PCR, microarray analysis, and the like. Alternatively, the ability of the silencing element to reduce the level of the target polynucleotide can be measured directly using a variety of affinity-based approaches (e.g., using a ligand or antibody that specifically binds to the target polypeptide) including, but not limited to, Western blots, immunoassays, ELISA, flow cytometry, protein microarrays, and the like. In still other methods, the ability of the silencing element to reduce the level of the target polynucleotide can be assessed indirectly, e.g., by measuring a functional activity of the polypeptide encoded by the transcript or by measuring a signal produced by the polypeptide encoded by the transcript.

Various types of silencing elements are discussed in further detail below.

In one embodiment, the silencing element comprises or encodes a double stranded RNA molecule. As used herein, a "double stranded RNA" or "dsRNA" refers to a polyribonucleotide structure formed either by a single self-complementary RNA molecule or a polyribonucleotide structure formed by the expression of least two distinct RNA strands. Accordingly, as used herein, the term "dsRNA" is meant to encompass other terms used to describe nucleic acid molecules that are capable of mediating RNA interference or gene silencing, including, for example, small RNA (sRNA), short-interfering RNA (siRNA), double-stranded RNA (dsRNA), micro-RNA (miRNA), hairpin RNA, short hairpin RNA (shRNA), and others. See, for example, Meister and Tuschl (2004) *Nature* 431:343-349 and Bonetta et al. (2004) *Nature Methods* 1:79-86.

In specific embodiments, at least one strand of the duplex or double-stranded region of the dsRNA shares sufficient sequence identity or sequence complementarity to the target polynucleotide to allow for the dsRNA to reduce the level of expression of the target polynucleotide or encoded polypeptide. As used herein, the strand that is complementary to the target polynucleotide is the "antisense strand," and the strand homologous to the target polynucleotide is the "sense strand."

In one embodiment, the dsRNA comprises a hairpin RNA. A hairpin RNA comprises an RNA molecule that is capable of folding back onto itself to form a double stranded structure. Multiple structures can be employed as hairpin elements. For example, the hairpin RNA molecule that hybridizes with itself to form a hairpin structure can comprise a single-stranded loop region and a base-paired stem. The base-paired stem region can comprise a sense sequence corresponding to all or part of the target polynucleotide and further comprises an antisense sequence that is fully or partially complementary to the sense sequence. Thus, the base-paired stem region of the silencing element can determine the specificity of the silencing. See, for example, Chuang and Meyerowitz (2000) *Proc. Natl. Acad. Sci. USA* 97:4985-4990, herein incorporated by reference. A transient assay for the efficiency of hpRNA constructs to silence gene expression in vivo has been described by Panstruga et al. (2003) *Mol. Biol. Rep.* 30:135-140, herein incorporated by reference.

A "short interfering RNA" or "siRNA" comprises an RNA duplex (double-stranded region) and can further comprise one or two single-stranded overhangs, e.g., 3' or 5' overhangs. The duplex can be approximately 19 base pairs (bp) long, although lengths between 17 and 29 nucleotides, including 17, 18, 19, 20, 21, 22, 23, 24, 25, 26, 27, 28, and 29 nucleotides, can be used. An siRNA can be formed from two RNA molecules that hybridize together or can alternatively be generated from a single RNA molecule that includes a self-hybridizing portion. The duplex portion of an siRNA can include one or more bulges containing one or more unpaired and/or mismatched nucleotides in one or both strands of the duplex or can contain one or more noncomplementary nucleotide pairs. One strand of an siRNA (referred to herein as the antisense strand) includes a portion that hybridizes with a target transcript. In certain embodiments, one strand of the siRNA (the antisense strand) is precisely complementary with a region of the target transcript over at least about 17 nucleotides, 18 nucleotides, 19 nucleotides, 20 nucleotides, 21 nucleotides, or more meaning that the siRNA antisense strand hybridizes to the target transcript without a single mismatch (i.e., without a single noncomplementary base pair) over that length. In other embodiments, one or more mismatches between the siRNA antisense strand and the targeted portion of the target transcript can exist. In embodiments in which perfect complementarity is not achieved, any mismatches between the siRNA antisense strand and the target transcript can be located at or near the 3' end of the siRNA antisense strand. For example, in certain embodiments, nucleotides 1-9, 2-9, 2-10, and/or 1-10 of the antisense strand are perfectly complementary to the target.

Considerations for the design of effective siRNA molecules are discussed in McManus et al. (2002) *Nature Reviews Genetics* 3: 737-747 and in Dykxhoorn et al. (2003) *Nature Reviews Molecular Cell Biology* 4: 457-467. Such considerations include the base composition of the siRNA, the position of the portion of the target transcript that is complementary to the antisense strand of the siRNA relative to the 5' and 3' ends of the transcript, and the like. A variety of computer programs also are available to assist with selection of siRNA sequences, e.g., from Ambion (web site having URL www.ambion.com), at the web site having the URL www.sinc.sunysb.edu/Stu/shilin/rnai.html. Additional design considerations that also can be employed are described in Semizarov et al. *Proc. Natl. Acad. Sci.* 100: 6347-6352.

The term "short hairpin RNA" or "shRNA" refers to an RNA molecule comprising at least two complementary portions hybridized or capable of hybridizing to form a double-stranded (duplex) structure sufficiently long to mediate RNAi (generally between approximately 17 and 29 nucleotides in length, including 17, 18, 19, 20, 21, 22, 23, 24, 25, 26, 27, 28, and 29 nucleotides in length, and in some embodiments, typically at least 19 base pairs in length), and at least one single-stranded portion, typically between approximately 1 and 20 or 1 to 10 nucleotides in length that forms a loop connecting the two nucleotides that form the base pair at one end of the duplex portion. The duplex portion can, but does not require, one or more bulges consisting of one or more unpaired nucleotides. In specific embodiments, the shRNAs comprise a 3' overhang. Thus, shRNAs are precursors of siRNAs and are, in general, similarly capable of inhibiting expression of a target transcript.

In particular, RNA molecules having a hairpin (stem-loop) structure can be processed intracellularly by Dicer to yield an siRNA structure referred to as short hairpin RNAs (shRNAs), which contain two complementary regions that hybridize to one another (self-hybridize) to form a double-stranded (duplex) region referred to as a stem, a single-stranded loop connecting the nucleotides that form the base pair at one end of the duplex, and optionally an overhang, e.g., a 3' overhang. The stem can comprise about 19, 20, or 21 bp long, though shorter and longer stems (e.g., up to about 29 nt) also can be used. The loop can comprise about 1-20, including 1, 2, 3, 4, 5, 6, 7, 8, 9, 10, 11, 12, 13, 14, 15, 16, 17, 18, 19, 20 nt, about 4-10, or about 6-9 nt. The overhang, if present, can comprise approximately 1-20 nt or approximately 2-10 nt. The loop can be located at either the 5' or 3' end of the region that is complementary to the target transcript whose inhibition is desired (i.e., the antisense portion of the shRNA).

Although shRNAs contain a single RNA molecule that self-hybridizes, it will be appreciated that the resulting duplex structure can be considered to comprise sense and antisense strands or portions relative to the target mRNA and can thus be considered to be double-stranded. It will therefore be convenient herein to refer to sense and antisense strands, or sense and antisense portions, of an shRNA, where the antisense strand or portion is that segment of the molecule that forms or is capable of forming a duplex with and is complementary to the targeted portion of the target polynucleotide, and the sense strand or portion is that segment of the molecule that forms or is capable of forming a duplex with the antisense strand or portion and is substantially identical in sequence to the targeted portion of the target transcript. In general, considerations for selection of the sequence of the antisense strand of an shRNA molecule are similar to those for selection of the sequence of the antisense strand of an siRNA molecule that targets the same transcript.

In one embodiment, the silencing element comprises or encodes an miRNA or an miRNA precursor. "MicroRNAs" or "miRNAs" are regulatory agents comprising about 19 ribonucleotides which are highly efficient at inhibiting the expression of target polynucleotides. See, for example, Saetrom et al. (2006) *Oligonucleotides* 16:115-144, Wang et al. (2006) *Mol. Cell* 22:553-60, Davis et al. (2006) *Nucleic Acid Research* 34:2294-304, Pasquinelli (2006) *Dev. Cell* 10:419-24, all of which are herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

It is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA, which is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (McManus et al. (2002) *RNA* 8:842-50). In specific embodiments, 2-8 nucleotides of the miRNA are perfectly complementary to the target. A large number of endogenous human miRNAs have been identified. For structures of a number of endogenous miRNA precursors from various organisms, see Lagos-Quintana et al. (2003) *RNA* 9 (2):175-9; see also Bartel (2004) *Cell* 116:281-297.

A miRNA or miRNA precursor can share at least about 80%, 85%, 90%, 91%. 92%, 93%, 94%, 95%, 96%, 97%, 98%, 99%, or 100% sequence complementarity with the target transcript for a stretch of at least about 15, 16, 17, 18, 19, 20, 21, 22, 23, 24, 25, 26, 27, 28, 29, or 30 nucleotides. In specific embodiments, the region of precise sequence complementarity is interrupted by a bulge. See, Ruvkun (2001) *Science* 294: 797-799, Zeng et al. (2002) *Molecular Cell* 9:1-20, and Mourelatos et al. (2002) *Genes Dev* 16:720-728.

In some embodiments, the silencing element comprises or encodes an antisense oligonucleotide. An "antisense oligonucleotide" is a single-stranded nucleic acid sequence that is wholly or partially complementary to a target polynucleotide, and can be DNA, or its RNA counterpart (i.e., wherein T residues of the DNA are U residues in the RNA counterpart).

The antisense oligonucleotides of this invention are designed to be hybridizable with target RNA (e.g., mRNA) or DNA. For example, an oligonucleotide (e.g., DNA oligonucleotide) that hybridizes to a mRNA molecule can be used to target the mRNA for RnaseH digestion. Alternatively, an oligonucleotide that hybridizes to the translation initiation site of an mRNA molecule can be used to prevent translation of the mRNA. In another approach, oligonucleotides that bind to double-stranded DNA can be administered. Such oligonucleotides can form a triplex construct and inhibit the transcription of the DNA. Triple helix pairing prevents the double helix from opening sufficiently to allow the binding of polymerases, transcription factors, or regulatory molecules. Recent therapeutic advances using triplex DNA have been described (see, e.g., J. E. Gee et al., 1994, Molecular and Immunologic Approaches, Futura Publishing Co., Mt. Kisco, N.Y.). Such oligonucleotides of the invention can be constructed using the base-pairing rules of triple helix formation and the nucleotide sequences of the target genes.

As non-limiting examples, antisense oligonucleotides can be targeted to hybridize to the following regions: mRNA cap region; translation initiation site; translational termination site; transcription initiation site; transcription termination site; polyadenylation signal; 3' untranslated region; 5' untranslated region; 5' coding region; mid coding region; and 3' coding region. In some embodiments, the complementary oligonucleotide is designed to hybridize to the most unique 5' sequence of a gene, including any of about 15-35 nucleotides spanning the 5' coding sequence.

Accordingly, the antisense oligonucleotides in accordance with this invention can comprise from about 10 to about 100 nucleotides, including, but not limited to about 10, 11, 12, 13, 14, 15, 16, 17, 18, 19, 20, 21, 22, 23, 24, 25, 30, 40, 50, 60, 70, 80, 90, or about 100 nucleotides.

Antisense nucleic acids can be produced by standard techniques (see, for example, Shewmaker et al., U.S. Pat. No. 5,107,065). Appropriate oligonucleotides can be designed using OLIGO software (Molecular Biology Insights, Inc., Cascade, Colo.; http://www.oligo.net).

Those of ordinary skill in the art will readily appreciate that a silencing element can be prepared according to any available technique including, but not limited to, chemical synthesis, enzymatic or chemical cleavage in vivo or in vitro, template transcription in vivo or in vitro, or combinations of the foregoing.

As discussed above, the silencing elements employed in the methods and compositions of the invention can comprise a DNA molecule which when transcribed produces an interfering RNA or a precursor thereof, or an antisense oligonucleotide. In such embodiments, the DNA molecule encoding the silencing element is found in an expression cassette. In addition, polynucleotides that comprise a coding sequence for a polypeptide of interest are found in an expression cassette.

The expression cassette comprises one or more regulatory sequences, selected on the basis of the cells to be used for expression, operably linked to a polynucleotide encoding the silencing element or polypeptide of interest. "Operably linked" is intended to mean that the nucleotide sequence of interest (i.e., a DNA encoding a silencing element or a coding sequence for a polypeptide of interest) is linked to the regulatory sequence(s) in a manner that allows for expression of the nucleotide sequence (e.g., in an in vitro transcription/translation system or in a cell when the expression cassette or vector is introduced into a cell). "Regulatory sequences" include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression cassette can depend on such factors as the choice of the host cell to be transformed, the level of expression of the silencing element or polypeptide of interest desired, and the like. Such expression cassettes typically include one or more appropriately positioned sites for restriction enzymes, to facilitate introduction of the nucleic acid into a vector.

It will further be appreciated that appropriate promoter and/or regulatory elements can readily be selected to allow expression of the relevant transcription units/silencing elements in the cell of interest. Promoters can be constitutively active, chemically-inducible, development-, cell-, or tissue-specific promoters. In certain embodiments, the promoter utilized to direct intracellular expression of a silencing element is a promoter for RNA polymerase III (Pol III). References discussing various Pol III promoters, include, for example, Yu et al. (2002) *Proc. Natl. Acad. Sci.* 99 (9), 6047-6052; Sui et al. (2002) *Proc. Natl. Acad. Sci.* 99 (8), 5515-5520 (2002); Paddison et al. (2002) *Genes and Dev.* 16, 948-958; Brummelkamp et al. (2002) *Science* 296, 550-553; Miyagashi (2002) *Biotech.* 20, 497-500; Paul et al. (2002) *Nat. Biotech.* 20, 505-508; Tuschl et al. (2002) *Nat. Biotech.* 20, 446-448. According to other embodiments, a promoter for RNA polymerase I, e.g., a tRNA promoter, can be used. See McCown et al. (2003) *Virology* 313 (2):514-24; Kawasaki (2003) *Nucleic Acids Res.* 31 (2):700-7. In some embodiments in which the polynucleotide comprises a coding sequence for a polypeptide of interest, a promoter for RNA polymerase II can be used.

The regulatory sequences can also be provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.).

In vitro transcription can be performed using a variety of available systems including the T7, SP6, and T3 promoter/polymerase systems (e.g., those available commercially from Promega, Clontech, New England Biolabs, and the like) in order to make a silencing element. Vectors including the T7, SP6, or T3 promoter are well known in the art and can readily be modified to direct transcription of silencing elements. When silencing elements are synthesized in vitro, the strands can be allowed to hybridize before introducing into a cell or before administration to a subject. As noted above, silencing elements can be delivered or introduced into a cell as a single RNA molecule including self-complementary portions (e.g., an shRNA that can be processed intracellularly to yield an siRNA), or as two strands hybridized to one another. In other embodiments, the silencing elements employed are transcribed in vivo. As discussed elsewhere herein, regardless of whether the silencing element is transcribed in vivo or in vitro, in either scenario, a primary transcript can be produced which can then be processed (e.g., by one or more cellular enzymes) to generate the interfering RNA that accomplishes gene inhibition.

In those embodiments in which the silencing element is an interfering RNA, the interfering RNA can be generated by transcription from a promoter, either in vitro or in vivo. For instance, a construct can be provided containing two separate transcribable regions, each of which generates a 21-nt transcript containing a 19-nt region complementary with the other. Alternatively, a single construct can be utilized that contains opposing promoters and terminators positioned so that two different transcripts, each of which is at least partly complementary to the other, are generated. Alternatively, an RNA-inducing agent can be generated as a single transcript, for example by transcription of a single transcription unit encoding self complementary regions. A template is employed that includes first and second complementary regions, and optionally includes a loop region connecting the portions. Such a template can be utilized for in vitro transcription or in vivo transcription, with appropriate selection of promoter and, optionally, other regulatory elements, e.g., a terminator.

In some embodiments, the expression cassette or polynucleotide can comprise sequences sufficient for site-specific integration into the genome of the cell to which is has been introduced.

In some embodiments, the presently disclosed delivery system complexes comprise a liposome encapsulating a biodegradable ionic precipitate comprising a polypeptide of interest that is to be delivered to a cell. The delivery system complexes disclosed herein are capable of introducing a polypeptide into the intracellular region of a cell.

In some of these embodiments, the polypeptide that is delivered into the cell comprises a cationic or an anionic polypeptide. As used herein, an "anionic polypeptide" is a polypeptide as described herein that has a net negative charge at physiological pH. The anionic polypeptide can comprise at least about 20%, 30%, 40%, 50%, 60%, 70%, 75%, 80%, 85%, 90%, 95%, 96%, 97%, 98%, 99%, or 100% amino acid residues that have a negative charge at physiological pH. These include aspartic acid (D), asparagine (N), glutamic acid (E), and glutamine (Q). In particular embodiments, the polypeptide of interest is acetylated at the amino and/or carboxyl termini to enhance the negative charge of the polypeptide. In certain embodiments, the polypeptide is phosphorylated (i.e., comprises at least one phosphate group). Alternatively, a "cationic polypeptide" is a polypeptide as described herein that has a net positive charge at physiological pH. The cationic polypeptide can comprise at least about 20%, 30%, 40%, 50%, 60%, 70%, 75%, 80%, 85%, 90%, 95%, 96%, 97%, 98%, 99%, or 100% amino acid residues that have a positive charge at physiological pH. These include lysine (K), arginine (R), and histidine (H).

In some of the embodiments wherein the delivery system complex comprises a polypeptide of interest, the polypeptide of interest has at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, or more amino acid residues. In some embodiments, the polypeptide of interest that is delivered to a cell using the delivery system complexes disclosed herein can have a molecular weight from about 200 Daltons to about 50,000 Daltons, including but not limited to, about 200, 300, 400, 500, 600, 700, 800, 900, 1,000, 5,000, 10,000, 20,000, 30,000, 40,000, and 50,000 Daltons. In particular embodiments, the delivery system complex is capable of delivering between about 1 and about $2\times10^{16}$ molecules of the polypeptide of interest in a single lipid vehicle, including but not limited to about 1, 10, 100, 500, 1000, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, and $2\times10^{16}$ molecules.

In some embodiments, the polypeptide of interest has an amino acid sequence that mimics the catalytic domain of an enzyme that functions in an essential signaling pathway in the cell (e.g., EGFR). A non-limiting example of such an enzyme is the epidermal growth factor receptor (EGFR) tyrosine kinase. The polypeptide of interest can therefore comprise the EV peptide (set forth as SEQ ID NO: 3) described in International Application No. PCT/US2009/042485, entitled "Methods and compositions for the delivery of bioactive compounds" that was filed on May 1, 2009, and is herein incorporated by reference in its entirety. In other embodiments wherein the delivery system complex comprises a polypeptide of interest, the polypeptide of interest comprises an imaging peptide comprising at least one caspase 3 recognition motif, as described in International. Appl. No. PCT/US2009/042485. As further described in International. Appl. No. PCT/US2009/042485, in some of these embodiments, the delivery system complex further comprises a cytotoxic bioactive compound.

The bioactive compound is incorporated within or associated with the biodegradable ionic precipitate within the aqueous core of the liposome of the delivery system complex such that when the ionic precipitate dissolves into its individual cations and anions, the bioactive compound is released. Without being bound by any theory or mechanism of action, it is believed that in those embodiments wherein the bioactive compound comprises polynucleotides, the polynucleotides associate with the cations and anions of the biodegradable ionic precipitate through ionic interactions. Thus, in some embodiments, the bioactive compound is a charged compound (either cationic or anionic).

It should be noted that the delivery system complexes can comprise more than one type of bioactive compound. As a non-limiting example, more than one type of bioactive compound may be incorporated into the biodegradable ionic precipitate within the aqueous core of the liposome.

IV. PEGylated Delivery Systems and Targeted Delivery Systems

As described elsewhere herein, the delivery system complexes can have a surface charge (e.g., positive charge). In some embodiments, the surface charge of the liposome of the delivery system can be minimized by incorporating lipids comprising polyethylene glycol (PEG) moieties into the liposome. Reducing the surface charge of the liposome of the delivery system can reduce the amount of aggregation between the delivery system complexes and serum proteins and enhance the circulatory half-life of the complex (Yan, Scherphof, and Kamps (2005) *J Liposome Res* 15:109-139). Thus, in some embodiments, the exterior surface of the liposome or the outer leaflet of the lipid bilayer of the delivery system comprises a PEG molecule. Such a complex is referred to herein as a PEGylated delivery system complex. In these embodiments, the outer leaflet of the lipid bilayer of the liposome of the delivery system complex comprises a lipid-PEG conjugate.

A PEGylated delivery system complex can be generated through the post-insertion of a lipid-PEG conjugate into the lipid bilayer through the incubation of the delivery system complex with micelles comprising lipid-PEG conjugates, as known in the art and described elsewhere herein (Ishida et al. (1999) *FEBS Lett.* 460:129-133; Perouzel et al. (2003) *Bioconjug. Chem.* 14:884-898; see Experimental section). By "lipid-polyethylene glycol conjugate" or "lipid-PEG conjugate" is intended a lipid molecule that is covalently bound to at least one polyethylene glycol molecule. In some embodiments, the lipid-PEG conjugate comprises 1,2-distearoyl-sn-glycero-3-phosphoethanolamine-N-carboxypolyethylene glycol (DSPE-PEG). As described immediately below, these lipid-PEG conjugates can be further modified to include a targeting ligand, forming a lipid-PEG-targeting ligand conjugate (e.g., DSPE-PEG-AA). The term "lipid-PEG conjugate" also refers to these lipid-PEG-targeting ligand conjugates and a delivery system complex comprising a liposome comprising a lipid-PEG targeting ligand conjugate are considered to be both a PEGylated delivery system complex and a targeted delivery system complex, as described immediately below.

Alternatively, the delivery system complex can be PEGylated through the addition of a lipid-PEG conjugate during the formation of the outer leaflet of the lipid bilayer.

PEGylation of liposomes enhances the circulatory half-life of the liposome by reducing clearance of the complex by the reticuloendothelial (RES) system. While not being bound by any particular theory or mechanism of action, it is believed that a PEGylated delivery system complex can evade the RES system by sterically blocking the opsonization of the complexes (Owens and Peppas (2006) *Int J Pharm* 307:93-102). In order to provide enough steric hindrance to avoid opsonization, the exterior surface of the liposome must be completely covered by PEG molecules in the "brush" configuration. At low surface coverage, the PEG chains will typically have a "mushroom" configuration, wherein the PEG molecules will be located closer to the surface of the liposome. In the "brush" configuration, the PEG molecules are extended further away from the liposome surface, enhancing the steric hindrance effect. However, over-crowdedness of PEG on the surface may decrease the mobility of the polymer chains and thus decrease the steric hindrance effect (Owens and Peppas (2006) *Int J Pharm* 307:93-102).

The conformation of PEG depends upon the surface density and the molecular mass of the PEG on the surface of the liposome. The controlling factor is the distance between the PEG chains in the lipid bilayer (D) relative to their Flory dimension, $R_F$, which is defined as $aN^{3/5}$, wherein a is the persistence length of the monomer, and N is the number of monomer units in the PEG (see Nicholas et al. (2000) *Biochim Biophys Acta* 1463:167-178, which is herein incorporated by reference). Three regimes can be defined: (1) when $D>2 R_F$ (interdigitated mushrooms); (2) when $D<2 R_F$ (mushrooms); and (3) when $D<R_F$ (brushes) (Nicholas et al.).

In certain embodiments, the PEGylated delivery system complex comprises a stealth delivery system complex. By "stealth delivery system complex" is intended a delivery system complex comprising a liposome wherein the outer leaflet of the lipid bilayer of the liposome comprises a sufficient number of lipid-PEG conjugates in a configuration that allows the delivery system complex to exhibit a reduced uptake by the RES system in the liver when administered to a subject as compared to non PEGylated delivery system complexes. RES uptake can be measured using assays known in the art, including, but not limited to the liver perfusion assay described in International Application No. PCT/US2009/042485, filed on May 1, 2009. In some of these embodiments, the stealth delivery system complex comprises a liposome, wherein the outer leaflet of the lipid bilayer of the liposome comprises PEG molecules, wherein said $D<R_F$.

In some of those embodiments in which the PEGylated delivery system is a stealth polynucleotide system, the outer leaflet of the lipid bilayer of the cationic liposome comprises a lipid-PEG conjugate at a concentration of about 4 mol % to about 15 mol % of the outer leaflet lipids, including, but not limited to, about 4 mol %, about 5 mol %, about 6 mol %, about 7 mol %, 8 mol %, about 9 mol %, about 10 mol %, about 11 mol %, about 12 mol %, about 13 mol %, about 14 mol %, and about 15 mol % PEG. In certain embodiments, the outer leaflet of the lipid bilayer of the cationic liposome of the stealth delivery system complex comprises about 10.6 mol % PEG. Higher percentage values (expressed in mol %) of PEG have also surprisingly been found to be useful. Useful mol % values include those from about 12 mol % to about 50 mol %. Preferably, the values are from about 15 mol % to about 40 mol %. Also preferred are values from about 15 mol % to about 35 mol %. Most preferred values are from about 20 mol % to about 25 mol %, for example 23 mol %.

The polyethylene glycol moiety of the lipid-PEG conjugate can have a molecular weight ranging from about 100 to about 20,000 g/mol, including but not limited to about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 5000 g/mol, about 10,000 g/mol, about 15,000 g/mol, and about 20,000 g/mol. In some embodiments, the lipid-PEG conjugate comprises a PEG molecule having a molecular weight of about 2000 g/mol. In certain embodiments, the lipid-PEG conjugate comprises DSPE-PEG$_{2000}$.

In some embodiments, the delivery system complex comprises a liposome, wherein the exterior surface of the liposome, or the delivery system complex comprises a lipid bilayer wherein the outer leaflet of the lipid bilayer, comprises a targeting ligand, thereby forming a targeted delivery system. In these embodiments, the outer leaflet of the liposome comprises a targeting ligand. By "targeting ligand" is intended a molecule that targets a physically associated molecule or complex to a targeted cell or tissue. As used herein, the term "physically associated" refers to either a covalent or non-covalent interaction between two molecules. A "conjugate" refers to the complex of molecules that are covalently bound to one another. For example, the complex of a lipid covalently bound to a targeting ligand can be referred to as a lipid-targeting ligand conjugate.

Alternatively, the targeting ligand can be non-covalently bound to a lipid. "Non-covalent bonds" or "non-covalent interactions" do not involve the sharing of pairs of electrons, but rather involve more dispersed variations of electromagnetic interactions, and can include hydrogen bonding, ionic interactions, Van der Waals interactions, and hydrophobic bonds.

Targeting ligands can include, but are not limited to, small molecules, peptides, lipids, sugars, oligonucleotides, hormones, vitamins, antigens, antibodies or fragments thereof, specific membrane-receptor ligands, ligands capable of reacting with an anti-ligand, fusogenic peptides, nuclear localization peptides, or a combination of such compounds. Non-limiting examples of targeting ligands include asialoglycoprotein, insulin, low density lipoprotein (LDL), folate, benzamide derivatives, peptides comprising the arginine-glycine-aspartate (RGD) sequence, and monoclonal and polyclonal antibodies directed against cell surface molecules. In some embodiments, the small molecule comprises a benzamide derivative. In some of these embodiments, the benzamide derivative comprises anisamide.

The targeting ligand can be covalently bound to the lipids comprising the liposome or lipid bilayer of the delivery system, including a cationic lipid, or a co-lipid, forming a lipid-targeting ligand conjugate. As described above, a lipid-targeting ligand conjugate can be post-inserted into the lipid bilayer of a liposome using techniques known in the art and described elsewhere herein (Ishida et al. (1999) *FEBS Lett.* 460:129-133; Perouzel et al. (2003) *Bioconjug. Chem.* 14:884-898; see Experimental section). Alternatively, the lipid-targeting ligand conjugate can be added during the formation of the outer leaflet of the lipid bilayer.

Some lipid-targeting ligand conjugates comprise an intervening molecule in between the lipid and the targeting ligand, which is covalently bound to both the lipid and the targeting ligand. In some of these embodiments, the intervening molecule is polyethylene glycol (PEG), thus forming a lipid-PEG-targeting ligand conjugate. An example of such a lipid-targeting conjugate is DSPE-PEG-AA, in which the lipid 1,2-distearoyl-sn-glycero-3-phosphoethanolamine-N-carboxyl (DSPE) is bound to polyethylene glycol (PEG), which is bound to the targeting ligand anisamide (AA). Thus, in some embodiments, the cationic lipid vehicle of the delivery system comprises the lipid-targeting ligand conjugate DSPE-PEG-AA.

By "targeted cell" is intended the cell to which a targeting ligand recruits a physically associated molecule or complex. The targeting ligand can interact with one or more constituents of a target cell. The targeted cell can be any cell type or at any developmental stage, exhibiting various phenotypes, and can be in various pathological states (i.e., abnormal and normal states). For example, the targeting ligand can associate with normal, abnormal, and/or unique constituents on a microbe (i.e., a prokaryotic cell (bacteria), viruses, fungi, protozoa or parasites) or on a eukaryotic cell (e.g., epithelial cells, muscle cells, nerve cells, sensory cells, cancerous cells, secretory cells, malignant cells, erythroid and lymphoid cells, stem cells). Thus, the targeting ligand can associate with a constitutient on a target cell which is a disease-associated antigen including, for example, tumor-associated antigens and autoimmune disease-associated antigens. Such disease-associated antigens include, for example, growth factor receptors, cell cycle regulators, angiogenic factors, and signaling factors.

In some embodiments, the targeting ligand interacts with a cell surface protein on the targeted cell. In some of these embodiments, the expression level of the cell surface protein that is capable of binding to the targeting ligand is higher in the targeted cell relative to other cells. For example, cancer cells overexpress certain cell surface molecules, such as the HER2 receptor (breast cancer) or the sigma receptor. In certain embodiments wherein the targeting ligand comprises a benzamide derivative, such as anisamide, the targeting ligand targets the associated delivery system complex to sigma-receptor overexpressing cells, which can include, but are not limited to, cancer cells such as small- and non-small-cell lung carcinoma, renal carcinoma, colon carcinoma, sarcoma, breast cancer, melanoma, glioblastoma, neuroblastoma, and prostate cancer (Aydar, Palmer, and Djamgoz (2004) *Cancer Res.* 64:5029-5035).

Thus, in some embodiments, the targeted cell comprises a cancer cell. The terms "cancer" or "cancerous" refer to or describe the physiological condition in mammals that is typically characterized by unregulated cell growth. As used herein, "cancer cells" or "tumor cells" refer to the cells that are characterized by this unregulated cell growth. The term "cancer" encompasses all types of cancers, including, but not limited to, all forms of carcinomas, melanomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer. In some embodiments, the targeted cancer cell comprises a lung cancer cell. The term "lung cancer" refers to all types of lung cancers, including but not limited to, small cell lung cancer (SCLC), non-small-cell lung cancer (NSCLC, which includes large-cell lung cancer, squamous cell lung cancer, and adenocarcinoma of the lung), and mixed small-cell/large-cell lung cancer.

V. Pharmaceutical Compositions and Methods of Delivery and Treatment

The delivery system complexes described herein are useful in mammalian tissue culture systems, in animal studies, and for therapeutic purposes. The delivery system complexes comprising a bioactive compound having therapeutic activity when expressed or introduced into a cell can be used in therapeutic applications. The delivery system complexes can be administered for therapeutic purposes or pharmaceutical compositions comprising the delivery system complexes along with additional pharmaceutical carriers can be formulated for delivery, i.e., administering to the subject, by any available route including, but not limited to, parenteral (e.g., intravenous), intradermal, subcutaneous, oral, nasal, bronchial, opthalmic, transdermal (topical), transmucosal, rectal, and vaginal routes. In some embodiments, the route of delivery is intravenous, parenteral, transmucosal, nasal, bronchial, vaginal, and oral.

As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

As one of ordinary skill in the art would appreciate, a presently disclosed pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfate; chelating agents, such as ethylenediaminetetraacetic acid; buffers, such as acetates, citrates or phosphates; and agents for the adjustment of tonicity, such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions or dispersions such as those described elsewhere herein and sterile powders for the extemporaneous preparation of sterile injectable solutions or dispersions. For intravenous administration, suitable carriers include physiological saline, bacteriostatic water, or phosphate buffered saline (PBS). The composition should be sterile and should be fluid to the extent that easy syringability exists. In some embodiments, the pharmaceutical compositions are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polytheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols, such as manitol or sorbitol, or sodium chloride are included in the formulation. Prolonged absorption of the injectable formulation can be brought about by including in the formulation an agent that delays absorption, for example, aluminum monostearate and gelatin.

Sterile injectable solutions can be prepared by filter sterilization as described elsewhere herein. In certain embodiments, solutions for injection are free of endotoxin. Generally, dispersions are prepared by incorporating the delivery system complexes into a sterile vehicle which contains a basic dispersion medium and the required other ingredients from those enumerated above. In those embodiments in which sterile powders are used for the preparation of sterile injectable solutions, the solutions can be prepared by vacuum drying and freeze-drying which yields a powder of the active ingredient plus any additional desired ingredient from a previously sterile-filtered solution thereof.

Oral compositions generally include an inert diluent or an edible carrier. Oral compositions can be prepared using a fluid carrier for use as a mouthwash. Pharmaceutically compatible binding agents, and/or adjuvant materials can be included as part of the composition. The oral compositions can include a sweetening agent, such as sucrose or saccharin; or a flavoring agent, such as peppermint, methyl salicylate, or orange flavoring.

For administration by inhalation, the presently disclosed compositions can be delivered in the form of an aerosol spray from a pressured container or dispenser which contains a suitable propellant, e.g., a gas such as carbon dioxide, or a nebulizer. Liquid aerosols, dry powders, and the like, also can be used.

Systemic administration of the presently disclosed compositions also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical or cosmetic carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals. Guidance regarding dosing is provided elsewhere herein.

The present invention also includes an article of manufacture providing a delivery system complex described herein. The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

The present invention provides methods for delivering a bioactive compound to a cell and for treating a disease or unwanted condition in a subject with a delivery system complex comprising a bioactive compound that has therapeutic activity against the disease or unwanted condition. Further provided herein are methods for making the presently disclosed delivery system complexes.

The presently disclosed delivery system complexes can be used to deliver the bioactive compound to cells by contacting a cell with the delivery system complexes. As described elsewhere herein, the term "deliver" when referring to a bioactive compound refers to the process resulting in the placement of the composition within the intracellular space of the cell or the extracellular space surrounding the cell.

The term "cell" encompasses cells that are in culture and cells within a subject. The delivery of a polynucleotide into an intracellular space is also referred to as "transfection." In these embodiments, the cells are contacted with the delivery system complex in such a manner as to allow the bioactive compounds comprised within the delivery system complexes to gain access to the interior of the cell.

The delivery of a bioactive compound to a cell can comprise an in vitro approach, an ex vivo approach, in which the delivery of the bioactive compound into a cell occurs outside of a subject (the transfected cells can then be transplanted into the subject), and an in vivo approach, wherein the delivery occurs within the subject itself.

In some embodiments, the exterior of the delivery system complex comprises a lipid-PEG conjugate. In some of these embodiments, the delivery system complex comprises a stealth delivery system complex. In certain embodiments, the outer leaflet of the liposome of the delivery system comprises a targeting ligand, thereby forming a targeted delivery system complex, wherein the targeting ligand targets the targeted delivery system complex to a targeted cell.

The delivery system complexes described herein comprising a bioactive compound can be used for the treatment of a disease or unwanted condition in a subject, wherein the bioactive compound has therapeutic activity against the disease or unwanted condition when expressed or introduced into a cell. The bioactive compound is administered to the subject in a therapeutically effective amount. In those embodiments wherein the bioactive compound comprises a polynucleotide, when the polynucleotide of interest is administered to a subject in therapeutically effective amounts, the polynucleotide of interest or the polypeptide encoded thereby is capable of treating the disease or unwanted condition.

By "therapeutic activity" when referring to a bioactive compound is intended that the molecule is able to elicit a desired pharmacological or physiological effect when administered to a subject in need thereof.

As used herein, the terms "treatment" or "prevention" refer to obtaining a desired pharmacologic and/or physiologic effect. The effect may be prophylactic in terms of completely or partially preventing a particular infection or disease or sign or symptom thereof and/or may be therapeutic in terms of a partial or complete cure of an infection or disease and/or adverse effect attributable to the infection or the disease. Accordingly, the method "prevents" (i.e., delays or inhibits) and/or "reduces" (i.e., decreases, slows, or ameliorates) the detrimental effects of a disease or disorder in the subject receiving the compositions of the invention. The subject may be any animal, including a mammal, such as a human, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The disease or unwanted condition to be treated can encompass any type of condition or disease that can be treated therapeutically. In some embodiments, the disease or unwanted condition that is to be treated is a cancer. As described elsewhere herein, the term "cancer" encompasses any type of unregulated cellular growth and includes all forms of cancer. In some embodiments, the cancer to be treated is a lung cancer. Methods to detect the inhibition of cancer growth or progression are known in the art and include, but are not limited to, measuring the size of the primary tumor to detect a reduction in its size, delayed appearance of secondary tumors, slowed development of secondary tumors, decreased occurrence of secondary tumors, and slowed or decreased severity of secondary effects of disease.

It will be understood by one of skill in the art that the delivery system complexes can be used alone or in conjunction with other therapeutic modalities, including, but not limited to, surgical therapy, radiotherapy, or treatment with any type of therapeutic agent, such as a drug. In those embodiments in which the subject is afflicted with cancer, the delivery system complexes can be delivered in combination with any chemotherapeutic agent well known in the art.

When administered to a subject in need thereof, the delivery system complexes can further comprise a targeting ligand, as discussed elsewhere herein. In these embodiments, the targeting ligand will target the physically associated complex to a targeted cell or tissue within the subject. In certain embodiments, the targeted cell or tissue comprises a diseased cell or tissue or a cell or tissue characterized by the unwanted condition. In some of these embodiments, the delivery system complex is a stealth delivery system complex wherein the surface charge is shielded through the association of PEG molecules and the liposome further comprises a targeting ligand to direct the delivery system complex to targeted cells.

In some embodiments, particularly those in which the diameter of the delivery system complex is less than 100 nm, the delivery system complexes can be used to deliver bioactive compounds across the blood-brain barrier (BBB) into the central nervous system or across the placental barrier. Non-limiting examples of targeting ligands that can be used to target the BBB include transferring and lactoferrin (Huang et al. (2008) *Biomaterials* 29 (2):238-246, which is herein incorporated by reference in its entirety). Further, the delivery system complexes can be transcytosed across the endothelium into both skeletal and cardiac muscle cells. For example, exon-skipping oligonucleotides can be delivered to treat Duchene muscular dystrophy (Moulton et al. (2009) *Ann N Y Acad Sci* 1175:55-60, which is herein incorporated by reference in its entirety).

Delivery of a therapeutically effective amount of a delivery system complex comprising a bioactive compound can be obtained via administration of a pharmaceutical composition comprising a therapeutically effective dose of the bioactive compound or the delivery system complex. By "therapeutically effective amount" or "dose" is meant the concentration of a delivery system or a bioactive compound comprised therein that is sufficient to elicit the desired therapeutic effect.

As used herein, "effective amount" is an amount sufficient to effect beneficial or desired clinical or biochemical results. An effective amount can be administered one or more times.

The effective amount of the delivery system complex or bioactive compound will vary according to the weight, sex, age, and medical history of the subject. Other factors which influence the effective amount can include, but are not limited to, the severity of the subject's condition, the disorder being treated, the stability of the compound or complex, and, if desired, the adjuvant therapeutic agent being administered along with the polynucleotide delivery system. Methods to determine efficacy and dosage are known to those skilled in the art. See, for example, Isselbacher et al. (1996) *Harrison's Principles of Internal Medicine* 13 ed., 1814-1882, herein incorporated by reference.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic (e.g., immunotoxic) and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the presently disclosed methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical formulation can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, and the like. The skilled artisan will appreciate that certain factors can influence the dosage and timing required to effectively treat a subject, including but not limited to the severity of the disease, disorder, or unwanted condition, previous treatments, the general health and/or age of the subject, and other diseases or unwanted conditions present. Generally, treatment of a subject can include a single treatment or, in many cases, can include a series of treatments. Further, treatment of a subject can include a single cosmetic application or, in some embodiments, can include a series of cosmetic applications.

It is understood that appropriate doses of a compound depend upon its potency and can optionally be tailored to the particular recipient, for example, through administration of increasing doses until a preselected desired response is achieved. It is understood that the specific dose level for any particular animal subject can depend on a variety of factors including the activity of the specific compound employed, the age, body weight, general health, gender, and diet of the subject, the time of administration, the route of administration, the rate of excretion, any drug combination, and the degree of expression or activity to be modulated.

One of ordinary skill in the art upon review of the presently disclosed subject matter would appreciate that the presently disclosed compounds and pharmaceutical compositions thereof, can be administered directly to a cell, a cell culture, a cell culture medium, a tissue, a tissue culture, a tissue culture medium, and the like. When referring to the delivery systems of the invention, the term "administering," and derivations thereof, comprises any method that allows for the compound to contact a cell. The presently disclosed compounds or pharmaceutical compositions thereof, can be administered to (or contacted with) a cell or a tissue in vitro or ex vivo. The presently disclosed compounds or pharmaceutical compositions thereof, also can be administered to (or contacted with) a cell or a tissue in vivo by administration to an individual subject, e.g., a patient, for example, by systemic administration (e.g., intravenous, intraperitoneal, intramuscular, subdermal, or intracranial administration) or topical application, as described elsewhere herein.

It is to be noted that the term "a" or "an" entity refers to one or more of that entity; for example, "a nanoparticle" is understood to represent one or more nanoparticles. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The following examples are offered by way of illustration and not by way of limitation.

EXPERIMENTAL

Example 1

Generation and Characterization of Lipid/Calcium Phosphate (LCP) Nanoparticles

Calcium phosphate (CaP) is frequently used as a non-viral vector for in vitro transfection of a wide variety of mammalian cells with little toxicity (Sokolova and Epple (2008) *Angew Chem Int Ed Engl* 47 (8):1382-1395). The delivery activity is probably related to the fact that CaP precipitates rapidly dissolve in acidic pH (Bisht et al. (2005) *Int J Pharm* 288 (1):157-168). An endocytosed CaP precipitate is believed to de-assemble in the endosomes and release its cargo into the cytoplasm. Previous attempts to improve the manufacture or efficiency of CaP precipitates have led to limited success (Olton et al. (2007) *Biomaterials* 28 (6): 1267-1279). The studies presented herein describe the generation and characterization of lipid-coated calcium phosphate precipitates, which are referred to herein as liposome/calcium phosphate (LCP) nanoparticles. LCP nanoparticles are similar to the previously described liposome-protamine-DNA (LPD) nanoparticles except the core is replaced with a biodegradable nano-sized calcium-phosphate precipitate (Li, Chono, and Huang (2008) *J Control Release* 126 (1):77-84).

Materials and Methods

Materials. 1,2-dioleoyl-3-trimethylammonium-propane chloride salt (DOTAP), cholesterol, 1,2-distearoryl-sn-glycero-3-phosphoethanolamine-N-[methoxy(polyethyleneglycol-2000) ammonium salt (DSPE-PEG) were purchased from Avanti Polar Lipids, Inc. (Alabaster, Ala.). DSPE-PEG-anisamide was synthesized as previously described (Banerjee et al. (2004) *Int J Cancer* 112 (4):693-700). Fura-2 acetoxymethyl ester (Fura-2 AM) was purchased from Invitrogen Inc. (Carlsbad, Calif.) and dissolved in DMSO to prepare a 1 mM stock solution. Anti-luciferase siRNA (target sequence 5'-CTT ACG CTG AGT ACT TCG A-3'; SEQ ID NO: 1) was purchased from Dharmacon (Lafayette, Colo.) in a deprotected, desalted, annealed form. Other chemicals were obtained from Sigma-Aldrich (St. Louis, Mo.) without further purification.

NCI-H-460 cells (human lung cancer cells) that were previously shown to be sigma-1 receptor positive (Chen et al. (2009) *Mol Pharm* 6 (3):696-705) were obtained from American Type Culture Collection and were stably transduced with a GL3 firefly luciferase gene using a retroviral vector. The cells were maintained in RPMI 1640 cell culture medium with 10% fetal bovine serum (Invitrogen, Carlsbad, Calif.), 100 U/ml penicillin, and 100 µg/ml streptomycin (Invitrogen, Carlsbad, Calif.).

Experimental animals. Female athymic nude mice of age 6-8 weeks were purchased from Charles River Laboratories (Wilmington, Mass.). All work performed on animals was in accordance with and approved by the University of North Carolina Institutional Animal Care and Use Committee.

Preparation of liposome/calcium phosphate (LCP) nanoparticles. FIG. 1 provides an illustration of the process used for the preparation of the liposome/calcium phosphate (LCP)NP. Briefly, 250 mM $CaCl_2$ and 250 mM $NaHPO_4$ aqueous solutions were prepared and the pH value of the solutions was adjusted by 1 M ammonium to pH 9. One hundred and fifty µl of the 250 mM $CaCl_2$ solution, 100 µl of the $NaHPO_4$ solution, and 25 µl anti-luciferase siRNA (2 mg/ml) were dispersed in 7 ml cyclohexane/Triton-X100/hexanol (7.5:1.8:1.7; v/v/v) to form a reverse water-in-oil micro-emulsion. After mixing the above solution for 15 min, 125 µl of 15 mM sodium citrate was added dropwise to the micro-emulsion. Notably, the solution remained transparent, and was, therefore, essentially free of large aggregates. After an additional incubation for another 15 min, 1 g of silica gel (60-200 mesh) was added to absorb the formed calcium phosphate nanoprecipitate with the entrapped siRNA. The silica gel was washed with ethanol and the precipitate was eluted with ethanol/water (25/75 vol/vol ratio).

The recovered nanoparticle core was dispersed in water after removing ethanol and mixed with a 1:1 mole/mole ratio of DOTAP-cholesterol (10 mM total lipid) liposome (that had been extruded by a 100 nm membrane) to form unmodified LCP nanoparticles. The amount of DOTAP in the resultant nanoparticle was optimized by detecting the zeta potential of the LCP nanoparticles in 1 mM KCl with a Zeta Plus potential analyzer (Brookhaven Instrument Corporation, Holtsville, N.Y.). The average size of the unmodified LCP nanoparticles was measured with a submicron particle sizer (NICOMP particle sizing system, AutodilutePAT Model 370, Santa Barbara, Calif.).

To qualitatively calculate the trapping efficiency of siRNA in the LCP nanoparticles, the anti-luciferase siRNA was replaced with a carboxyfluoroscein (FAM)-labeled siRNA having the same sequence (Dharmacon Inc, Lafayette, Colo.). The FAM-labeled siRNA LCP nano-particles were dissolved in lysis buffer (2 mM EDTA and 0.05% Trixton-100 in pH 7.8 Tris buffer) for quantitative analysis of the siRNA encapsulation efficiency. Standard siRNA solutions were prepared by diluting the FAM-labeled siRNA in the same lysis buffer. Then, 100 μl of the standard siRNA solution or the LCP solution was added to a 96-well plate and the fluorescence intensity was measured at 525 nm with a plate reader (Plate Chameleon Multilabel Detection Platform, Bioscan Inc., Washington D.C.). The amount of entrapped siRNA in the LCP nanoparticles was calculated based on the standard calibration curve.

Transmission electron microscope (TEM) images of the calcium phosphate (CaP) precipitate core and LCP nanoparticles were acquired with a JEOL 100CX II TEM (JEOL, Japan). Briefly, 5 μl of the CaP nanoprecipitate was dropped onto a 300 mesh carbon coated copper grid (Ted Pella, Inc., Redding, Calif.). For imaging of the LCP nanoparticles, 1% uranyl acetate was used to stain the nanoparticles for 5 min before observation with TEM.

Untargeted LCP and targeted LCP nanoparticles were prepared by incubating 330 μl unmodified LCP (10 mM lipid) with 37.8 μl DSPE-PEG2000 or DSPE-PEG2000-anisamide (10 mg/ml), respectively, at 50° C. for 10 min, followed by a 10 min incubation at room temperature before use. Liposome-protamine-DNA (LPD) nanoparticles were prepared as previously described (Li, Chono, and Huang (2008) *J Control Release* 126 (1):77-84).

Measurement of calcium release in live cells by LCP nanoparticles. Two μl of 2 mM Fura-2 AM and 2 μl of 20% Pluronic-127 were mixed for 5 min and added to 1 ml phenol red free DMEM cell culture medium before use. About $5\times10^4$ H-460 cells were incubated in a Lab-Tek 8-well glass chamber slide system (Fisher, Pittsburgh, Pa.) for 24 h. Two hundred μl of a 2 μM Fura-2 AM solution was added to the cell culture chamber, followed by a 50 min incubation. After washing two times with PBS, the cells were incubated in phenol red-free DMEM cell culture medium and imaged with a Nikon TE2000U microscope and OrcaER camera. Emission was monitored at 510 nm with an alternating excitation wavelength of 340 nm and 380 nm from a Xenon light source. After adding 50 μl of LCP nanoparticles, fluorescence image was obtained by setting the excitation wavelength at 340 nm for green color and 380 nm for red color. The ratio of 340 nm/380 nm was proportional to the intracellular free $Ca^{2+}$ concentration (Hirst et al. (1999) *Methods Mol Biol* 114:31-39). All experiments were performed at room temperature.

To study the inhibition of endocytosis, 20 mM cytochalasin D was prepared in DMSO solution and freshly diluted 1,000 times by phenol red-free DMEM medium for use. After incubating with Fura-2 AM for 60 min and 20 μM cytochalasin D for 5 min, cells were imaged as described in the presence of LCP nanoparticles.

In vitro luciferase gene silencing. H-460 cells stably expressing luciferase were seeded in 96 well plates. After reaching 60% confluency, different formulations of LCP nanoparticles containing anti-luciferase siRNA were added to the culture medium and the cells were incubated at 37° C. for 24 h. The siRNA was FAM-labeled and calibrated according to the method described herein above. Cells were washed twice with PBS followed by an incubation with 100 μl lysis buffer at 4° C. for 1 h. Twenty μl lysate was mixed with 80 μl luciferase substrate (Luciferase Assay System, Promega Co., Madison, Wis.) and the luminescence intensity was measured with a plate reader (Bioscan Inc., Washington D.C.). The total protein concentration in the lysate was determined with a protein assay kit (MicroBCA protein assay kit, Pierce). Luciferase activity is described as the luminescence intensity per μg protein.

In vivo luciferase gene silencing. H-460 cells ($2\times10^5$) expressing luciferase were subcutaneously injected into the lower back of female nude mice (about 20 g), and allowed to grow to a tumor size of about 400 $mm^3$. The mice were randomly assigned to different treatment groups (n=3 for each group). Mice were tail-vein injected with LCP-PEG or LCP-PEG-AA containing 24 μg anti-luciferase siRNA or a control siRNA, the target sequence of which is 5'-AAT TCT CCG AAC GTG TCA CGT-3' (SEQ ID NO: 2; Li, Chono, and Huang (2008) *J Control Release* 126 (1):77-84). LPD formulations containing the identical amount of anti-luciferase or control siRNA were also prepared and used for comparison. After 24 h, the tumors were harvested, weighed, and homogenized in lysis buffer with a ratio of volume of lysis buffer (ml)/tumor weight (g) of 2. Luciferase activity was measured as described for the in vitro study.

Immunotoxicity Assay. C57BL/6 mice were i.v. injected with targeted LCP or LPD nanoparticles with the amount of entrapped anti-luciferase siRNA at 0.6 mg/kg and 1.2 mg/kg. Four hours after the injection, blood samples were collected from the tail artery and incubated at room temperature for 0.5 h to allow for coagulation. Serum was obtained by centrifuging the clotted blood at 13,000 rpm for 20 min. Cytokine levels were determined with ELISA kits for IL6 and IL12 (BD Biosciences, San Diego, Calif.).

Results

Figure 3A:
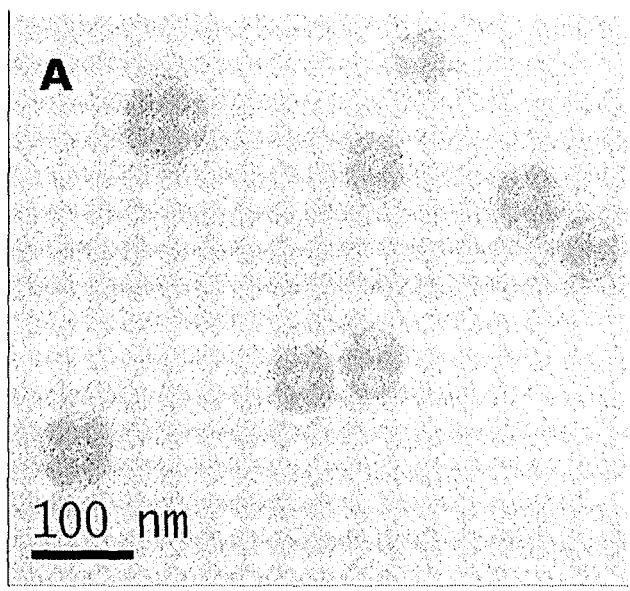
FIG. 3A and FIG. 3B show transmission electron microscopy (TEM) images of siRNA entrapped in a calcium phosphate (CaP) precipitate (FIG. 3A) or the liposome/calcium phosphate (LCP) nanoparticle with negative staining (FIG. 3B).

To encapsulate siRNA in nano-scale sized particles, the nucleic acid should be confined to a nano-sized space during particle assembly. A water-in-oil microemulsion has been used to entrap siRNA by calcium phosphate precipitate in a nano-sized reactor. Furthermore, in order to coat the nanoprecipitate with positively charged liposomes, the precipitate should have a negatively charged surface. The precipitate surface was negatively charged through the addition of citrate to the microemulsion (Morgan (2008) *Nano Lett* 8 (12):4108-4115). The organic solvent and surfactant were then removed from the formulation by immobilizing the CaP nanoprecipitate in silica gel and extensively washing with EtOH and water. The resultant spherically shaped CaP nanoprecipitate (FIG. 3A) was fairly homogenous with an average diameter of about 60-80 nm. As an alternative to the silica gel, EtOH or acetone was added to the micro-emulsion followed by centrifugation in an attempt to separate the nanoprecipitate from the surfactants; however, relatively large precipitates were formed due to aggregation of the nanoprecipitate (data not shown). While not being bound by any theory or mechanism of action, it is believed that the addition of citrate also served to stabilize the CaP nanoprecipitate. In this particular experiment, 15 mM citrate was used, which resulted in a CaP nanoprecipitate having a zeta potential of about −14 to about −20 mV. Thus, the resulting negatively charged CaP nanoprecipitates could be enveloped by cationic liposomes to form the LCP nanoparticles.

Figure 3B:
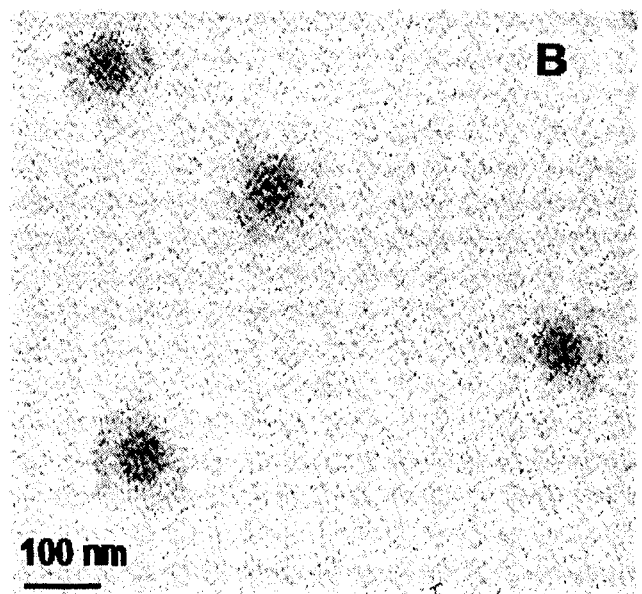
Figure 4:
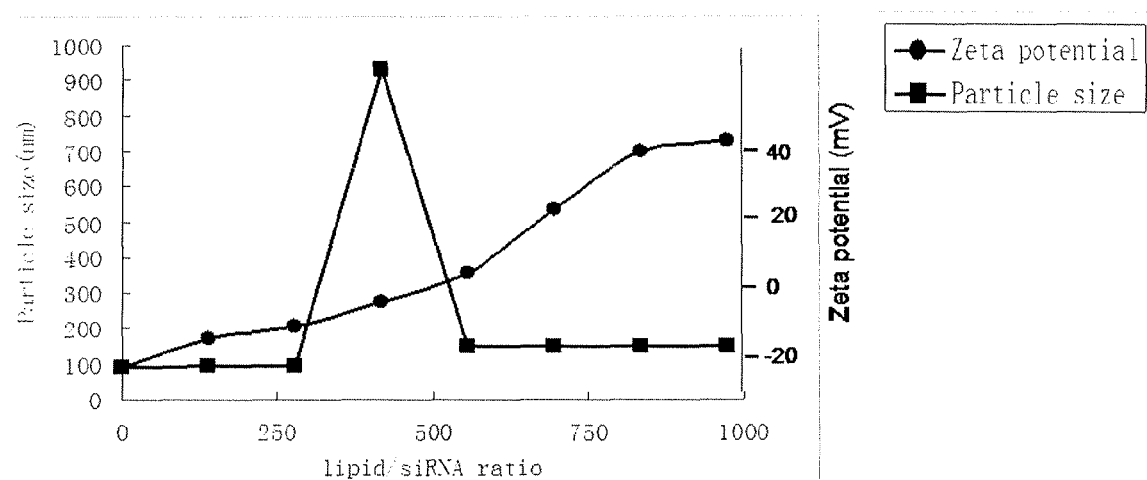
FIG. 4 provides a graph showing the effect of the molar ratio of lipid/siRNA on particle size and zeta potential of the LCP nanoparticle.

The average particle size and zeta potential of the LCP nanoparticles depend on the ratio of DOTAP/cholesterol liposome to CaP nanoprecipitate. As shown in FIG. 4, the CaP nanoprecipitate in this representative experiment was about 80 nm in diameter with a zeta potential of about −16 mV. The addition of more DOTAP/cholesterol liposome led to an increase in the zeta potential of the complex until a neutrally charged, yet very large aggregate (900 nm), formed at the molar ratio (mole/mole) of DOTAP/cholesterol: siRNA of about 417. With the addition of more DOTAP/ cholesterol liposome, the resultant complexes had a positive charge and stable colloids with a size of approximately 150 nm were obtained. The surface charge continuously increased to +38 mV with a stable size of about 150 nm until the molar ratio of DOTAP/cholesterol:siRNA reached about 834. To assure the CaP nanoprecipitate was fully enveloped by the liposome, a slight excess of lipids was used (a molar ratio of lipids:siRNA of 973) and the final particles had a zeta potential of about +40 mV and an average diameter of about 150 nm. With negative staining, TEM imaging showed a coating layer surrounding the calcium phosphate core (FIG. 3B), i.e. LCP nanoparticle, was obtained. Using a fluorescently-labeled siRNA, the final encapsulation efficiency of siRNA in LCP nanoparticles was measured to be 39.8±2.8% (n=3).

Figure 2:
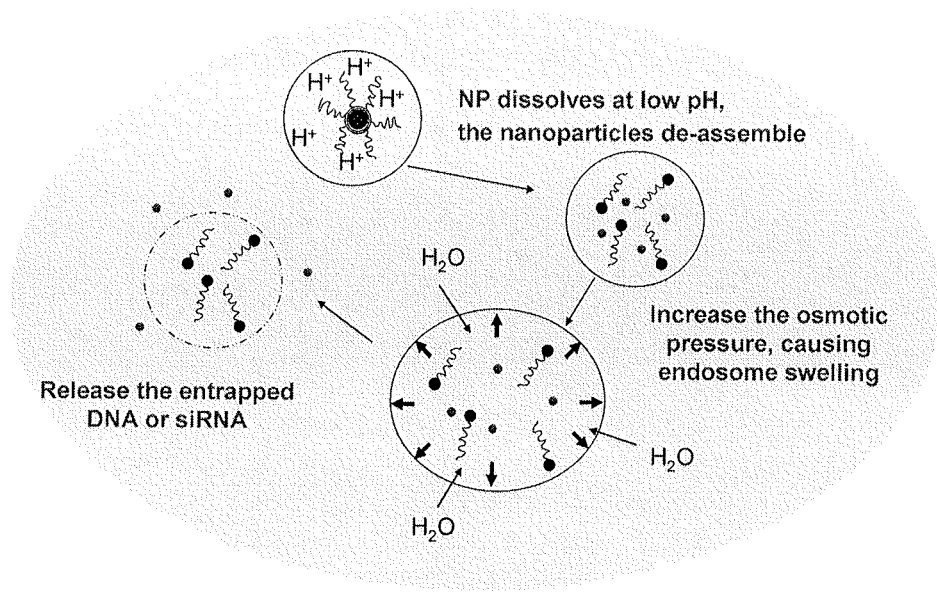
FIG. 2 depicts the proposed mechanism of the release process of siRNA or other bioactive compounds entrapped in the presently disclosed delivery system complexes following endocytosis into the endosome. There are four proposed steps for bioactive compound release from the delivery system complexes: (1) the delivery system complex enters the cell through endocytosis and is located within an endosome; (2) the precipitate core dissolves at low pH, leading to nanoparticle de-assembly; (3) the dissolved precipitate ions increase the osmotic pressure and cause endosome swelling; and (4) the endosome bursts and releases the bioactive compound (e.g., DNA, siRNA) and precipitate ions into the cytoplasm.
Figure 5A:
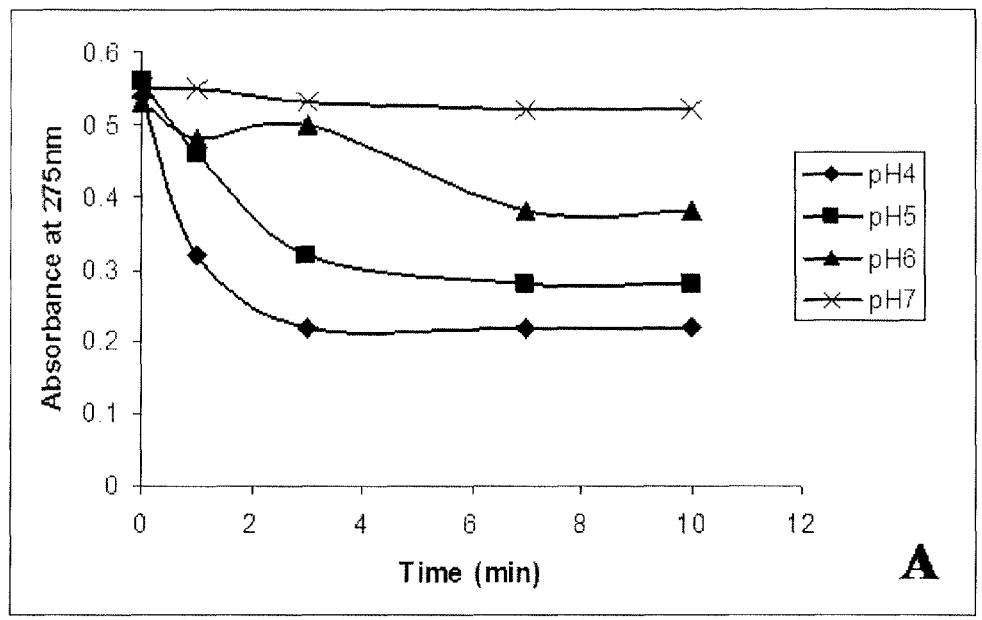
FIG. 5A and FIG. 5B provide graphs showing the light scattering of CaP/siRNA (FIG. 5A) and siRNA in LCP nanoparticles (FIG. 5B) at different pH levels.

It is well known that CaP precipitates rapidly dissolve at an acidic pH, releasing calcium ions. Protons should be able to penetrate the lipid membrane of LCP nanoparticles to dissolve the CaP core. Without being bound to any theory or mechanism of action, the CaP core is believed to dissolve under the acidic conditions of endosomes, releasing free anions and cations which increases the osmotic potential of the endosomes, leading to eventual bursting of the endosomes and release of the siRNA (see FIG. 2). The colloid CaP precipitate and LCP nanoparticles exhibited a light scattering absorbance at 275 nm and 270 nm, respectively. The dynamic change of light scattering at different pH levels was tested, as shown in FIG. 5A. At neutral pH 7.0, the light scattering of both CaP and LCP remained unchanged during the period of time which they were observed (10 min). When the pH was reduced to 6.0, 30% of the CaP nanoprecipitates disappeared after 10 min, but no substantial changes were observed for the LCP nanoparticles. With a further reduction in the pH level to 5.0, the light scattering of LCP nanoparticles decreased 60% in 10 min, showing significant acid-sensitivity. It is well known that the pH value in the endosomes of tumor cells can be as low as 5.0. Thus, the LCP NP should de-assemble at this pH and release its cargo, i.e., siRNA.

Figure 5B:
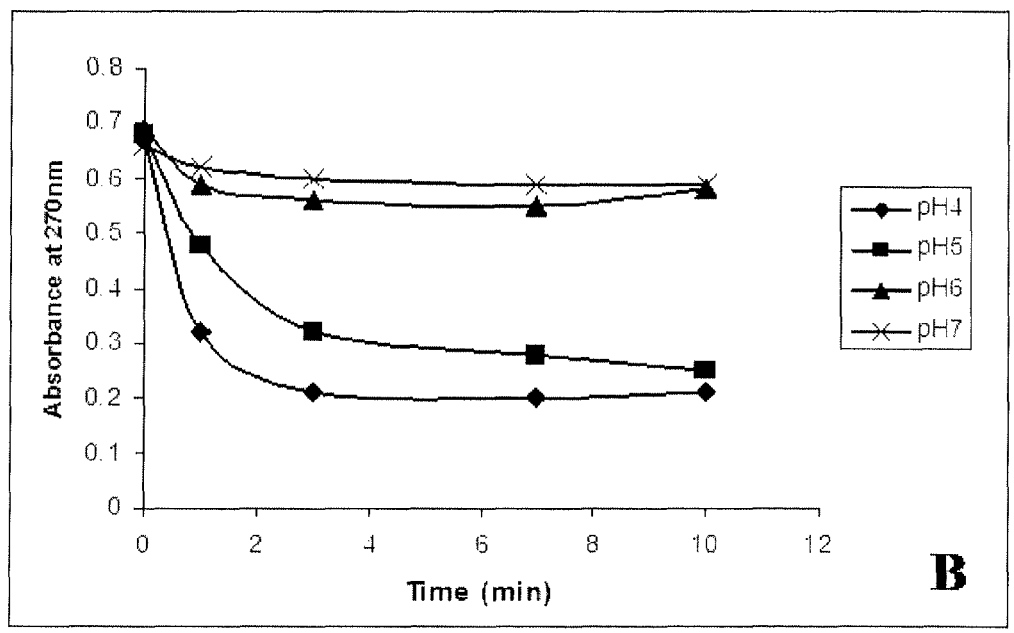
Figure 6A:
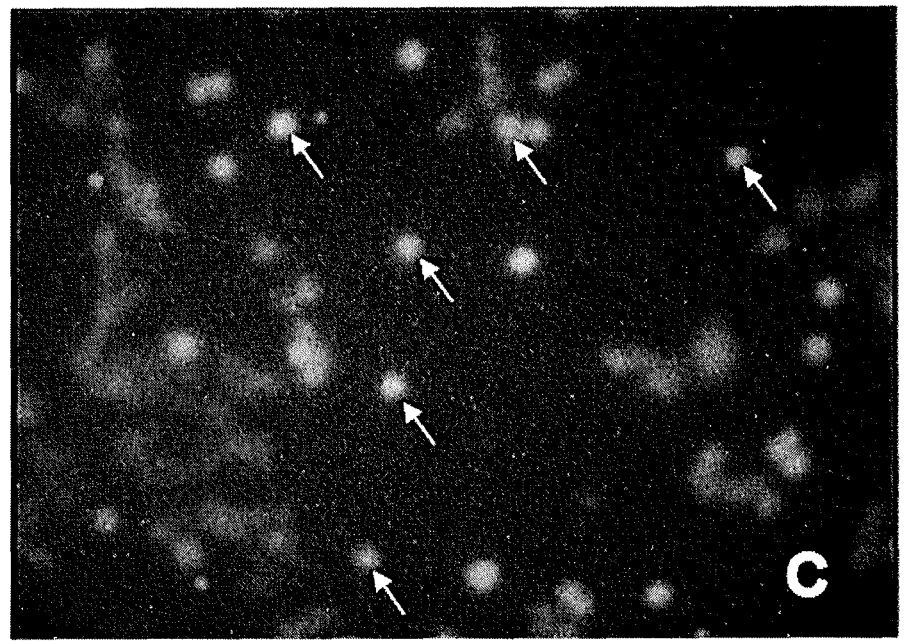
FIG. 6A and FIG. 6B provide fluorescent images of Fura-2-labeled H-460 cells before (FIG. 6A) and after (FIG. 6B) the addition of LCP nanoparticles. The arrows indicate cells that changed color from red (low Ca$^{2+}$) to green (high Ca$^{2+}$).
Figure 6B:
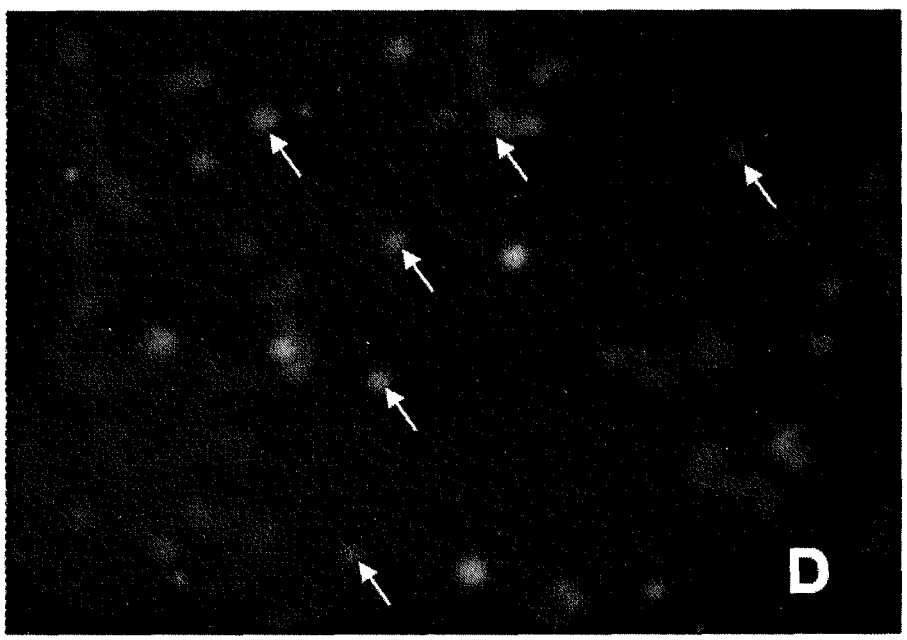

Fura-2-acetoxymethyl ester (Fura-2 AM) is a membrane-permeable derivative of Fura-2 that can be used to measure cellular calcium concentrations by fluorescence imaging. After entering the cell, Fura-2 AM is converted to Fura-2 by cellular esterase. Fura-2 binds to intracellular free calcium and blue-shifts its emission (Hirst (1999) *Methods Mol Biol* 114:31-39). The ratio of the emissions at 340 nm and 380 nm is directly correlated to the amount of intracellular calcium (Wier, Beuckelmann, Barcenas-Ruiz (1988) *Can J Physiol Pharmacol* 66 (9):1224-1231). After loading with 2 µM Fura-2 AM, tumor cells were incubated with unmodified LCP nanoparticles and imaged by confocal microscopy as shown in FIG. 5B. A significant color change was observed in the cells after the addition of LCP nanoparticles. White arrows indicate representative cells changing color from orange/red (low calcium) to green (high calcium). Since unmodified LCP nanoparticles are positively charged, it was possible that the color change of the cells was the result of interacting with cationic particles. This was tested by adding DOTAP/cholesterol liposomes (+40 mV in zeta potential) to Fura-2 labeled cells. The liposomes did not cause any color change, thus ruling out this possibility (data not shown). To verify that the color change resulted from the release of calcium in LCP, an endocytosis inhibitor, cytochalasin D, was used to inhibit the endocytosis of LCP nanoparticles in the tumor cells. The addition of cytochalasin D significantly reduced the color change from orange/red to green, verifying that the uptake of LCP nanoparticles was endocytosis-dependent (data not shown).

Figure 7A:
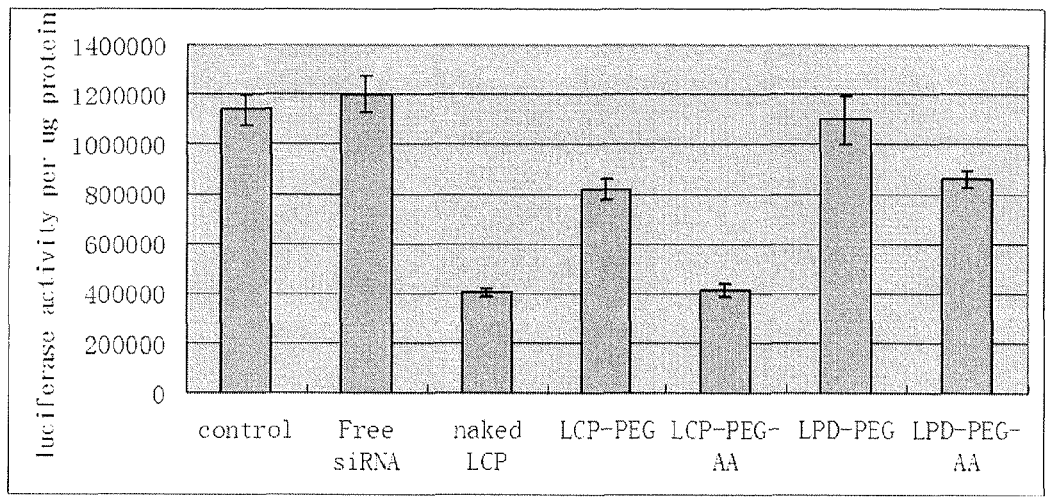
FIG. 7A and FIG. 7B provide graphs showing the in vitro luciferase gene silencing effect of different formulations in H-460 cells following an incubation at 37° C. for 24 h (n=5). The amount of siRNA in the LCP formulation was 99.8±6.9 nM, as measured by evaluating the entrapped fluorescently-labeled siRNA. For the lipid/protamine/DNA (LPD) formulations, the concentration of FAM-labeled siRNA was 100 nM.
Figure 7B:
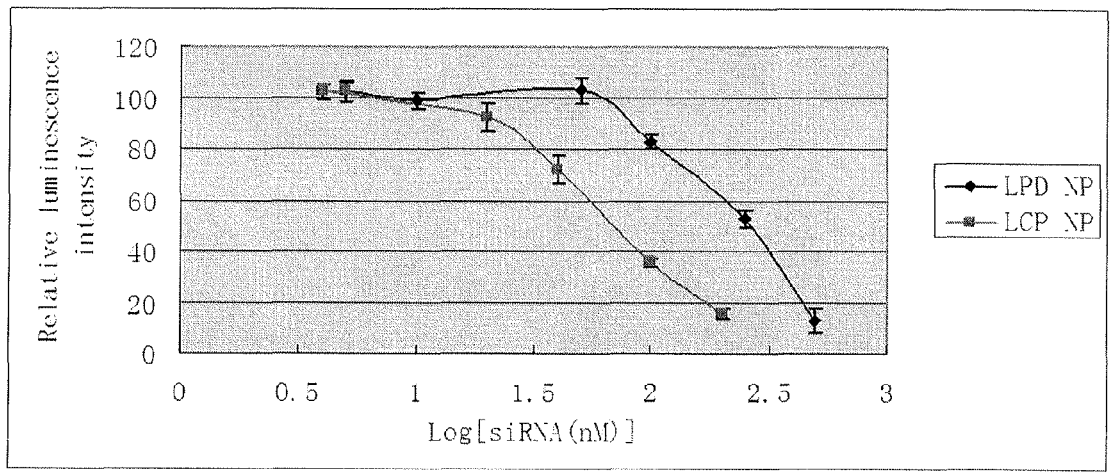

The in vitro gene silencing effect of the LCP nanoparticles was studied with H-460 cells stably expressing firefly luciferase. FIG. 7A shows the silencing effect of anti-luciferase siRNA in different formulations. Free siRNA does not have any silencing effect due to its inability to penetrate the lipid membrane of cells. The naked or unmodified LCP nanoparticle formulation resulted in a large silencing effect, but it was also relatively toxic, presumably due to its cationic charges. The addition of PEGylated, but untargeted, LCP (LCP-PEG) nanoparticles led to a 20% silencing effect probably because the reduction in the positive charge of the LCP nanoparticles reduced the level of endocytosis. In comparison to the untargeted PEGylated LPD formulation (LPD-PEG), the slight enhancement in silencing of the PEGylated LCP nanoparticles may be due to the solid calcium phosphate core. The anisamide (AA)-targeted LCP (LCP-PEG-AA) nanoparticles had a significantly improved silencing effect compared to PEGylated but untargeted LCP (LCP-PEG) nanoparticles, down-regulating more than 60% of the luciferase expression when the concentration of siRNA equaled 100 nM (n=3). The targeted LPD (LPD-PEG-AA) nanoparticles, however, only silenced 20% of the luciferase expression at the same concentration of the siRNA. FIG. 7B demonstrates that the LCP formulations consistently showed a stronger silencing effect than the corresponding LPD formulations. The $IC_{50}$, the half maximal inhibitory concentration, of siRNA in the LCP nanoparticles was calculated to be about 60 nM, which is three to four times lower than that of siRNA in the LPD (200 nM) nanoparticles.

Figure 8:
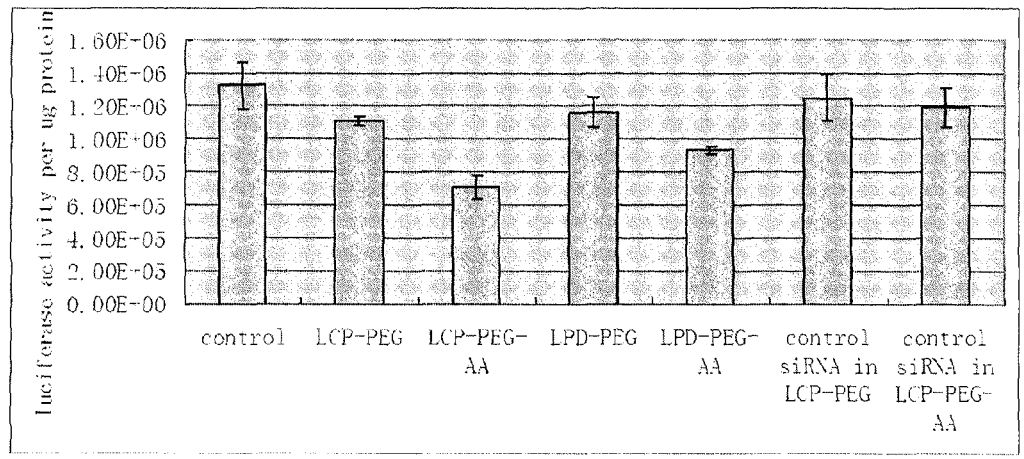
FIG. 8 provides a graph showing the in vivo luciferase gene silencing effects of different formulations at the siRNA dose of 1.2 mg/kg. The luciferase activity in H-460 cells was measured 24 hours after an i.v. injection of the various siRNA formulations.

The in vivo luciferase gene silencing effect of LCP nanoparticles was studied with a xenograft model by implanting H-460 cells into nude mice. As shown in FIG. 8, the PEGylated but untargeted LCP (LCP-PEG) nanoparticles showed a slight silencing effect in the expression of luciferase. However, the targeted LCP (LCP-PEG-AA) resulted in 50% down-regulation in luciferase expression, which was also similar to the corresponding LPD formulation. When the anti-luciferase siRNA was replaced with control siRNA, almost no silencing effect was observed in any formulation. Thus, LCP nanoparticles can be used to deliver siRNA in vivo.

Figure 9:
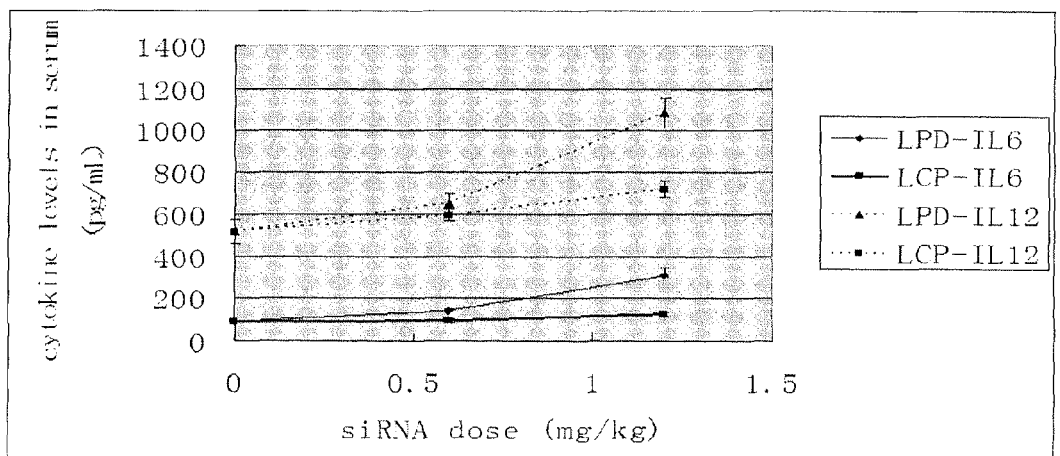
FIG. 9 provides a graph showing the serum IL-6 (solid line) and IL-12 (dash line) levels in mice 4 hours after an i.v. injection of targeted LCP (squares) or LPD (circles) formulations at different doses of siRNA.

The immunotoxicity of the targeted LCP and LPD formulations was investigated in C57BL/6 mice (FIG. 9). The serum concentration of two important pro-inflammatory cytokines, IL-6 and IL-12, was measured as previously described (Chono et al. (2008) *J Control Release* 131 (1):64-69; Li, Chono, and Huang (2008) *J Control Release* 126 (1):77-84). Administration of targeted LCP nanoparticles led to a relatively minor increase in IL-6 levels even at a siRNA dose of 1.2 mg/kg. There was no increase in IL-12 serum levels at a siRNA dose of 0.6 mg/kg and only a relatively slight increase at the dose of 1.2 mg/kg. Administration of the LPD formulation, however, resulted in an increase in IL-6 and IL-12 levels at the siRNA dose of 0.6 mg/kg, with a significant increase in IL-6 and IL-12 levels at the siRNA dose of 1.2 mg/kg. Therefore, siRNA delivery via the LCP nanoparticles allows for the delivery of larger doses of siRNA in the absence of significant immunotoxicity.

A novel LCP nanoparticle formulation has been developed that allows for the in vivo delivery of siRNA or other bioactive compounds. The calcium phosphate in the core of LCP nanoparticles dissolves at low pH in the endosome, leading to an increase in the osmotic pressure, endosome swelling, and eventually endosome bursting to release the entrapped siRNA. The targeted LCP nanoparticles with a PEG coating displayed an improved gene silencing effect in vitro over the previously described LPD formulations (Li, Chono, and Huang (2008) *J Control Release* 126 (1):77-84). In comparison to LPD nanoparticles, the replacement of the DNA/protamine complex core with a calcium phosphate precipitate also reduced the immunotoxicity of these nanoparticles.

Example 2

Figure 10:
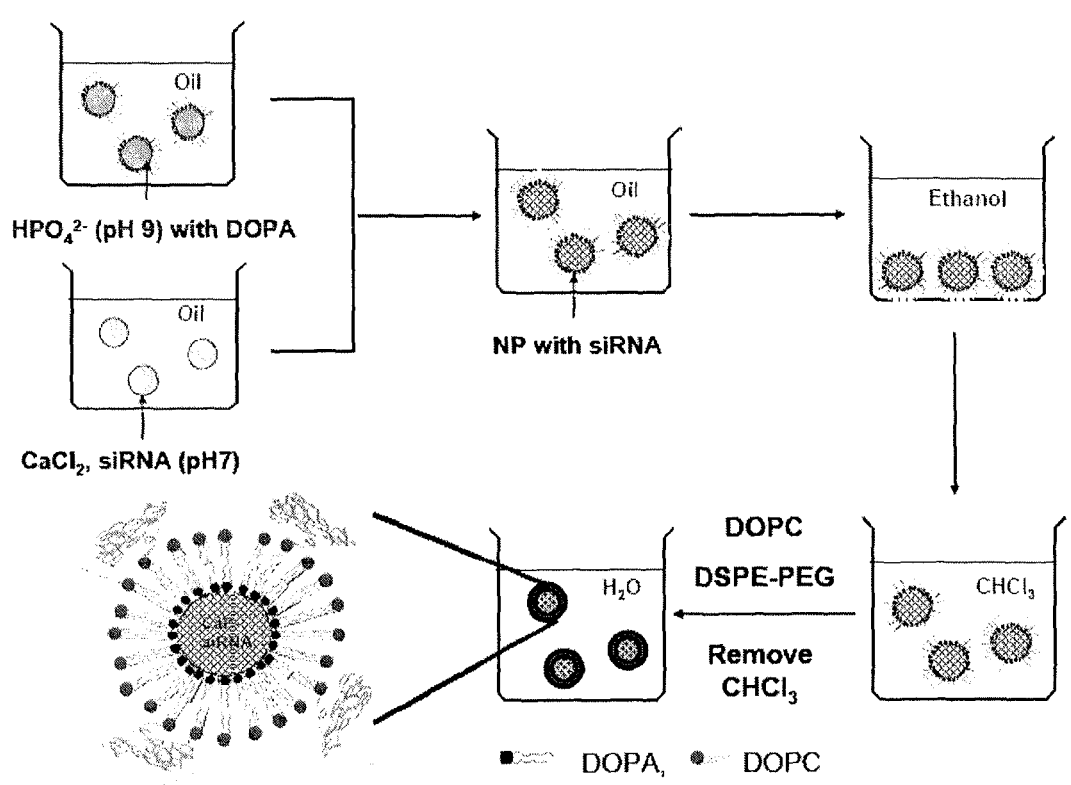
FIG. 10 provides a depiction of the preparation of a non-limiting embodiment of the presently described LCP-II nanoparticles encapsulating siRNA. Two reverse microemulsions containing calcium chloride (CaCl2) and sodium phosphate (Na2HPO4), respectively, are mixed. The calcium chloride microemulsion comprises the siRNA and has a pH of 7 and the sodium phosphate microemulsion comprises dioleoyl phosphatidic acid (DOPA) and has a pH of 9. The calcium phosphate (CaP) precipitate that forms is washed with ethanol and the precipitate is pelleted. The CaP precipitate is then solubilized in chloroform (CHCl3). The lipids dioleoyl phosphatidylcholine (DOPC) and 1,2-distearoyl-sn-glycero-3-phosphoethanolamine-N-carboxy-polyethylene glycol-anisamide (DSPE-PEG-AA) is added to the solution and then the chloroform is evaporated and the nanoparticle is dispersed in an aqueous solution.

Generation and Characterization of Lipid/Calcium Phosphate (LCP)-II Nanoparticles Lipid/calcium phosphate nanoparticles having a hollow core have been generated and are referred to herein as LCP-II nanoparticles. FIG. 10 describes the procedure with which LCP-II nanoparticles are prepared. Two separate reverse microemulsions containing calcium chloride ($CaCl_2$) and sodium phosphate ($Na_2HPO_4$), respectively, are mixed. The microemulsion containing the phosphate is stabilized with an amphiphilic lipid having a free phosphate group, such as the phospholipid dioleoyl phosphatidic acid (DOPA). The calcium chloride microemulsion (pH 7) comprises the siRNA or other water-soluble drug. The pH of the sodium phosphate microemulsion is brought to a pH of 9 through the addition of small amounts of NaOH, for example. When the two microemulsions are combined, a calcium phosphate (CaP) precipitate forms inside the microemulsion. The CaP cores are suspended in excess EtOH and centrifuged to pellet the CaP cores. After extensive washing with EtOH to remove surfactants, the CaP cores are solubilized in a volatile, organic solvent, such as chloroform ($CHCl_3$). Due to the coating with the amphiphilic lipid with the free phosphate group (e.g., DOPA), the CaP cores are soluble in the organic solvent (e.g., $CHCl_3$) and can be stored under these conditions at 4° C. for at least one month. A lipid is added to the solution and the organic solvent (e.g., $CHCl_3$) is evaporated. The lipid can be a neutral phospholipid (e.g., dioleoyl phosphatidylcholine; DOPC). The residue is then resuspended in water to generate the final LCP-II nanoparticle preparation.

A PEGylated lipid (DSPE) conjugate, with or without a targeting ligand anisamide (AA), can also be added together with the lipid (e.g., DOPC), for example, with a mol ratio of DOPC to DSPE-PEG (AA) of 9. The PEGylated lipid is added to protect the surface of the nanoparticle from protein binding in the blood. The anisamide ligand serves to bind the nanoparticle to the sigma receptor that is over-expressed in many different human cancer cells.

Figure 11A:
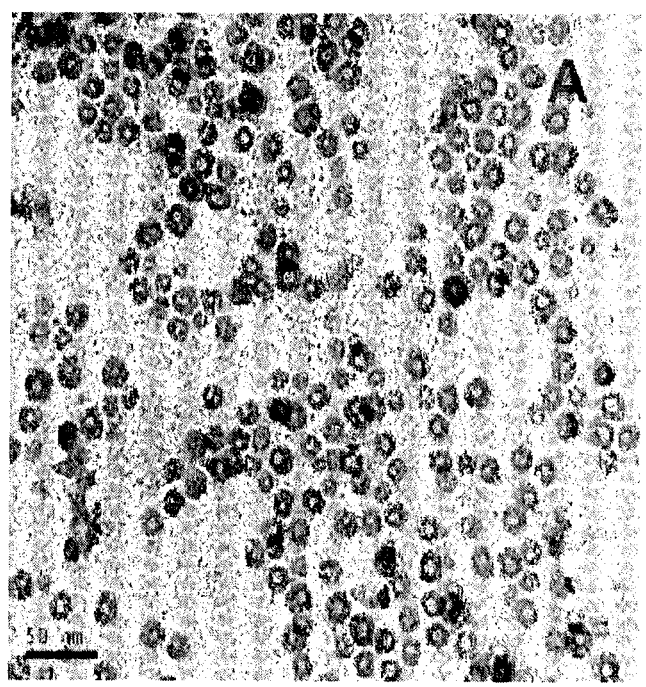
FIG. 11A and FIG. 11B show transmission electron micrographs of LCP-II nanoparticles. The LCP-II nanoparticles of FIG. 11A are unstained, whereas the LCP-II nanoparticles of FIG. 11B have been negatively stained with uranyl acetate.
Figure 11B:
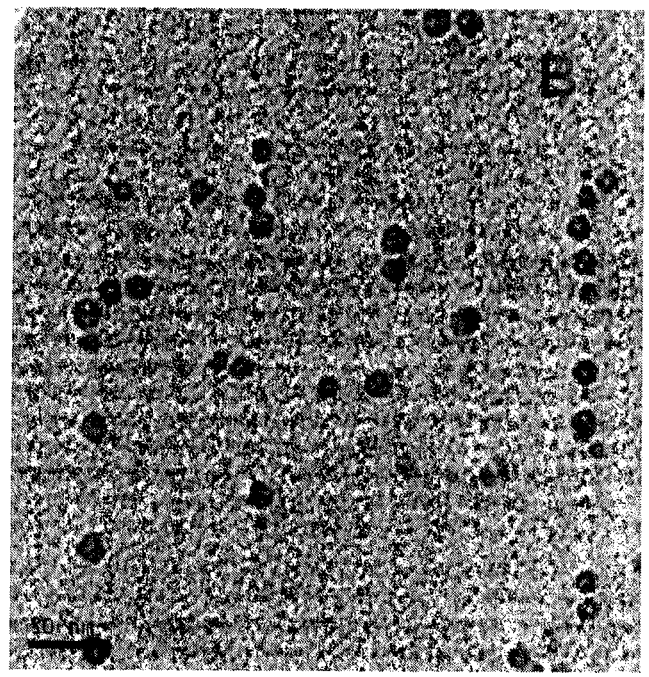
Figure 12:
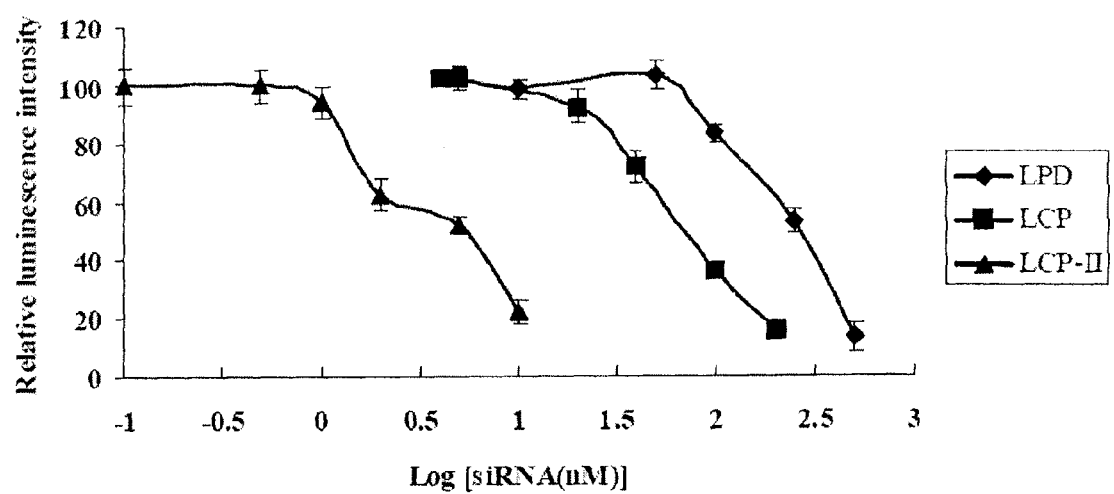
FIG. 12 provides a graph demonstrating the in vitro silencing effect of anti-luciferase siRNA in LCP-II, LCP, and LPD nanoparticles. NCI-H460 cells retrovirally transduced with the firefly luciferase cDNA were incubated with the nanoparticles having the indicated concentrations of siRNA for 24 hours and the luciferase activity of the treated cells was measured with a luminometer and is displayed on the y-axis as relative luminescence intensity.
Figure 13:
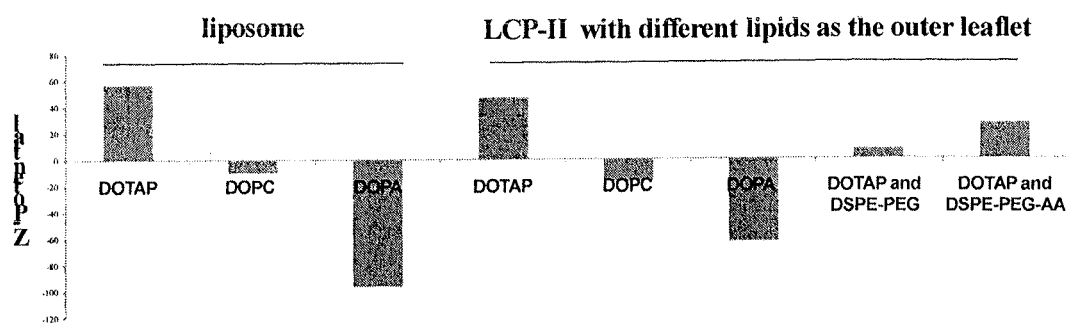
FIG. 13 depicts an asymmetric structure of a LCP-II formulation. Different lipids were chosen as the outer leaflet lipids and the zeta potentials of the resulting nanoparticles were measured. As a comparison, liposomes composed of the pure lipid used as the outer leaflet lipid were also prepared and their zeta potentials also measured. The data indicate that the coating bilayer of LCP-II is asymmetric in lipid composition. The zeta potential of pure DOPA liposome was −90 mV and that of pure DOPC liposome was −10 mV. The zeta potential of LCP-II coated with DOPC was −17 mV, which was similar to the value of DOPC and indicated that the outer leaflet lipid was DOPC, not DOPA (the inner leaflet lipid). DOTAP as the outer leaflet coating has a zeta potential of +45 mV, which is similar to that of DOTAP liposome (+55 mM), indicating that the outer leaflet lipid was DOTAP, not DOPA. When the DOTAP coated LCP-II formulation was modified with DSPE-PEG or DSPE-PEG-AA, the zeta-potentials were +7 mV and +24 mV, respectively. This results show that surface modification by DSPE-PEG and DSPE-PEG-AA can shield the positive charges of DOTAP on the outer leaflet of LCP-II, and substantially reduce the zeta potential. Taken together, the results showed the existence of an asymmetrical lipid membrane at the surface of LCP-II.
Figure 14A:
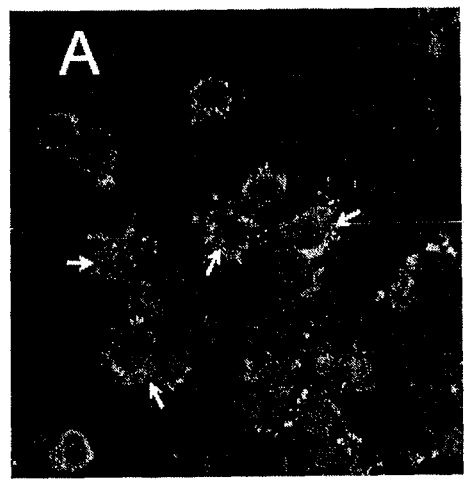
FIGS. 14A, 14B and 14C depict subcellular distribution of FITC-labeled dsDNA (model for siRNA) in H-460 cells. The ability of a LCP-II composition to release its cargo into the cytoplasm of the cell after endocytosis was shown by using a FITC-labelled double stranded oligo DNA (dsDNA) as a model for siRNA. The same labeled oligo DNA was encapsulated in the LPD nanoparticles (a formulation without an acid sensitive core) and used in the experiment for comparison. H460 cells were incubated with 50 nM dsDNA formulated with different formulations for 3 hours, fixed and examined by confocal microscopy.
Figure 14B:
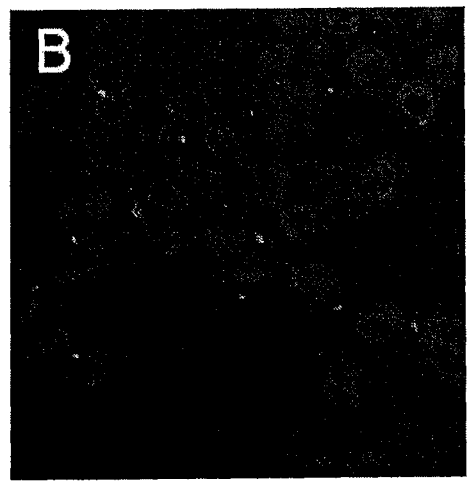
Figure 14C:
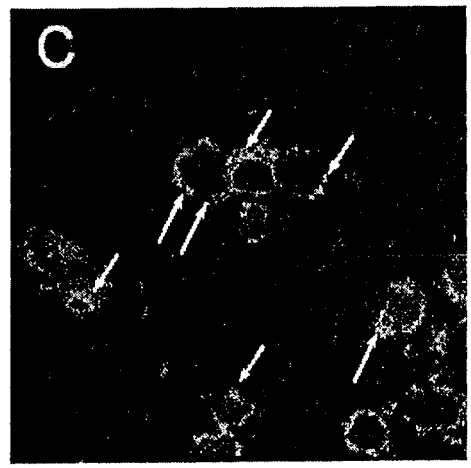
Figure 15:
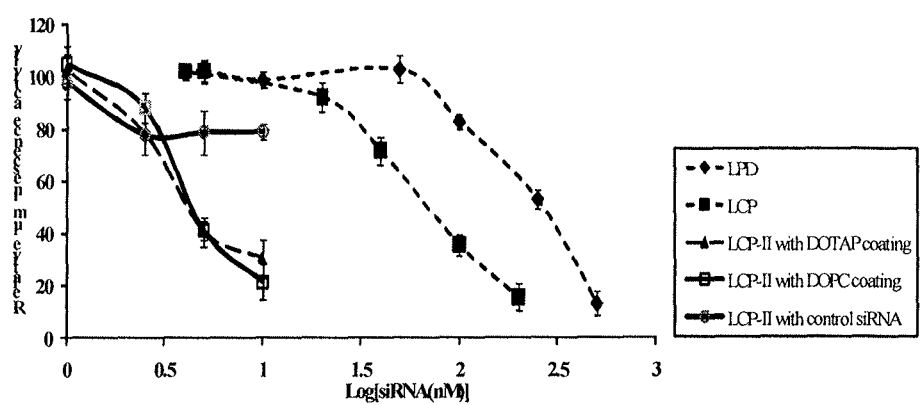
FIG. 15 depicts the silencing effect of siRNA formulated in LCP-II with different lipids as the outer leaflet lipid. Specifically, the in vitro silencing effect of luciferase siRNA encapsulated in different LCP-II formulations is shown. The formulations were LPD, LCP and LCP-II with DOTAP (dotted line) and DOPC (solid line) as the outer leaflet lipid. Data indicate that LCP-II was about 50-fold more active in delivering siRNA than LPD. H460 cells stably transduced with GL3 firefly luciferase gene were incubated with several formulations. After incubation for 24 hours with different concentrations of siRNA, cells were washed with PBS twice followed by incubation with 100 μl lysis buffer at 4° C. for 1 h. Twenty μl lysate was mixed with 80 μl substrate (Luciferase Assay System, Promega Co., Madison, Wis.) and the luminescence intensity was measured by a plate reader (Bioscan Inc., Washington D.C.). The total protein concentration in the lysate was determined by using a protein assay kit (Micro BCATM Protein Assay Kit, Pierce). The activity of luciferase is normalized by the protein concentration in the lysate and shown as percent activity of the untreated control (see FIG. 15). For comparison, the luciferase silencing activity of siRNA formulated in LCP (Li, J., Chen, Y-C., Tseng, Y-C., Mozumdar, S., and Huang, L. Biodegradable Calcium Phosphate Nanoparticle with Lipid Coating for Systemic siRNA Delivery, *J Control Release*, 2010, 142:416-421) and LPD (Li, S. D., Chono, S., Huang, L., Efficient gene silencing in metastatic tumor by siRNA formulated in surface-modified nanoparticles, *J Control Release*, 2008, 126 (1):77-84) nanoparticles. The data indicate that the delivery activity, as measured by luciferase silencing, was the highest for LCP-II. The activity of LCP was the second and LPD the last. The $ED_{50}$ values for these formulations were about 8, 60 and 200 nM of siRNA for LCP-II, LCP and LPD, respectively. Furthermore, there was no significant difference in the delivery activity for LCP-II containing DOTAP (cationic lipid) or DOPC (neutral phospholipid). LCP-II containing a control siRNA had minimal silencing activity. These results indicate that LCP-II is a potent delivery vehicle for siRNA in vitro. It represents a significant improvement in nanoparticle formulation over the previous formulations.
Figure 16:
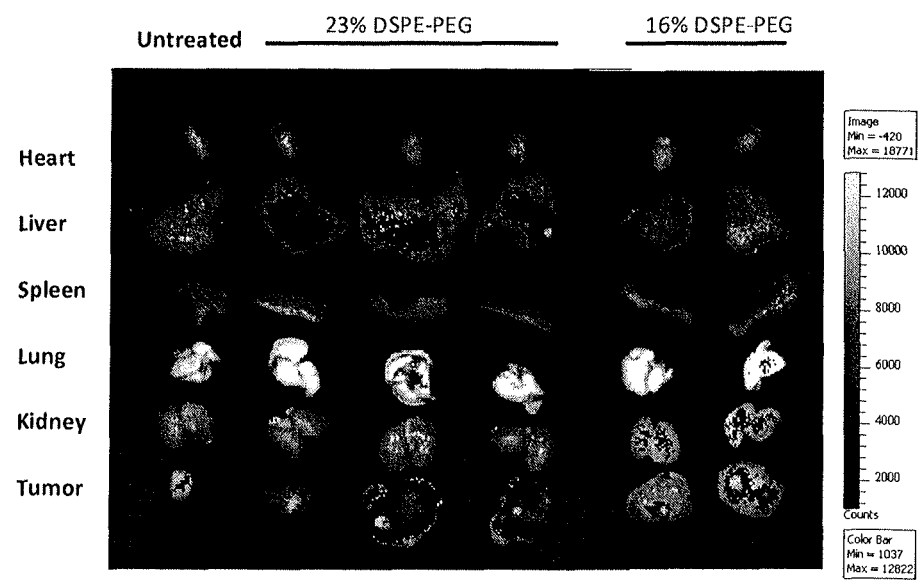
FIG. 16 depicts the biodistribution of fluorescence labeled siRNA delivered by LCP-II in tumor bearing mouse. LCP-II was coated with either 16 or 23 mol % of DSPE-PEG2000 and i.v. injected into nude mice bearing human H-460 tumors. Data indicate that LCP-II with 16 mol % PEGylation accumulated in the liver and but less in the tumor. LCP-II with 23 mol % PEGylation accumulated mainly in the tumor, not in the liver. The biodistribution of fluorescence labeled siRNA delivered by LCP-II was investigated in a xenograft model of H-460 human lung cancer. The effect of PEGylation on liver uptake and tumor uptake of siRNA formulated in the LPD nanoparticles was investigated (Li S D, Huang L., Nanoparticles evading the reticuloendothelial system: role of the supported bilayer, *Biochim Biophys Acta*, 2009, 1788 (10):2259-66). PEGylation for the LCP-II formulation was investigated by using different amounts of DSPE-PEG-2000 to coat the nanoparticles. The nanoparticles were intravenously injected to the tumor bearing mice. Four hours later, mice were sacrificed and major organs including the tumor were taken for imaging by using an IVIS imaging system. The results indicate that LCP-II requires at least 23 mol % of DSPE-PEG-2000 to protect the nanoparticle from the liver uptake and to significantly accumulate in the tumor. It is thought that the high surface curvature of the smaller particles (LCP-II ~30 nm) compared to the larger particles (LPD ~150 nm) may be contributing to the surprising level of PEGylation that is useful in this formulation.
Figure 17:
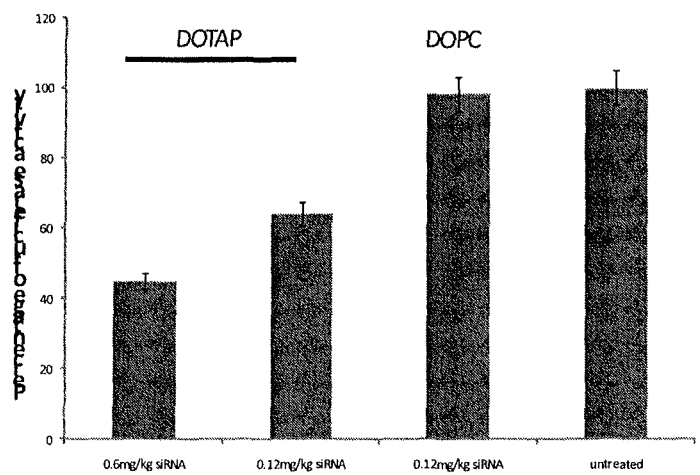
FIG. 17 depicts the in vivo silencing effect of luciferase siRNA delivered by LCP-II nanoparticles with different outer leaflet lipids in an H-460 human lung cancer model. The two columns from the left show a LCP-II formulation with DOTAP as the outer leaflet lipid. The third column shows LCP-II with DOPC as the outer leaflet lipid. The fourth is untreated control. The in vivo silencing effect of luciferase siRNA encapsulated in different LCP-II formulations was investigated by administration of the formulation to mice with H460 xenograft model. After 24 hours, the tumors were harvested, weighted and homogenized in lysis buffer. The luciferase activity in the tumor following steps were the same as the in vitro study described above for FIG. 15. As can be seen in FIG. 17, LCP-II with DOTAP as the outer leaflet lipid showed silencing activity, but the DOPC formulation shown was similar to the untreated control. Thus, preferably the nanoparticle comprises a cationic lipid.

FIG. 11 shows transmission electron micrographs of LCP-II nanoparticles. FIG. 11A shows LCP-II nanoparticles in the absence of staining. The LCP-II nanoparticles of FIG. 11A were then negatively stained with uranyl acetate (shown in FIG. 11B). In the absence of the stain, the membranes of the LCP-II nanoparticles are not visible (FIG. 11A). The cores, however, are clearly visible as hollow structures with an electron dense shell of approximately 4-6 nm in thickness. The inner space (approximately 15-20 nm in diameter) of the core is hollow and may be filled with water. With negative staining, the membranes of the LCP-II nanoparticles are clearly visible. The overall size of the LCP-II nanoparticles is 25-30 nm in diameter.

siRNA, a polyphosphate, can be entrapped in LCP-II by adding it to the phosphate microemulsion, for example, at approximately 10% of the total phosphate. The trapping efficiency is approximately 80%. FIG. 12 shows a dose response curve of target gene silencing. Human lung cancer NCI-H460 cells were stably transduced with retrovirus to introduce the firefly luciferase cDNA in the cells. siRNA against the luciferase (SEQ ID NO: 1) was encapsulated in three different nanoparticles, LPD nanoparticles (Li, Chono, Huang (2008) *J Control Release* 126 (1):77-84; Li et al. (2008) *Mol Ther* 16 (1):163-169, each of which are herein incorporated by reference in its entirety), LCP nanoparticles (as described elsewhere herein), and LCP-II nanoparticles; all of which were targeted with the same amount of DSPE-PEG-AA.

The cells were incubated with the nanoparticles for 24 hours and the luciferase activity of the treated cells was measured with a luminometer. As can be seen in FIG. 12, the $IC_{50}$ of the siRNA was 5 nM, 50 nM, and 200 nM in the LCP-II, LCP and LPD nanoparticles, respectively. Thus, the potency of siRNA delivered by LCP-II nanoparticles was about 10-fold greater than the LCP formulation, and about 40-fold greater as compared to LPD nanoparticle delivery.

Additionally, AraC monophosphate, gemcitabine monophosphate, and the peptide having the following amino acid sequence EEEEpYFELV, wherein the tyrosine (Y) is phosphorylated; SEQ ID NO: 3), could also be encapsulated in LCP-II nanoparticles with a trapping efficiency of about 94%, 88% and 82%, respectively. Without being bound by any theory or mechanism of action, it is believed that these water-soluble, phosphorylated drugs could participate in the CaP precipitation in the core. The negatively-charged fluorescent dye, sodium fluorescein, could also be encapsulated in LCP-II nanoparticle with a moderate efficiency of about 40%.

Without being bound by any theory or mechanism of action, it is believed that the hollow core, which is probably aqueous, of the LCP-II nanoparticle is formed because the calcium phosphate (CaP) precipitate grows inward beginning from the phosphate groups of DOPA at the interface of the microemulsion. When the CaP precipitate consumes all the available calcium and phosphate ions, the growth of the CaP shell stops, leaving the center of the CaP core hollow and most likely filled with water. It is believed that the remaining salts and sodium and chlorine ions are accumulated in the inner aqueous space. Thus, the osmotic pressure and the ionic strength of the aqueous core may be very high.

The membrane of the LCP-II nanoparticles generated herein is asymmetric in that the inner leaflet of the bilayer is enriched with the negatively charged lipid DOPA, but the outer leaflet is enriched with the neutral lipid DOPC. While not being bound by any theory or mechanism of action, it is believed that this energetically unfavorable state is stabilized because DOPA is ionically bonded to the surface of the CaP precipitate shell. The zeta potential of pure DOPA liposomes is −90 mV and that of pure DOPC liposomes is −10 mV. The zeta potential of the DOPA/DOPC LCP-II nanoparticles generated herein is −17 mV. These data are consistent with the existence of an asymmetrical lipid membrane at the surface of DOPA/DOPC LCP-II nanoparticles. Because of the small size of the nanoparticle, the surface lipid bilayer of the DOPA/DOPC LCP-II nanoparticles contains a very high curvature. It is known that the smallest lipid vesicles that can be formed in an aqueous solution are about 50 nm in diameter (Huang and Mason (1978) *Proc Natl Acad Sci USA* 75 (1):308-310). Anything smaller would pose a surface energy high enough to drive spontaneous fusion between the vesicles. The high curvature bilayer membrane of the DOPA/DOPC LCP-II nanoparticles is stabilized by the binding of the inner leaflet lipid DOPA with the CaP shell. It can be calculated that a bilayer of such high curvature should have a mass ratio of outer to inner leaflet lipid of approximately 2.6 (Enoch and Strittmatter (1979) *Proc Natl Acad Sci USA* 76 (1):145-149, which is herein incorporated by reference in its entirety).

LCP-II nanoparticles generated herein differ from LCP nanoparticles in at least the following aspects. First, LCP-II nanoparticles are much smaller than LCP nanoparticles, which are 100-200 nm in diameter. Second, LCP nanoparticles contain a solid CaP core with little to none internal aqueous space, whereas the LCP-II nanoparticle core is hollow and presumably filled with water. Third, LCP nanoparticles contain cationic lipids, but the LCP-II nanoparticles generated herein contain only negatively charged (DOPA) and neutral (DOPC) lipids. Fourth, the lipid membrane of LCP nanoparticles is symmetric in that the lipid composition of the inner and outer leaflets is the same. LCP-II nanoparticles generated herein contain an asymmetrical lipid membrane. Fifth, the PEGylated lipid conjugate was added after the LCP nanoparticle was already prepared in a procedure called postinsertion (Hoarau et al. (2004) *Pharm Res* 21 (10):1783-1789). With the LCP-II nanoparticles, however, the PEGylated lipid conjugate was added during the formation of the outer leaflet of the bilayer.

The application of LCP-II nanoparticles to drug and gene delivery is very broad. The LCP-II nanoparticles can be used for nucleic acid delivery as demonstrated in FIG. 12. The nanoparticles can also be used to deliver any water-soluble drugs to treat cancer, infectious diseases, inflammation, and cardiovascular disorders, for example. Because of the small size, LCP-II nanoparticles may be used to transport drugs to cross the blood brain barrier (BBB) into the CNS. Non-limiting examples of ligands that can be used to target the BBB include transferrin and lactoferrin (Huang et al. (2008) *Biomaterials* 29 (2):238-246, which is herein incorporated by reference in its entirety). Also, the LCP-II nanoparticles can be transcytosed across the endothelium into both skeletal and cardiac muscle cells. For example, the exon-skipping oligonucleotides can be delivered by LCP-II to treat Duchene muscular dystrophy (Moulton et al. (2009) *Ann N Y Acad Sci* 1175:55-60, which is herein incorporated by reference in its entirety).

Materials and Methods for Example 2

The LCP-II nanoparticles were generated using the methods depicted in FIG. 10. Briefly, 250 mM calcium chloride and 250 mM sodium phosphate aqueous solutions were prepared separately. The pH of the calcium chloride solution was adjusted to a pH of about 7. The pH of the sodium phosphate solution was adjusted to a pH of about 9. The drug (e.g., siRNA, peptide, AraC monophosphate, gemcitabine monophosphate) was added to the calcium chloride solution. A first reverse water-in-oil microemulsion was created by adding 300 µL of the calcium chloride solution with the drug to 15 ml cyclohexane/triton-X100/hexanol (78/11/11; v/v/v). A second reverse water-in-oil microemulsion was formed by adding 200 µL of the sodium phosphate solution and 200 µL 20 mM DOPA dissolved in chloroform to 15 ml cyclohexane/triton-X100/hexanol (78/11/11; v/v/v). The two microemulsions were then mixed together. After about 30 min, 15 ml of ethanol (EtOH) was added and the solution was centrifuged to pellet the calcium phosphate precipitate and to remove the organic solvent and surfactant. After washing a total of 3-4 times with ethanol, the calcium phosphate precipitate core was mixed with a 10:1 molar mixture of DOPC:DSPE-PEG-AA (10 mM total lipid) in chloroform. The chloroform was then evaporated with a stream of nitrogen gas. The nanoparticle formulation was then dissolved in water via sonication (few minutes).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. A delivery system complex comprising a biodegradable ionic precipitate wherein, said biodegradable ionic precipitate comprises, i. a salt that comprises a divalent cation; and ii. a bioactive compound, wherein said biodegradable ionic precipitate is encapsulated by a lipid bilayer membrane, wherein;
said lipid bilayer membrane comprises an inner leaflet and an outer leaflet, wherein said inner leaflet comprises a first lipid that is a non-cationic lipid and said outer leaflet comprises a second lipid, wherein said lipid bilayer membrane is asymmetric, and
said first lipid is capable of forming ionic interactions with said biodegradable ionic precipitate.

2. The delivery system of claim 1, further comprising a lipid-polyethylene glycol (PEG) conjugate, wherein said lipid-PEG conjugate comprises PEG in an amount between about 12 mol % to about 50% of total surface lipid.

3. The delivery system of claim 1, wherein said bioactive compound is selected from the group consisting of antimicrobials, antibiotics, antimycobacterials, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, antianxiety agents, antidepressant agents, anorexigenics, non-steroidal anti-inflammatory agents, steroidal anti-inflammatory agents, antioxidants, vaso-active agents, bone-active agents, antiarthritics, and diagnostic agents.

4. The delivery system of claim 1, wherein said bioactive compound is an antiviral or anticancer drug.

5. The delivery system of claim 1, wherein said bioactive compound is gemcitabine monophosphate.

6. The delivery system of claim 1, wherein said salt further comprises a trivalent cation.

7. The delivery system of claim 1, wherein said salt is calcium phosphate precipitate.

8. The delivery complex of claim 1, wherein said bioactive compound is phosphorylated.

9. The delivery system complex of claim 1, wherein said bioactive compound is mono phosphorylated.

10. The delivery system complex of claim 1, wherein said bioactive compound comprises a polynucleotide or a polypeptide.

11. The delivery system complex of claim 10, wherein said polynucleotide comprises an interfering RNA.

12. The delivery system complex of claim 10, wherein said polynucleotide comprises an siRNA.

13. The delivery system complex of claim 10, wherein said polynucleotide is a plasmid DNA.

14. The delivery system complex of claim 2, wherein said lipid-PEG conjugate comprises a PEG molecule having a molecular weight of about 2000-5000g/mol.

15. The delivery system complex of claim 14, wherein said lipid-PEG conjugate comprises a 1,2-distearoyl-sn-glycero-3-phosphoethanolamine-N-carboxy-polyethylene glycol$_{2000}$ (DSPE-PEG$_{2000}$).

16. The delivery system complex of claim 1, wherein said outer leaflet comprises a targeting ligand.

17. The delivery system complex of claim 16, wherein said targeting ligand is selected from the group consisting of asialoglycoprotein, insulin, low density lipoprotein (LDL), folate, benzamide derivatives, peptides comprising the arginine-glycine-aspartate (RGD) sequence, and monoclonal and polyclonal antibodies directed against cell surface molecules or mixtures thereof.

18. The delivery system complex of claim 17, wherein said benzamide derivative comprises anisamide.

19. The delivery system complex of claim 1, wherein said delivery system complex has a diameter of about 15 to about 120 nm.

20. The delivery system complex of claim 1, wherein said delivery system complex has a diameter of about 25 to about 30 nm.

21. The delivery system complex of claim 1, wherein said second lipid is a cationic lipid.

22. The delivery system complex of claim 21, wherein said second lipid is DOTAP.

23. A method of making the delivery system complex of claim 1, comprising
a) mixing a first reverse microemulsion comprising a metal chloride and a second reverse microemulsion comprising a metal phosphate and said first lipid having a free phosphate group to form said biodegradable ionic precipitate, encapsulating said precipitate with said first lipid, and wherein said bioactive compound is present in said first reverse microemulsion or said second reverse microemulsion;
b) washing said biodegradable ionic precipitate;

c) solubilizing said biodegradable ionic precipitate in a volatile, organic solvent to form a biodegradable ionic precipitate/solvent mixture;

d) adding said second lipid to said biodegradable ionic precipitate/solvent mixture; and e) evaporating said volatile organic solvent to produce said delivery system complex.

24. The delivery system complex of claim 10, wherein said polynucleotide comprises a mRNA.

25. The delivery system complex of claim 10, wherein said polynucleotide comprises a miRNA.

26. The delivery system complex of claim 10, wherein said polynucleotide comprises non-coding RNA.

27. The delivery system complex of claim 1, wherein said inner leaflet comprises a phosphatidic acid.

\* \* \* \* \*

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: siRNA target sequence

<400> SEQUENCE: 1
cttacgctga gtacttcga                                          19

<210> SEQ ID NO 2
<211> LENGTH: 21
<212> TYPE: DNA
<213> ORGANISM: Artificial Sequence
<220> FEATURE:
<223> OTHER INFORMATION: siRNA target sequence

<400> SEQUENCE: 2

```
aattctccga acgtgtcacg t                                            21

<210> SEQ ID NO 3
<211> LENGTH: 9
<212> TYPE: PRT
<213> ORGANISM: Artificial Sequence
<220> FEATURE:
<223> OTHER INFORMATION: EV peptide
<220> FEATURE:
<221> NAME/KEY: PHOSPHORYLATION
<222> LOCATION: (5)...(5)

<400> SEQUENCE: 3

Glu Glu Glu Glu Tyr Phe Glu Leu Val
1               5
```